United States Patent
Sutter

(10) Patent No.: US 6,726,480 B1
(45) Date of Patent: Apr. 27, 2004

(54) SUPPORT FOR SUSTAINING AND/OR FORMING A DENTAL PROSTHESIS

(75) Inventor: Franz Sutter, Niederdorf (CH)

(73) Assignee: Straumann Holding AG, Waldenburg (CH)

( * ) Notice: Subject to any disclaimer, the term of this patent is extended or adjusted under 35 U.S.C. 154(b) by 0 days.

(21) Appl. No.: 09/424,515
(22) PCT Filed: May 18, 1998
(86) PCT No.: PCT/EP98/02904
  § 371 (c)(1),
  (2), (4) Date: Apr. 17, 2000
(87) PCT Pub. No.: WO98/52487
  PCT Pub. Date: Nov. 26, 1998

(30) Foreign Application Priority Data

May 24, 1997 (CH) ............................................. 1218/97
May 24, 1997 (CH) ............................................. 1221/97

(51) Int. Cl.⁷ ................................................. A61C 8/00
(52) U.S. Cl. ..................................................... 433/173
(58) Field of Search ................................. 433/172, 173, 433/174, 175, 176

(56) References Cited

U.S. PATENT DOCUMENTS

| 4,772,204 A | * | 9/1988 | Soderberg | 433/174 |
| 5,000,685 A | * | 3/1991 | Brajnovic | 433/173 |
| 5,000,686 A | | 3/1991 | Lazzara et al. | 433/174 |
| 5,069,622 A | * | 12/1991 | Rangert et al. | 433/173 |
| 5,104,318 A | * | 4/1992 | Piche et al. | 433/173 |
| 5,108,288 A | * | 4/1992 | Perry | 433/173 |
| 5,110,292 A | * | 5/1992 | Balfour et al. | 433/173 |
| 5,125,840 A | | 6/1992 | Duerr | 433/173 |
| 5,310,343 A | * | 5/1994 | Hasegawa et al. | 433/173 |
| 5,362,235 A | * | 11/1994 | Daftary | 433/172 |
| 5,407,359 A | * | 4/1995 | Balfour et al. | 433/173 |
| 5,667,384 A | | 9/1997 | Sutter | 433/173 |
| 5,688,123 A | * | 11/1997 | Meiers et al. | 433/173 |

FOREIGN PATENT DOCUMENTS

| DE | 3302968 | | 8/1984 | |
| DE | 4001183 | | 7/1991 | |
| EP | 0419431 | | 3/1991 | |
| EP | 0530160 | | 3/1993 | |
| EP | 0438048 | | 4/1993 | |
| EP | 0629384 | | 11/1994 | |
| JP | 5-145 | | 1/1993 | |
| JP | 8-47500 | | 2/1996 | |
| WO | WO 093006786 A | * | 4/1993 | 433/174 |
| WO | WO 094009717 A1 | * | 5/1994 | 433/174 |
| WO | WO 96/37161 | | 11/1996 | |

OTHER PUBLICATIONS

English Translation of Japanese Office Action dated Mar. 12, 2003.

* cited by examiner

Primary Examiner—Cary E. O'Connor
(74) Attorney, Agent, or Firm—Crowell & Moring LLP

(57) ABSTRACT

A support for sustaining and/or forming a dental prosthesis, comprises an axle, an anchoring part which can be anchored in a bone or a master model, and a head part which protrudes out of said bone or master mode. The head part has intermediate spaces distributed around the axis, i.e., several first intermediate spaces forming a divided circle, and a second, wider and/or deeper intermediate space. A cap can be fixed to the support. The cap has at least one projecting part for engaging in an intermediate space and, optionally, can be configured for fixing in several different rotational positions or a single rotational position, the support allowing exact positioning. The cap can also be produced without a projecting part of the type mentioned. The same support can be used to form different types of dental prostheses.

48 Claims, 33 Drawing Sheets

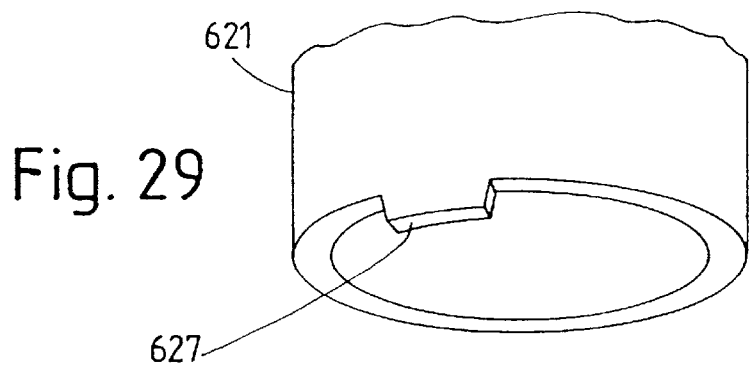
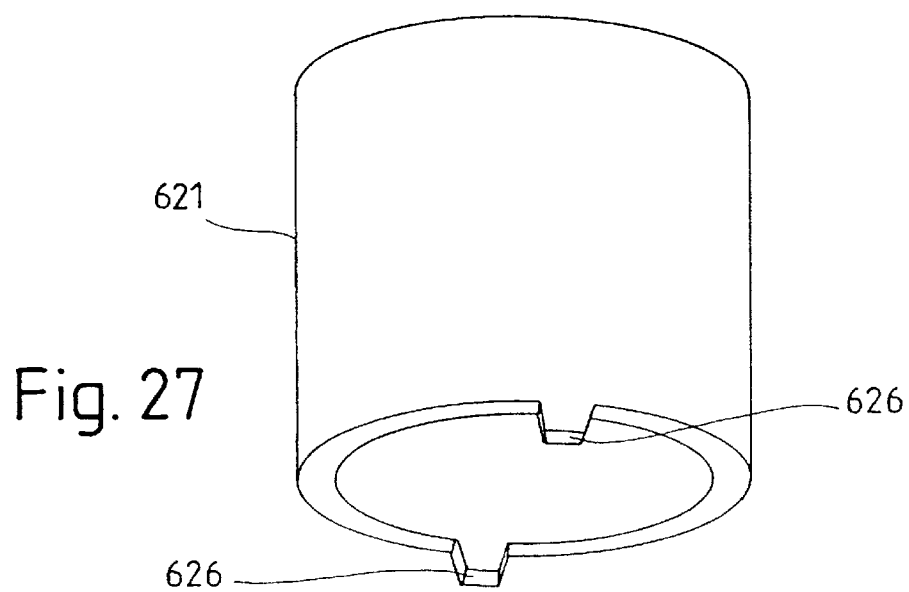
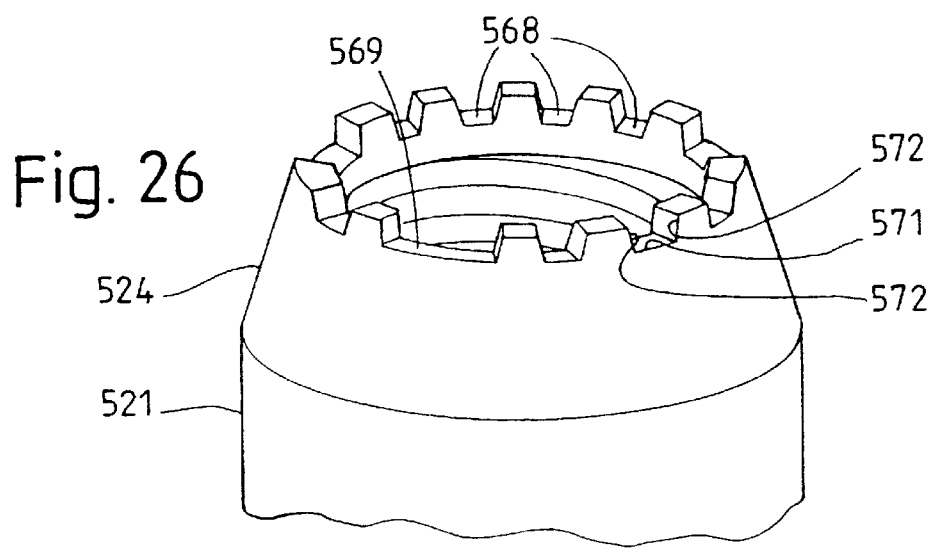

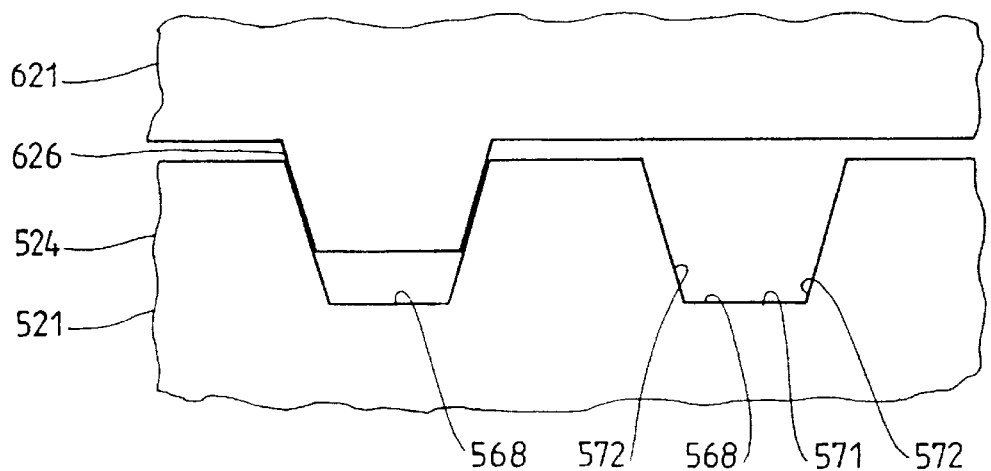
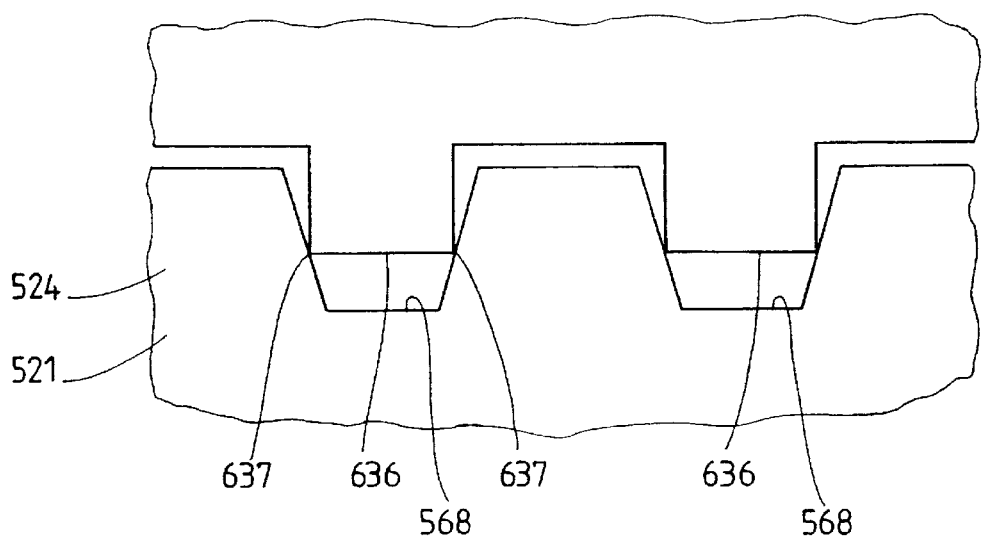

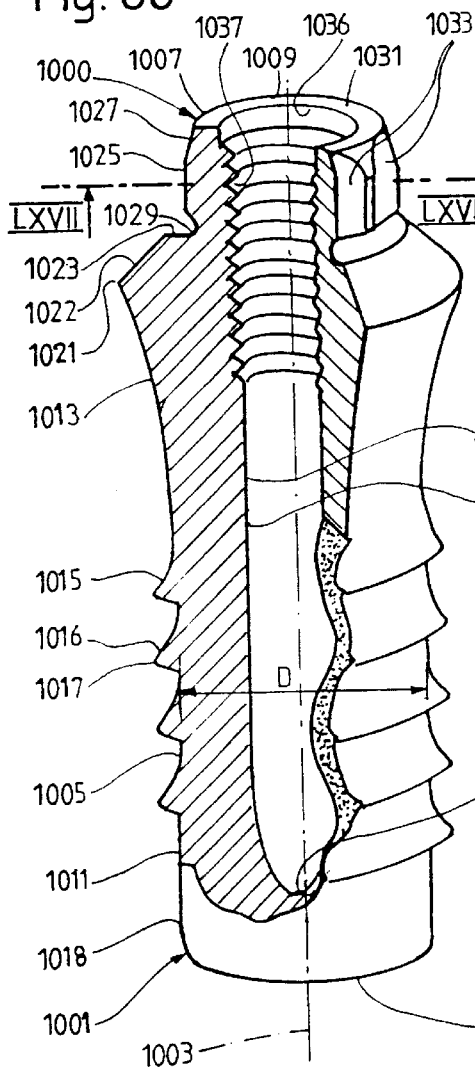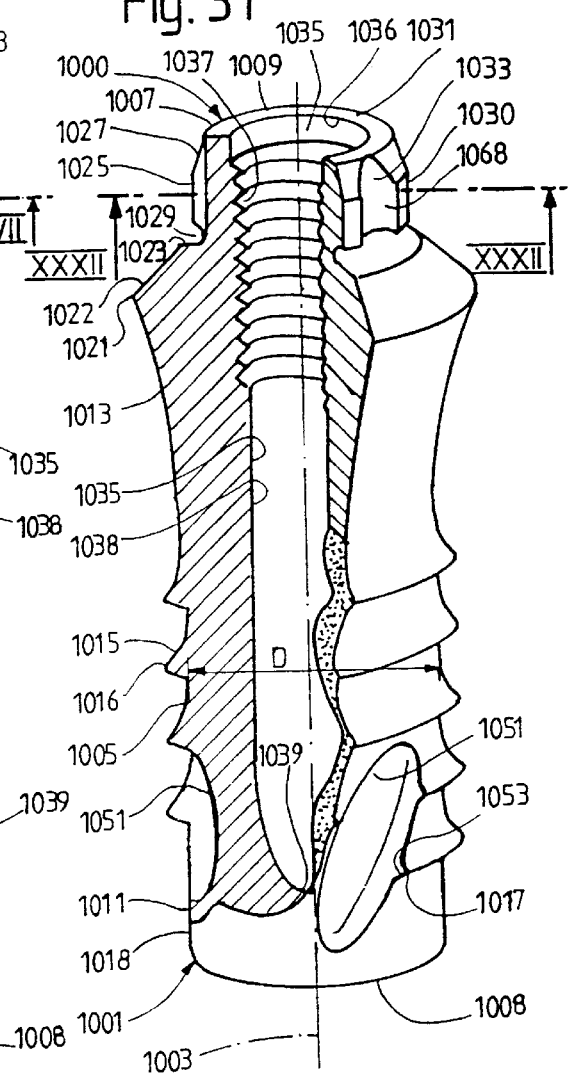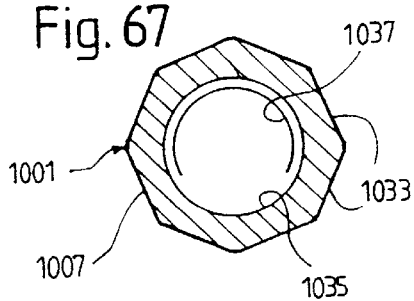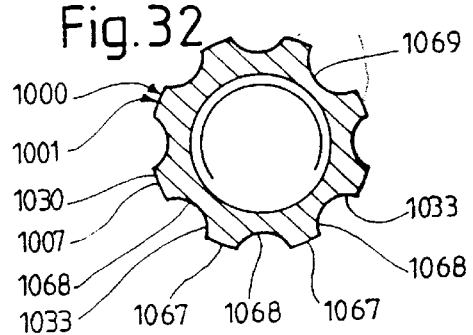

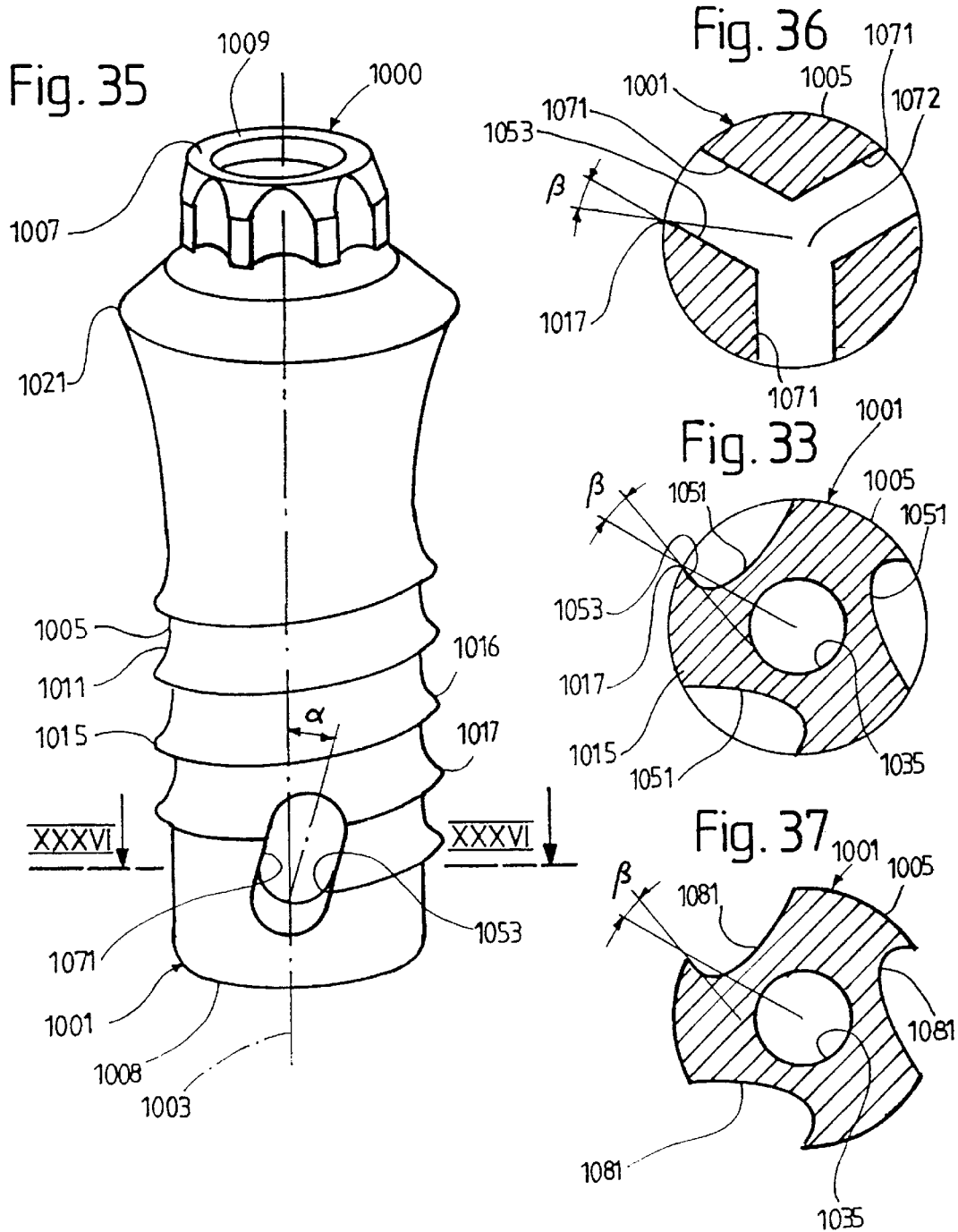

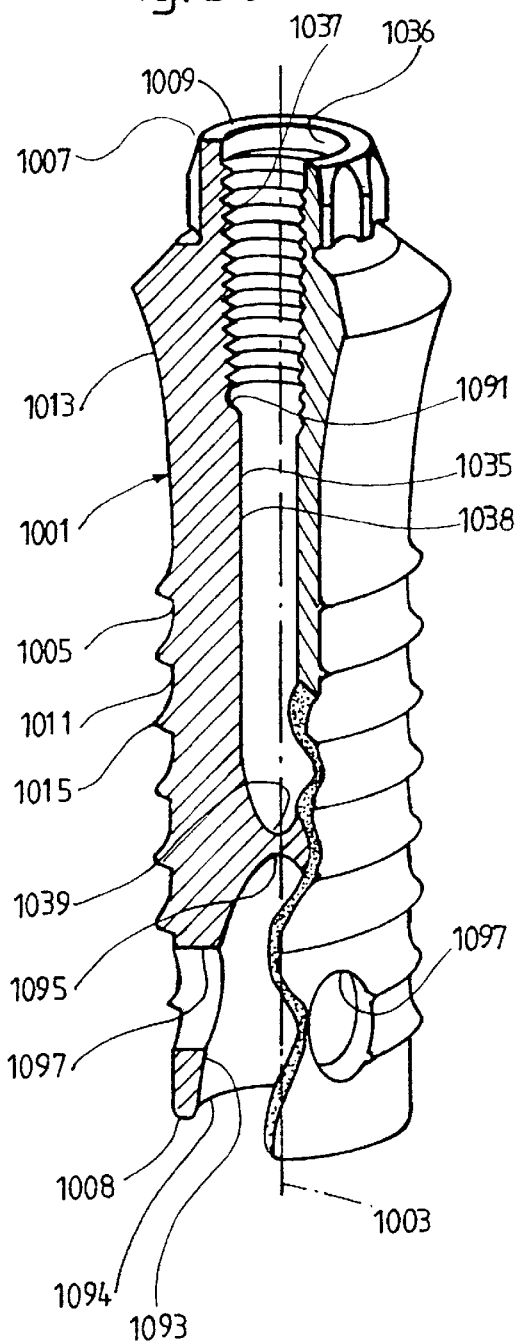
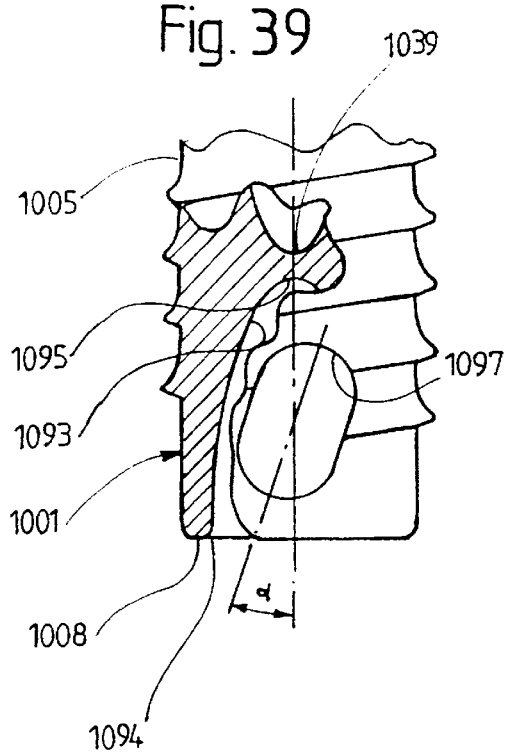

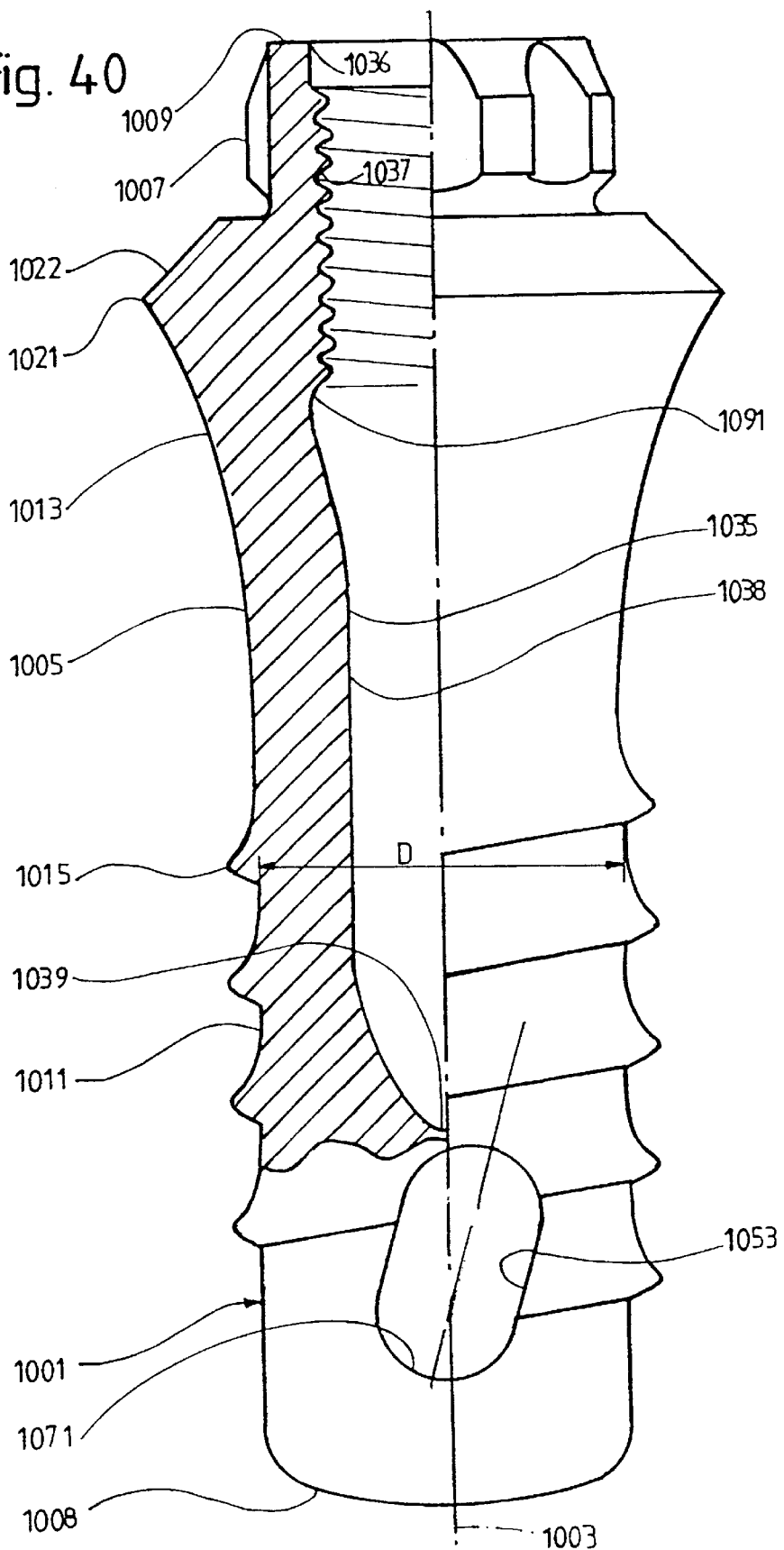

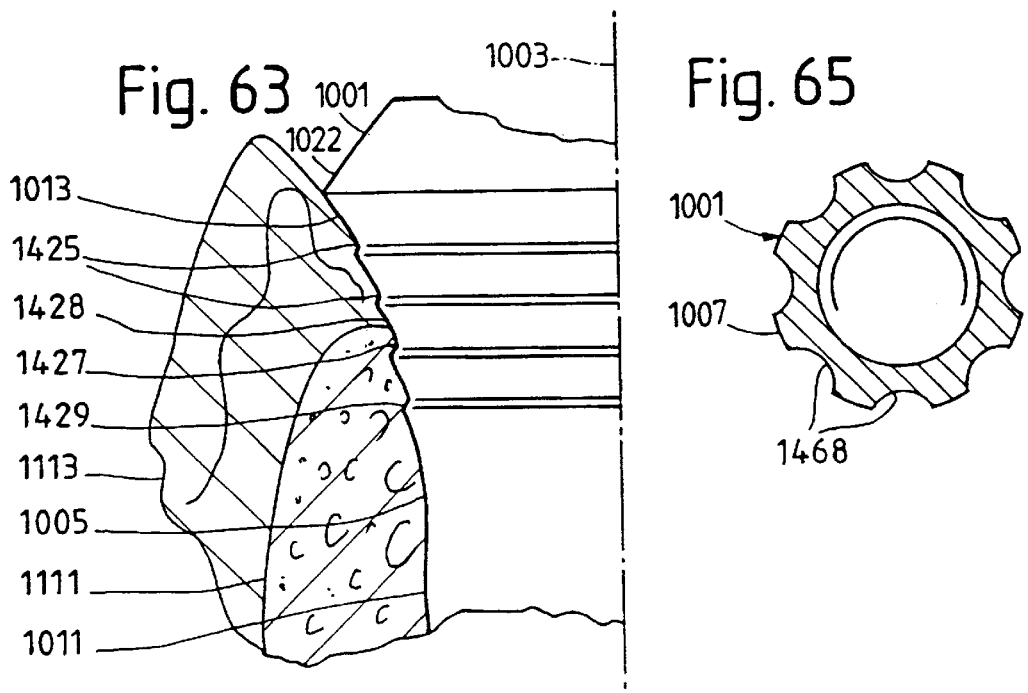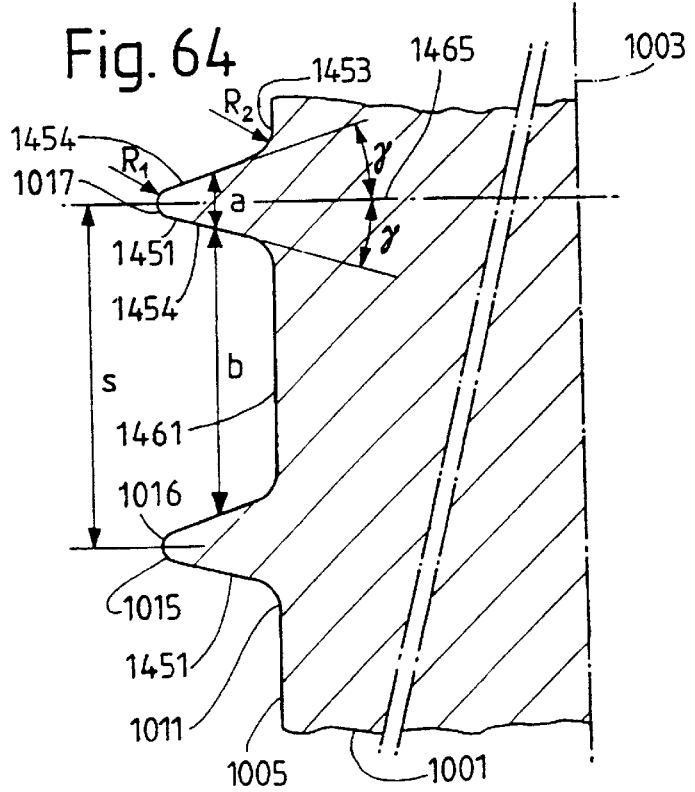

SUPPORT FOR SUSTAINING AND/OR FORMING A DENTAL PROSTHESIS

TECHNICAL AREA

The invention relates to a support for holding and/or forming a dental prosthesis with an axis, an anchoring part for anchoring in a bone of the lower or upper jaw of a patient and/or in a master model and a head part intended to project from the bone and/or master model. This head part serves to support an originally separate element attachable to the support with a cap. The cap can for example be a part of a dental prosthesis such as an individual artificial tooth or a bridge or a prosthesis having several teeth. The possibility also exists however of first attaching a so-called burnout cap made of plastic to the support. The burnout cap can serve for making a casting model and a casting impression, then be burned off from the latter and replaced by a impression cap when the cast impression is used.

PRIOR ART

For certain applications, it should be possible to attach the cap in a specific rotational position on the support. A support known from EP 0 685 208 A has an implant and a secondary part having an external thread screwed into the internal thread of the implant and a head projecting from the implant. This forms the head part of the support and has an octagonal section as well as a conical section that tapers away from the latter to the front side of the head. A superstructure element or impression element with a cap can be associated with the known secondary part and have an internal space with an octagonal section. FIG. 1 of the present patent application is a cross section through an area of the octagonal section of the head of a known secondary part 1. The secondary part defines an axis 5 and straight lines running radially thereto through the corners of the octagonal head section, one of which is designated 7. Cap 10 is shown in FIG. 1 in the central intended rotational position provided. In this position, each corner of the octagonal section of the internal space of the cap is on the straight line 7 running through the associated corner of secondary part 1. The cap rests on the secondary part with radial play so that the mutually associated octagonal surfaces of the secondary part and the cap are at a distance a from each other. The radial play must be so great, particularly when burnout caps are used, that the internal weight of the superstructure element then made by casting can differ due to shrinking processes and the like from the internal weight of the burnout cap. Because of the play, cap 10 can be turned starting in its central desired rotational position in two rotational directions through an angle designated a in FIG. 2 until the octagonal surfaces of the cap are located at the corners of the secondary part. Distance a is typically approximately 0.02 mm and possibly even more with burnout plastic caps. Angle a then amounts to approximately 2.25° or more. The cap can be rotated back and forth through an angle 2a, namely approximately 4.50° or more. The octagonal head section of the known support thus makes possible only very inexact positioning of the cap relative to rotations about the axis. If large forces act on the cap approximately perpendicularly to the axis and bring about shear forces or torsional forces between the cap and the support, there is the danger that the cap will execute small rotational or swiveling movements relative to the support. Such tiny rotational movements may cause the dental treatment to fail. The cap can be mounted on the head in one of eight selectable rotational positions. Sometimes, however, it is advantageous for the cap to be placed on the support in only a single rotational position, which is not possible with the known support. Moreover, the cap rests only on the octagonal section, but not on the conical section of the head. In this known head, it would also be practically impossible to design a cap so that it abuts both the flat surfaces of the octagonal section and the conical section of the head. Since the octagonal section has only a relatively small axial dimension, the cap receives little support with respect to laterally acting forces, i.e. forces transverse to the axis, impairing the stability of the connection of the cap or the superstructure element to the additional support.

DE 195 34 979 C discloses a support with an implant and a spacing sleeve. The latter serves as a head for attaching a dental prosthesis. The implant has an axial blind hole. Its internal surface is provided with six grooves distributed around the axis of the implant. The spacing sleeve projects into the blind hole of the implant and has noses engaging these grooves so that the spacing sleeve can be positioned in six different rotational positions in the implant. This support has the disadvantage however that the spacing sleeve is guided laterally only in a short cylindrical guide area of the hole having a relatively small diameter below the grooves and is supported against the forces directed approximately transversely at the implant axis. If such forces act on the dental prosthesis, a long lever arm is produced between the point where these forces act and the guide area of the hole, so that very high torques have to be transmitted from the spacing sleeve to the implant in the guide area of the blind hole. In combination with the small dimensions of the guide area, this results in a high risk of the dental prosthesis executing micromovements relative to the implant when stressed, leading to failure of the dental treatment. Moreover, the implant of this known support must be inserted approximately flush with the ridge of the bone. This subgingival arrangement of the implant has the disadvantage that the gum (gingiva) knits over the implant during the healing phase and requires a further incision to attach the spacing sleeve. Moreover, the dental prosthesis cannot be removably fastened to the spacing sleeve. Moreover, the known support is not suitable for anchoring bridges, either.

A support shown in FIGS. 1–3 of CA 1,313,597 A has an implant and a generally conical sleeve. There are two axial projections at the upper end of the implant which, when the device is assembled, engage flats on the sleeve and position it non-rotatably in one of two possible rotational positions. In the version shown in FIGS. 4 and 6, the implant has a projection that is generally cylindrical but is provided on one side with a flat. The flat permits non-rotatable positioning of the sleeve in a single rotational position. Since the two projections and the flat of these known implants each have only one flat surface tangential to the axis of the implant that abut a flat matching surface on the sleeve, these implants define the rotational position of the sleeve in the same way no more exactly than the supports commented on above and known from EP 0 685 208 A. In addition, these implants can position a sleeve in only two different rotational positions or even in only one single rotational position. In many applications, the rotational position of a cap, however, must be selectable from more than two rotational positions. In addition, the crown prosthesis in these implants must clearly be supported at least essentially by one additional cap whose rotational position is not defined at all. The supports known from CA 1,313,597 A that serve to hold a screw-on cap are also composed of at least three separate parts. This large number of parts makes dental treatment complicated and adversely affects the stability of the dental prosthesis in the mouth of a patient.

A support shown in FIGS. 1–3 of CA 1,313,597 A contains an implant and a generally conical sleeve. The implant has two axially projecting projections at the upper end which engage flats on the sleeve when the device is assembled and position them non-rotatably in one of two possible rotational positions. In the version shown in FIGS. 5 and 6, the implant has an extension which is generally cylindrical but provided on one side with a flat. The flat permits non-rotational positioning of the sleeve in a single rotational position. Since the two projections and the flat of these known implants each abut the flat opposite surface of the sleeve with only one flat surface tangential to the axis of the implant, just like the supports commented on above and known from EP 0 685 208 A, these implants define the rotational position of the sleeve only imprecisely. In addition, these implants can position the sleeve only in two different rotational positions or even in only a single rotational position. In many applications, however, the rotational position of a cap must be selectable from more than two rotational positions. In addition, the artificial crown in these implants is clearly supported at least essentially by an additional cap whose rotational position is not even defined. The supports known from CA 1,313,597 A that serve to hold a cap that can be screwed on are also composed of at least three separate parts. This large number of parts makes dental treatment complicated and adversely affects the stability of the dental prosthesis in the mouth of a patient.

EP 0 475 299 A teaches an implant or a basic body, a spacing sleeve upper part, and a spacing sleeve bottom part that can be screwed into the basic body. The basic body has an axial blind hole with female snap connectors distributed along its circumference into which the male snap connectors of the spacing sleeve upper part engage when the implant is assembled. The spacing sleeve upper part is guided in the implant only by an annular recess in the blind hole and is supported against lateral forces, in other words forces directly approximately transversely to the axis of the implant. Between the annular recess and the dental prosthesis, not visible, there is a relatively long lever arm. In addition, the annular recess is only relatively short and indeed must be short because the blind hole contains an internal thread and the female snap connectors as well. When forces act approximately transversely to the axis of the implant in the dental prosthesis, there is the danger that the spacing sleeve will make micromovements relative to the implant. In addition, additional separate parts in addition to the parts shown in EP 0 475 299 A are also probably necessary for fastening an artificial crown so that the entire device is composed of many individual parts, adversely affecting the stability even more.

GIST OF THE INVENTION

The goal of the invention is to avoid the disadvantages of the known supports and of a device formed therefrom, as well as a superstructure and/or impression element and/or a healing element. In particular the opportunity is to be offered for an element with a cap to be normally positioned stably on the support in a rotational position defined as accurately as possible so that the cap, even with high forces acting on it approximately transversely to one axis of the support and/or torsional stresses, remains connected with the support permanently and in stable fashion. In addition, it should preferably be possible to secure a cap to a given support, depending on the design of the cap, in a rotational position selectable from one of several rotational positions or only in a single rotational position on the support. In addition, a device is to be created having a cap that can be fastened in stable fashion in any free rotational position to a support that permits the rotational position to be established.

This goal is achieved according to the invention by a support for holding and/or forming a dental prosthesis with an axis, and anchoring part intended for anchoring in a bone and/or a master model, and a head part intended to project out of the bone and/or master model and an annular shoulder surface located between the anchoring part and the head part and forming an angle with the axis; the head part has a peripheral surface as well as a face and the support is characterized by the fact that the head part has several projections and interstices located at the periphery and/or face and alternating around the axis.

The invention also relates to a device with a support and with an element that can be fastened to the support, with the device being characterized by the fact that the element has a supporting surface intended to rest on the shoulder surface and surrounds the head part in cross section in the state in which it rests on the shoulder surface.

Advantageous improvements on the support and the device follow from the dependent claims.

For example, the support can consist of a metal implant or primary part and an originally separate metal secondary part, preferably removably fastened to the implant, for example screwed thereto, which is provided with the projections and interstices serving for positioning. However, the support can instead have a one-piece body which extends from the free end of the anchoring part up to the free end of the head part and forms these ends so that the support consists at least essentially completely of a one-piece implant made of metal for example. In addition, the support can be made as a manipulating support placed by a dental technician in a master model made of plaster for example and is used to form a superstructure. The head part projecting out of the master model of such a manipulating support should then have the same design as a support used for insertion into a bone of a patient while the anchoring part of the manipulating support inserted into the master model usually differs from the anchoring part of the support placed in a bone.

The head part of the support according to the invention has interstices distributed around the axis. These interstices form positioning surfaces that are not rotational symmetrical with the axis for non-rotational positioning of a superstructure and/or impression element. Each interstice preferably forms a depression relative to a line that lies in a plane at right angles to the axis and contacts the head part on sides of the interstice facing away from one another. Each interstice for example is in the form of a groove or formed by a groove; the terms "groove-shaped interstice" and "groove" shall be construed to include both an elongate interstice and an elongate groove as well as an interstice or groove that has a width approximately the same size as the length or even greater than the length of the interstice or the groove. The interstices or grooves are open for example on the two ends that face away from each other. Each interstice is preferably delimited least partially by flats which are approximately parallel to a radial center line that runs through the axis and through the middle of the interstice or a central plane or form an angle of at most 60° and preferably no more than 45° with such a line or plane. Each interstice for example has two essentially flat, lateral surfaces and is approximately U-shaped or V-shaped in cross section. The interstices can however be at least partially or completely arcuate in cross section and for example can be at most or approximately semicircular. In this case then, for example at least certain flats of the arcuate limiting surface of each interstice can be located relative to a center line or center plane of the type mentioned above in the manner described above and/or define tangential planes arranged in the manner described.

An element, for example a superstructure element and/or an impression element and/or a healing element, can be fastened or possibly non-removably fastened on the support. Such an element can have a cap and/or be formed by a cap. The element can also have a burnout cap made of plastic or can consist exclusively of such a cap. The element or cap can rest on the annular shoulder surface of the support by a smooth, annular supporting surface surrounding the head part in axial projection, with no interruptions or gaps around the axis. The element can also have a least one projection which can engage an interstice of the head part of the support. The support can position such an element in at least one rotational position.

The projection, or each projection, engaging an interstice of the support of a superstructure element and/or impression element or other element and the projection (or each projection) of the support preferably engaging an interstice of the element can for example have a certain amount of play in the interstice so that the projection, despite possible inaccuracies in manufacture and despite changes in dimensions caused by changes in temperature, can be inserted easily into the interstice. The play measured along a circle surrounding the axis of the support or tangentially to such a circle can however be made so small that the superstructure element, in the state in which it has been positioned but not yet fastened, can be rotated back and forth through an angle that is preferably no more than 2° and for example even only 1° at most. This also is the case in particular in a burnable cap and a superstructure element cast and made with the aid of such a cap. The support therefore permits exact positioning of a superstructure element having at least one projection and/or impression element.

The head part of the support preferably has a section parallel to the axis and generally cylindrical and a generally conical section that tapers away from the latter toward the free end of the head part. The head part can then for example have groove-shaped interstices or grooves arranged on the peripheral surface and extending approximately axially, which extend at least through an area of the generally cylindrical section and through the conical section of the head part to the free end of the latter. The head part, instead of the interstices or grooves that are axial and arranged on the circumferential surface or in addition to such, can have interstices or grooves located on the face and running approximately radially, at least some of which have openings located in the circumferential surface of the conical section of the head part, or form such openings.

When an element is fastened to the support removably or non-removably and rests on the shoulder surface of the support, it can be supported by the head part at least at the conical section with at most a small amount of play with the conical peripheral surface and/or—when the head part has approximately axial interstices or grooves located at the peripheral surface—in the interstices or grooves. The peripheral surface of the conical head section and/or the boundary surfaces of the interstices support the element in directions that run approximately at right angles to the conical circumferential surface and/or the axis of the support. When the interstices are located on the face of the head part and the element has projections that extend into such interstices, the lateral surfaces of the interstices support the element, among other things, also in directions that are at right angles approximately to the axis. The play between the conical peripheral surface of the conical section of the head part and the conical internal surface of an element fastened to the support can be made very limited. The play for example in the surface sections provided for support can be, for example in the radial direction and/or in directions that are at right angles to the conical surfaces, a maximum of 0.02 mm or only 0.01 mm at most and especially at the conical surfaces the play is preferably in the micron range, for example a maximum of 5 microns or 3 microns at most.

The axial dimension or height of the head part is advantageously so small that the implant can be placed optionally subgingivally or transgingivally or in a position in which it is semi-submerged in the gingiva in the mouth of a patient. The design of the head part makes it possible for the latter to support a superstructure element or impression element held by the support, despite a small axial dimension of the head part, in all directions running approximately transversely to the axis in all applications. This in turn ensures that the superstructure element fastened to least one support in the mouth of a patient will be connected stably and permanently with the support (or each support) serving to fasten it and will not be loosened even by high forces directed approximately transversely to the axis of the support or to the axes of the supports.

A superstructure or other element can therefore be fastened very stably, at least approximately free of micromovements, and permanently on the support relative to approximately axial forces, with respect to forces directed approximately transversely to the axis, and with respect to torsional rotation about the axis.

In a preferred embodiment, the interstices of the support include a plurality of first interstices with identical shapes and identical dimensions, especially identical widths and identical depths, and a second interstice which has a larger dimension in at least one direction than the first interstices and for example is wider and/or deeper than they. The first interstices adjacent to one another are equally spaced apart from one another as measured along a partial circle coaxial with the axis of the support and together define a division of a circle or simply a division. For clarification, it should be pointed out that the division is equal to the n-th part of a full circle where n is a whole number and is advantageously at least 6 and at most 72 so that the division angle is advantageously in the range from 60° to 5°. In one advantageous embodiment, n is at least 8 and especially when the interstices are arranged on a peripheral surface, it is still more preferably at least 10° and for example 12° to 36°. The second interstice for example can be formed by the fact that, at least theoretically, one can start with identical projections and first interstices distributed uniformly on a full circle and remove or omit at least one and possibly more of these projections. The resultant second, wider interstice has a dimension measured along the partial circle which is equal to the sum of a dimension measured along the partial circle of a first interstice and one complete division or several complete divisions. A second, wider interstice can however be formed instead by making one projection or two adjacent projections narrower than the remaining projections.

An element fastened to the support for example can have a positioning section with projections distributed uniformly along its periphery which all have the same shapes and dimensions and are separated from one another by likewise similarly designed interstices and can engage all the interstices of the support. Such an element can be fastened relative to the axis of the support in various selectable positions, in other words rotational positions on the support, with each selectable position, i.e. rotational position, being defined by the mutually meshing projections and interstices of the superstructure element and/or impression element and/or the support and with the rotational angle between the adjacent rotational positions being equal to the divisional angle established by the division of the identically designed (first) interstices in the head part. This manner of connecting an element with the support is referred to below as multipositioning of the element.

The element can also have a projection that has a larger dimension in at least one direction than the first interstices of the support and is so designed that it can engage the second interstice but not the first interstices of the support. This projection for example can be wider than the first interstices of the support and/or have a height greater than the depth of the first interstices of the support. The positioning section of the element then for example has, in addition to this projection, projections that are even narrower and/or lower for engaging the narrower, first interstices of the support but possibly have only the projections that engage the second, wider and/or deeper interstice of the support. The element can then be connected relative to the axis of the support only at a single rotational position with the support. This manner of connecting an element with the support is referred to below as single positioning of the element.

However, the element can also be produced without a positioning section and especially without positioning projections and be made so that, after fastening to the support, it does not engage any interstices of the support. The element can then be rotated continuously when mounted on the support until it is fastened so that the element can be fastened for example at any rotational position. This is referred to below as free positioning of the element.

In one advantageous embodiment of the support, an element with multipositioning or an element with single positioning or an element with free positioning can be fastened freely to the support. The type of element that is best depends on its purpose, the type of dental prosthesis to be formed, and the individual medical symptom. If for example a crown for an individual tooth is to be produced as the superstructure element, preferably a superstructure element is used that permits multiple or possibly single positioning so that the crown is precisely positioned and protected against rotation. A prosthesis that replaces a plurality of teeth for example can be fastened by least two supports, each of which has a telescoping base that has a cap for single positioning. To form a soldered base, a cap can likewise be used for single positioning. A bridge or a rib structure for a prosthesis can be secured for example by caps for free positioning on supports. A laboratory that makes supports for example can make caps that fit on a support and are provided for various types of positioning, and for example on a set of identical supports, as needed, can supply the dentist with a set of identical caps or a set of caps for various types of positioning. The dentist can then use these caps as impression elements and/or for making different superstructure elements such as crowns, bridges, and prostheses, and/or healing elements. Therefore, a given type of support can be used to hold a plurality of different types of superstructure elements and impression elements.

Bridges, partial prostheses, and full prostheses are frequently fastened with two or possibly even more supports. In this case, the supports ideally have axes parallel to one another. However in practice the axes are frequently at an angle to each another and for example diverge or converge toward the free ends of the head parts. The device according to the invention is designed in one advantageous embodiment such that an element, for example an impression element or superstructure element, is mounted on the head part in a displacement direction inclined to the axis of a support and can be pulled off the latter. It is then possible to pull two or more elements held on supports away from the supports simultaneously if the axes of the supports are not parallel to one another and form angles with one another that measure up to 30° or even up to 40° for example. The element, when pulled away from the support and when connected with the latter, can be displaced in a direction over the head part which forms an angle of up to 15° or even up to 20° with the axis of each support.

BRIEF DESCRIPTION OF DRAWINGS

The subject of the invention will now be described with reference to the embodiments shown in the drawings.

FIG. 26 shows a diagonal view of the head part of the device according to FIGS. 24 and 25;

FIG. 27 shows a diagonal view of a positioning sleeve of the device according to FIGS. 24 and 25, designed for multipositioning;

FIG. 28 shows a development of sections of the head part and the positioning sleeve of the device shown in FIGS. 24 and 25;

FIG. 29 shows a diagonal view of a positioning sleeve for single positioning;

FIG. 30 shows a representation analogous to FIG. 28 with a variant of the positioning sleeve;

FIG. 31 shows a diagonal view of a one-piece, partially cut-open implant forming a support, the anchoring part of which has grooves interstices inclined to the axis;

FIG. 32 shows a cross section through the head of the implant visible in FIG. 31 along line XXII—XXII in FIG. 31;

FIG. 33 shows a simplified cross section through the implant according to FIG. 32, running through the grooves of the anchoring part;

FIG. 35 shows a diagonal view of the implant according to Sic—perhaps the intention was to delete one of these two words. Translator. FIG. 34;

FIG. 36 shows a simplified cross section along line XXXVI—XXXVI in FIG. 35 through the implant visible therein;

FIG. 37 shows a cross section analogous to FIGS. 35 and 36 through an implant, whose anchoring part has grooves extending to its free end;

FIG. 38 shows a diagonal view of a cut-away implant, which has an axial blind hole terminating in the free end of the anchoring part, and holes terminating therein;

FIG. 39 shows the lower end section of the implant according to FIG. 38 shown partially in side view and partially in section;

FIG. 40 shows an implant shown partially in side view and partially in axial section with an axial hole matching a small outside diameter of the anchoring part;

FIG. 63 shows a section through a bone and a part of a variant of an implant, shown in side view;

FIG. 64 shows an axial section through a region of the anchoring part of an implant with a thread;

FIG. 65 shows a cross section through the head part of a support, in which all the groove-shaped interstices of the head part have the same shape;

FIG. 66 shows a diagonal view of a support consisting of a one-piece implant, the head part of which has axial, flat positioning surfaces; and FIG. 67 shows a cross section through the head part of the support according to FIG. 66 along line VXVII-VXVII in FIG. 66.

DESCRIPTION OF PREFERRED EMBODIMENTS

Figure 3:
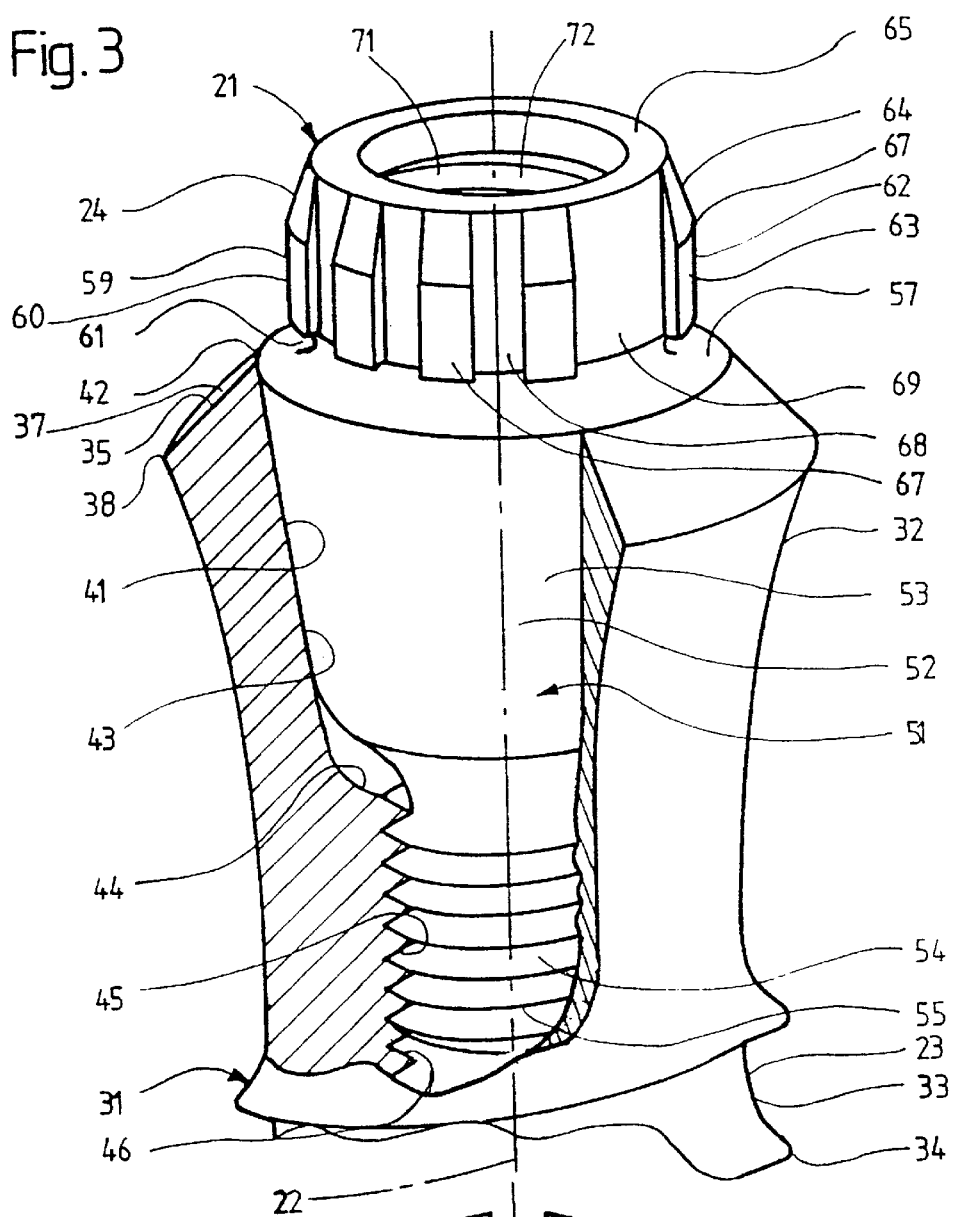
FIG. 3 shows a diagonal view of a support according to the invention with an implant and a secondary part removably attached thereto.
Figure 4:
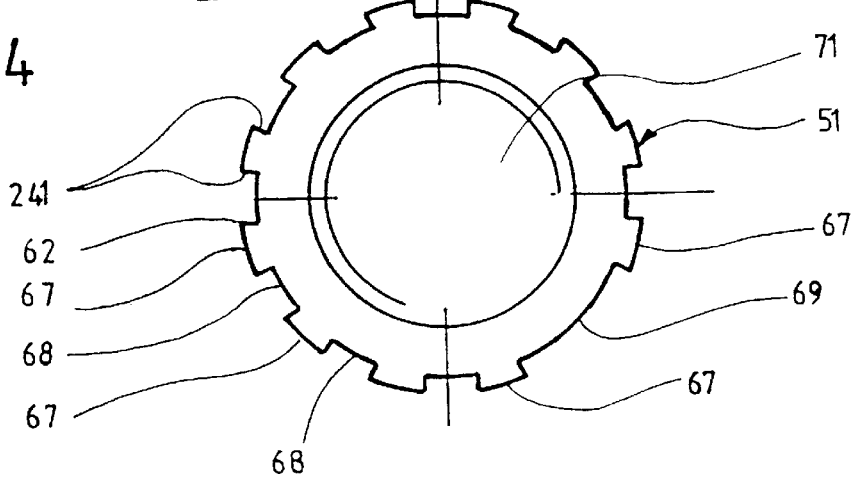
FIG. 4 shows a top view of the head of the secondary part shown in FIG. 3.

The support 21 shown in FIG. 3 is generally rotationally symmetrical about an axis 22 and at the bottom has an anchoring part 23 intended for anchoring in a bone of an upper or lower jaw and a head part 24 for projecting out of the bone. Support 21 has two originally separate elongate one-piece metal parts, namely an implant 31 and a secondary part 51 removably attachable thereto.

Implant 31 has an upper end section 32 that tapers downward. It is abutted at the bottom by a generally cylindrical section 33 which is provided for example with an external thread 34 and forms at least the largest part of anchoring part 23 of the support. The lower end of section 33, not visible in FIG. 3, forms the first free end of the total support. Implant 31 has an implant shoulder 35 at the upper end. This shoulder has an annular conical flat shoulder surface 37 that fully surrounds the axis and tapers upward away from the anchoring part. Head part 24 in axial projection is enclosed by at least the outer area of shoulder surface 37, namely by the entire shoulder surface 37. The shoulder surface forms an angle of 40° to 50° with axis 22 and has a circular edge 38 outside. The implant is provided with a stepped blind hole 41 that is generally coaxial with axis 22. This hole has an opening 42 located at the upper end of the implant and surrounded by the inner edge of implant shoulder 35 and has, in the downward direction therefrom, in the following order, a downwardly tapering conical main section 43, a shoulder 44, and a threaded hole 45 with an internal thread 46.

The secondary part 51, also visible in FIGS. 4 to 8, has an internal connecting section 52 which, when support 21 is assembled, is located in blind hole 41 of the implant.

Connecting section 52 has a downwardly tapering conical section 53 resting in the conical hole/main section 43 of the implant, and a threaded part 54 with an external thread 55 that is screwed into internal thread 46 of the implant with a torque of preferably 30 to 50 N cm. At the upper end of internal connecting section 52, the secondary part has a flat shoulder 57 flush with opening 42 of hole 41 and a head 59 located outside the implant and extending upward, said head forming at least a large part of head part 24 of support 21. Head 59 has a peripheral surface 60. This forms a positioning section 62 connected with shoulder 57 by an annular groove 61. Positioning section 62 at the bottom has a section 63 that is essentially parallel to axis 22 and is generally cylindrical and at the top, an upwardly tapering conical section 64. The peripheral section of the latter forms an angle with axis 22 that is smaller than the angle formed by shoulder surface 37 with axis 22 and preferably 10° to 30°, particularly preferably 15° to 25°, namely for example approximately 20° The free, upper end of the head has an annular, flat face 65 at right angles to axis 22 and forms the second, upper end of the total support.

Along its circumference, positioning section 62 has positioning projections 67 alternating with positioning interstices 68, 69. Positioning projections 67 are all the same shape. Positioning interstices 68, 69 consist of ten first, narrow positioning interstices 68 and a second, wider positioning interstice 69. Each positioning projection 67 consists of a straight, axial rib with two lateral surfaces, a top, and a bevel. The tops and the bevels are located in cylindrical section 63 or conical section 64 and define a cylindrical or conical surface coaxial to axis 22. Each interstice 68, 69 is approximately U-shaped in cross section and has two flat, lateral surfaces that are of course formed by the lateral surfaces of two adjacent projections and are approximately or exactly parallel to a plane running through axis 22 and the middle of the interstice in question. Also, each interstice 68, 69 has a bottom surface parallel to axis 22 forming for example a section of a cylindrical surface coaxial with axis 22, but which could instead consist of a plane parallel to the axis.

Figure 5:
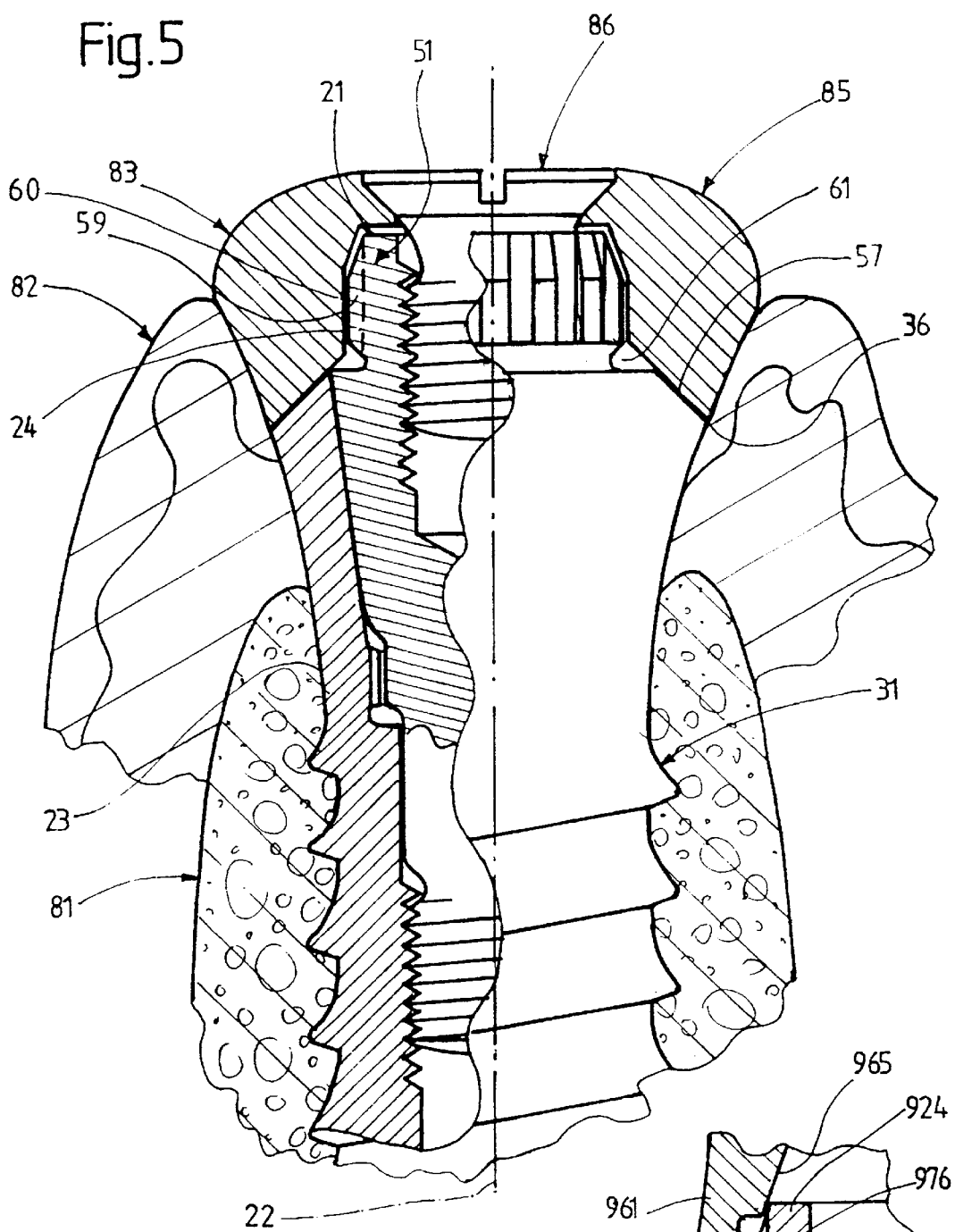
FIG. 5 shows a device drawn partially in section and partially in side view with the support designed according to FIG. 3 and installed in a bone, and a healing cap.

The second, wider interstice 69 is formed by leaving out one projection between two first interstices. The ten remaining first interstices 64 together define a circle with divisions of 12° to 30°. The radial depth of interstices 68, 69 is preferably dimensioned such that interstices 68, 69 extend up to the upper end of head 59 until they abut flat, annular end face 65 and form sections of its outer edge. The cylindrical surfaces defined by the bottom surfaces of interstices 68, 69 can have for example the same diameters as the upper, thinner ends of conical section 64, so that the lateral surfaces of interstices 68, 69 taper to a point at the upper end of the head. Also, the diameters of the cylindrical surfaces defined by the bottom surfaces of interstices 68, 69 can be approximately the same as the diameter of the lowest point of annular groove 61, so that the latter and the interstices blend continuously with one another for example. The axial dimension or the height of head 59 measured from shoulder 57 is preferably a maximum of 2 mm, preferably a minimum of 1 mm, more preferably at least 1.2 mm and for example approximately 1.5 mm. The first interstices 68 are preferably formed of grooves whose axial dimension is larger than their width. On the other hand, the second interstice 69 may have a width that is greater than its axial dimension. Secondary part 51 has a blind hole 71 terminating at its upper end, with an internal thread 72. FIG. 5 shows a bone 81 belonging for example to the lower jaw, covered with soft tissue 82, i.e. the gingiva, of a patient and a device designated as a whole by 83. The latter has the support 21 also shown in FIG. 1, a healing element 85, and an occlusal screw 86. Healing element 85 is cap-shaped and will be called "healing cap 85" below. To form device 83, a dentist can make an incision into soft tissue 82, create a hole in bone 81, insert implant 51 into the hole in bone 81, screw secondary part 51 tightly to implant 31, then screw healing cap 85 to the secondary part. Anchoring part 23 of support 21 is, at least for the most part, inside bone 81, while head part 24 projects therefrom. The upper end of secondary part 51 is approximately at the level of the ridge of the soft tissue 82 covering the bone, or a little higher. The conical supporting surface of healing cap 85 rests on implant shoulder 35. The healing cap has no projections that fit into the positioning interstices of the positioning section of the support and can thus be attached in any desired rotational position on the support. The healing cap then remains attached to support 21 for a certain period of time, so that the latter heals and the bone can knit to the implant to some degree. The above-mentioned small axial dimension of secondary part head 59 makes it possible for the covering surface of healing cap 85 that forms the upper end of device 83 to project at most slightly above soft tissue 82. This largely prevents forces exerted on device 83, arising when the patient chews, from interfering with the healing process of the implant. Also, the healing cap acts to shape the soft tissue that grows subsequently.

Figure 6:
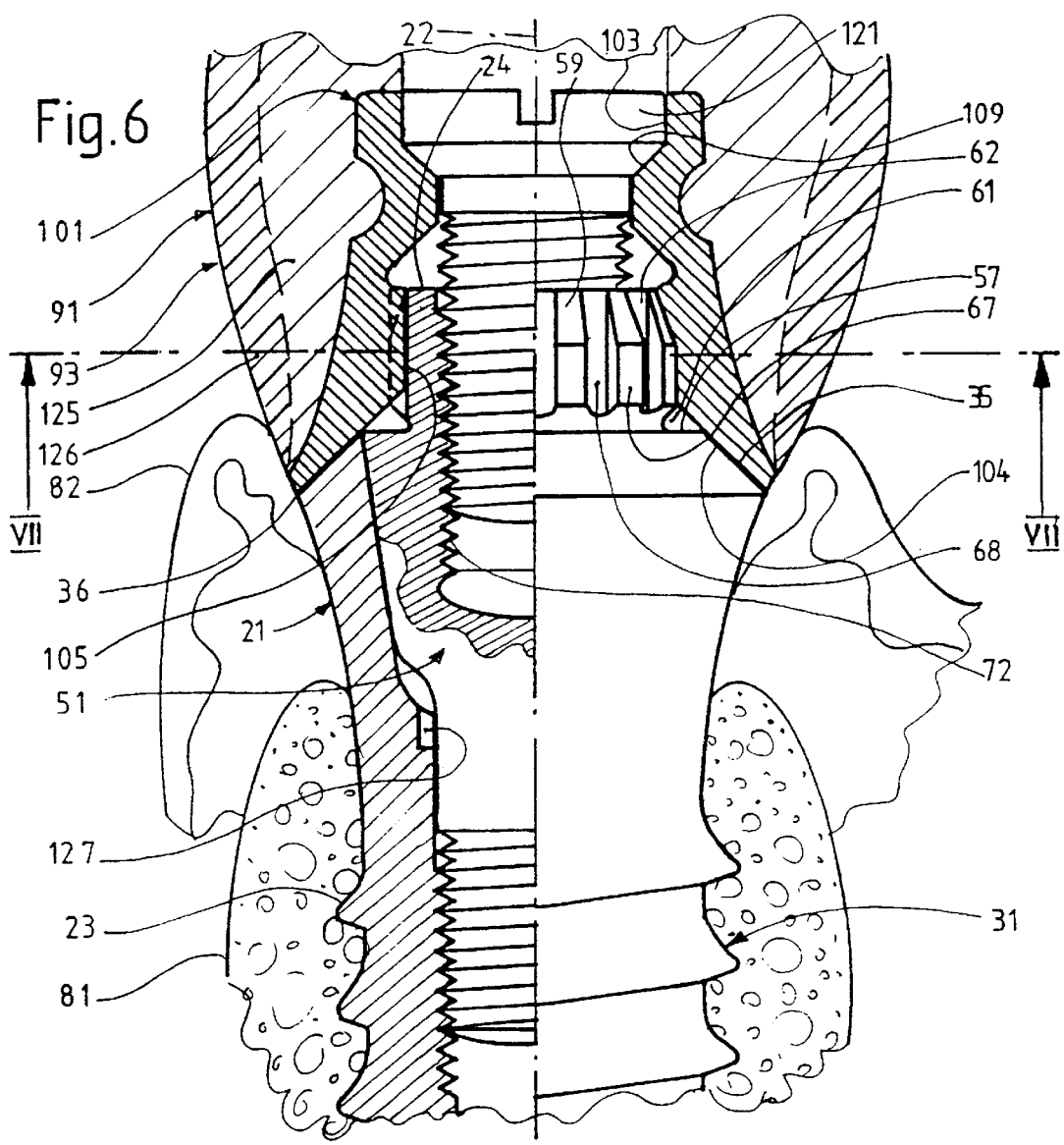
FIG. 6 shows a device drawing partially in section and partially in side view with the support according to FIG. 3 with a superstructure element with a cap for multipositioning.
Figure 7:
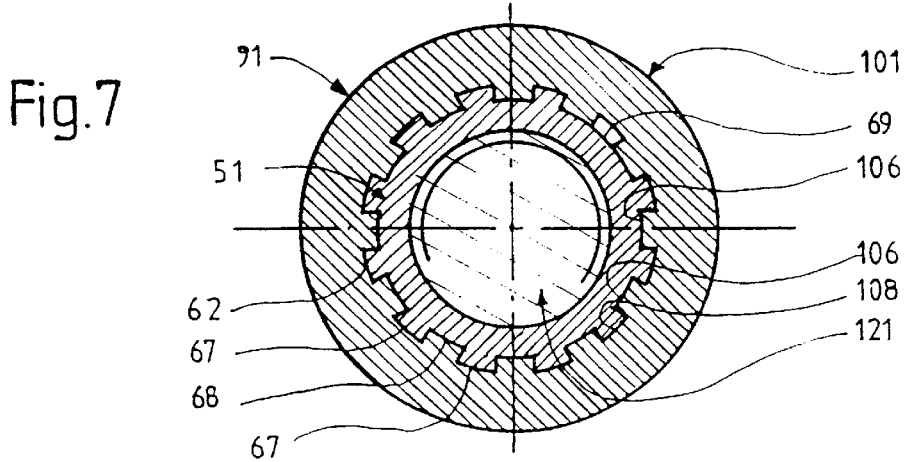
FIG. 7 shows a cross section through the device shown in FIG. 6 along line VII—VII, but without the lining of the cap.

When bone 81 and soft tissue 82 have healed to at least some degree, healing cap 85 is removed from support 21 and forms the device 91 serving as a dental prosthesis visible in FIG. 6 and partially in FIG. 7. This can be done without further surgery and with no further incisions into the soft tissue, so that the dental prosthesis is created and attached in a one-phase operation, namely with a single surgical procedure. Device 91 also has a superstructure element 93 on support 21. This is cap-shaped and has an originally separate cap 101 that is generally rotationally symmetrical with respect to axis 22. The cap has an axial stepped through-hole forming the interior 103 of the cap. The lowest conical section of the latter forms a conical supporting surface 104 that, when device 91 is joined to axis 22, forms the same angle as shoulder surface 37, rests continuously without gaps on shoulder surface 37 around axis 22, and thus centers the cap coaxially on axis 22. A positioning section 105 connects the conical interior section of cap 101. This section is generally cylindrical, but according to FIG. 7 has positioning projections 106 and positioning interstices 108 alternating along the periphery of interior 103. Thus there are twelve projections 106 with identical shapes and dimensions and twelve interstices 108 with identical shapes and dimensions distributed uniformly along the inner circumference. Cap 101 is thus formed for multipositioning and can be positioned in twelve different positions, i.e. rotational positions, when it is connected to the support, the angle between the adjacent rotational positions being 30°. Projections 106 consist of straight, axial ribs and have a top and two lateral surfaces. Interstices 108 accordingly consist of straight axial grooves, are approximately U-shaped in cross section, and have a bottom surface and two lateral surfaces. Interior 103 has a taper above positioning section 105 and a supporting surface 109 on the upper side of the latter that widens conically upward. Cap 101 is attached with an occlusal screw 121 to the secondary part when connected with support 21. Screw 121 has a countersunk head disposed in hole 103 of cap 101, resting on conical supporting surface 109, and a threaded part with an external thread screwed into internal thread 72 of the secondary part. Cap 101 consists for example of a metal material such as a gold alloy or titanium.

Figure 8:
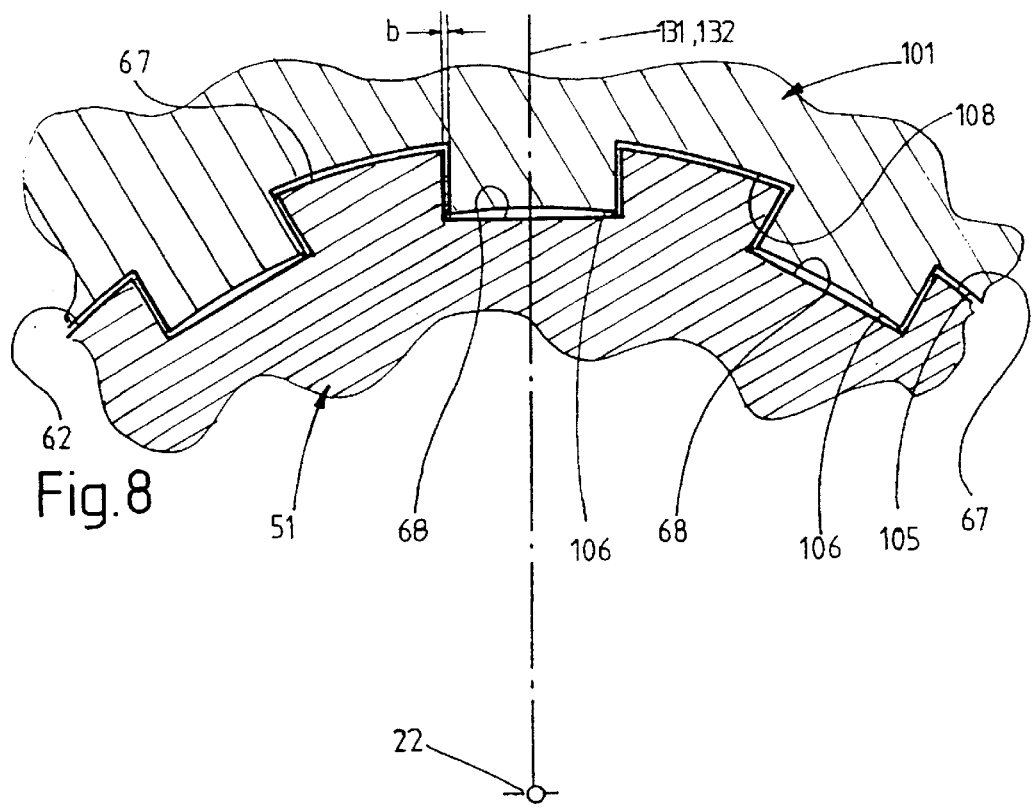
FIG. 8 shows a section from FIG. 7 on a larger scale, with the cap resting on the support in the central desired rotational position.
Figure 9:
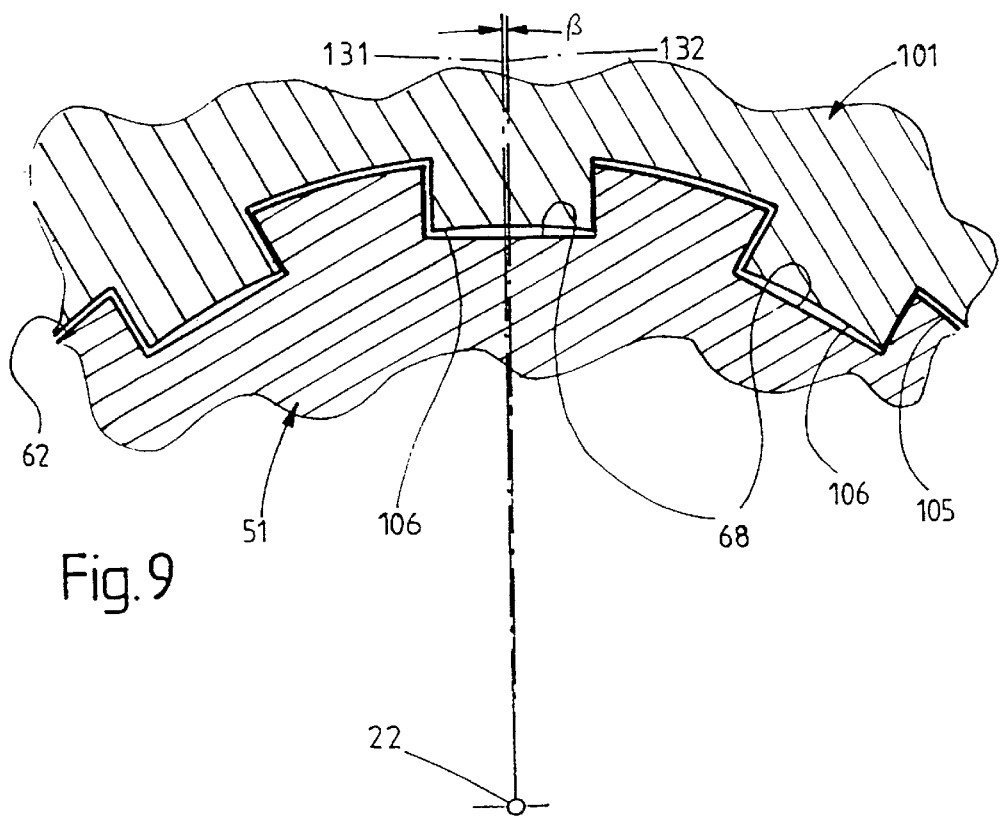
FIG. 9 shows a section similar to FIG. 8, but with the cap rotated out of its position shown in FIG. 8.

Superstructure element 93 can have a metal casting 125 cast on the cap and a lining 126 of porcelain or plastic and serve as a crown for forming an artifical single tooth or a bridge. The lower end section of the external surface of cap 101 connects to the external surface of implant 31 at edge 38 of the implant shoulder seamlessly, without steps, and preferably at least approximately smoothly and continuously. The external surface of casting 125 and/or lining 126 for its part connects for example seamlessly, without steps, and preferably at least approximately smoothly and continuously to the lower end section of the cap external surface. The cooperation of positioning sections 62 and 105 of secondary part 51 and cap 101 will now be described in greater detail. Ten of the twelve positioning projections 106 of cap 101 project with limited lateral play and limited radial play into a first, narrow positioning interstice 68. The other two projections project with limited radial play into the second, wider positioning interstice 69 of secondary part 51 in such a way that one lateral surface of each of these projections with limited lateral play faces a lateral surface of the second, wider interstice 69. FIGS. 8 and 9 show a straight line 131 that runs radially to axis 22 of the support through the middle of a first interstice 68 of secondary part 51. In FIG. 8, cap 101 is in the central desired rotational position with respect to rotations about axis 22 of the support. In this position, each of projections 106 of the cap that project into a first interstice 68 of the secondary part is located in the middle between the two lateral surfaces of the interstice 68 in question so that one straight line 132 that passes through the middle of projection 106 and is radial to axis 22 coincides with straight line 131. Because of the play, each lateral surface of an interstice 68 of the secondary part is at a distance b from the lateral surface opposite to it of a projection 106. If the positioning sections of the secondary part and the cap engage each other when the cap is connected to the support, the cap can be rotated in either direction through an angle marked b in FIG. 9, starting from its central desired rotational position shown in FIG. 8, until the screw is tight, and until the projections 106 of cap 101 projecting into the first interstices 68 of secondary part 51 according to FIG. 9 have one lateral surface in contact with one lateral surface of an interstice 68. The circumference of a circle abutting the top of projections 67 or running through them is approximately 10 mm for example. The distance b is approximately 0.01 mm for example so that a projection 106 projecting into a first interstice 68 has a total play measured tangentially to this circle of approximately 0.02 mm. Angle b is then approximately 0.36° so that the cap can be turned in either direction through an angle 2b of approximately 0.72°. The radial play between positioning sections 62 and 105 of the secondary part or the cap, namely the distance between the opposing bottom surfaces of the positioning interstices and top surfaces of the positioning projections, is approximately 0.01 mm for example.

The positioning sections that engage each other provide exact positioning and secure the cap against rotations relative to the support. If one disregards the play, the positioning projections 106 of the cap are located approximately from the bottom quarter of the head 59 of the secondary part up to its upper end at the bottom surfaces and the lateral surfaces of the positioning interstices of the secondary part of the head. Also, once again disregarding the play, the cap abuts the tops of the positioning projections of the secondary part. Since the cap also abuts implant shoulder 35 tightly and without play, it is guided laterally so that large forces, i.e. forces directed approximately transversely to axis 22 and torques or torsional stresses created by such forces, are properly transmitted from the cap to the support without the cap tilting. When screw 121 has been tightened, the cap is thus connected in a stable matter with the support. Implant shoulder 35 and the supporting surface 104 of the cap are located below the ridge of the soft tissue 82 inside the latter and can thus contact each other without a gap, averting problems with microorganisms.

Figure 10:
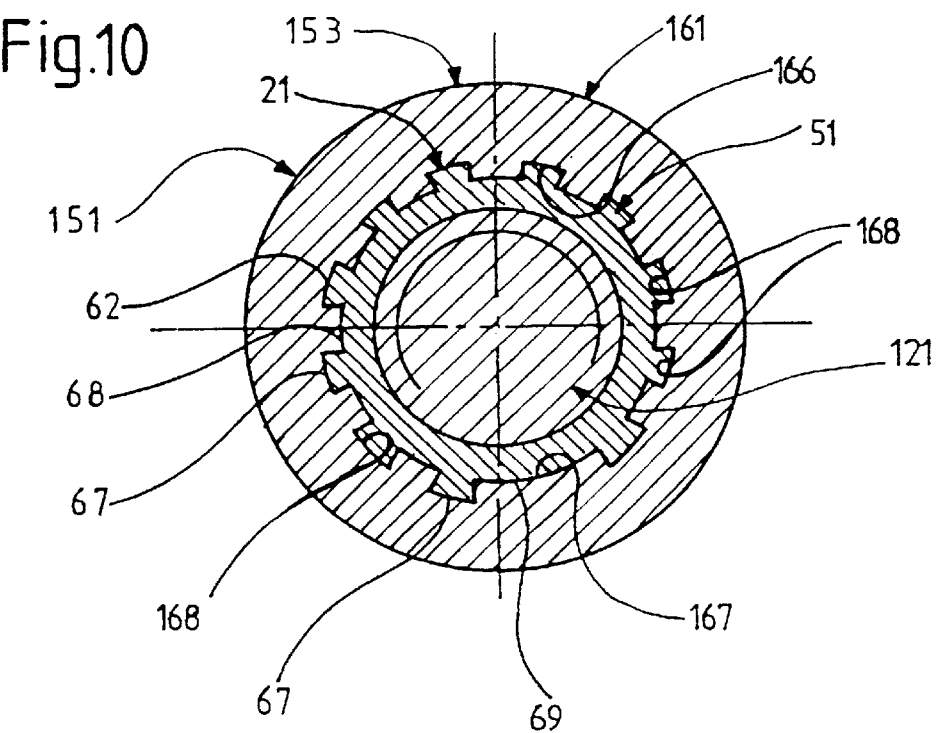
FIG. 10 shows a cross section similar to FIG. 7 through a device with a cap for single positioning.

Device 151 shown partially in FIG. 10 has a support with the same shape as the support shown in FIGS. 3 to 9 and likewise designated 21, of which only the positioning section 62 of secondary part 51 can be seen. Device 151 also has a superstructure element 153 with a cap 161. This is designed for single positioning and has a positioning section 165 with ten first, narrow identically shaped and sized positioning projections 166, a second, wider positioning projection 167, and positioning interstices 168. First positioning projections 166 are shaped similarly to positioning projections 106 of cap 101 and project into the first interstices 68 of the secondary part. The second, wider projection 167 of the cap projects with limited play into the second, wider interstice 69 of the secondary part. Cap 161, similarly to cap 101, is removably attached to secondary part 51 with an occlusal screw 121.

Figure 11:
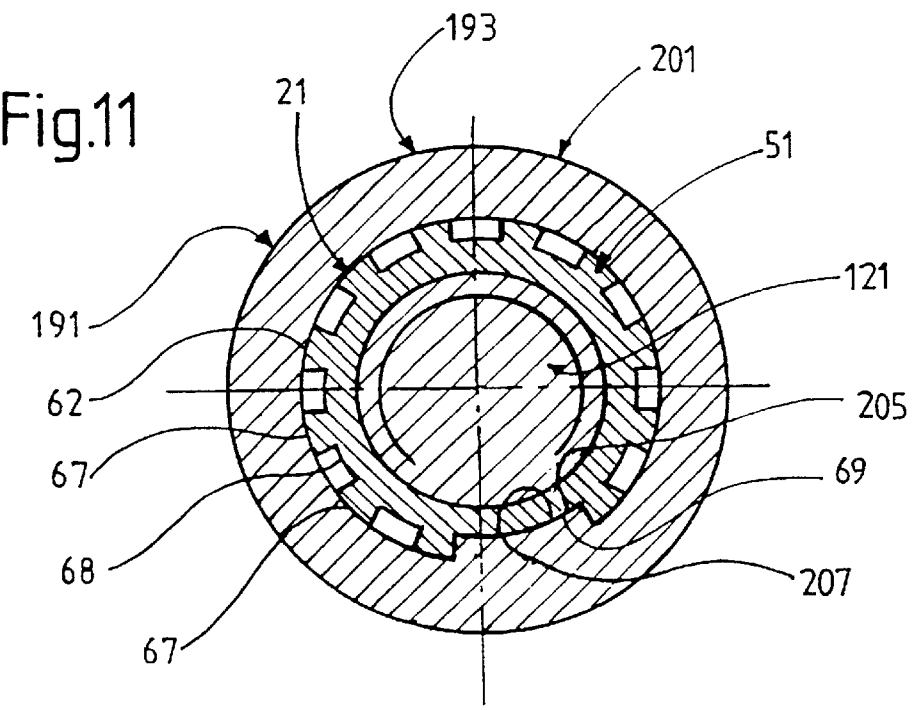
FIG. 11 shows a cross section similar to FIG. 7 through a device with another cap for single positioning.

Device 191 shown in part in FIG. 11 also has a support 21 of which only positioning section 62 of secondary part 51 can be seen. Device 191 also has a superstructure element 193 with a cap 201, which is attached with an occlusal screw 121 to the secondary part. Cap 201 has a positioning section 205. The latter is designed for single positioning and has only a single, wide positioning projection 207, which fits into the second, wider interstice 69 with limited play. Cap 201 thus has no projections fitting into the first, narrow interstices 68.

The superstructure elements 153 and 193 shown in FIGS. 10 and 11 respectively can be designed for example as so-called telescoping or soldered-base superstructures. Unless stated to the contrary above, devices 151 and 191 can be designed similarly to the device 91 described in relation to FIGS. 6 to 9.

Figure 12:
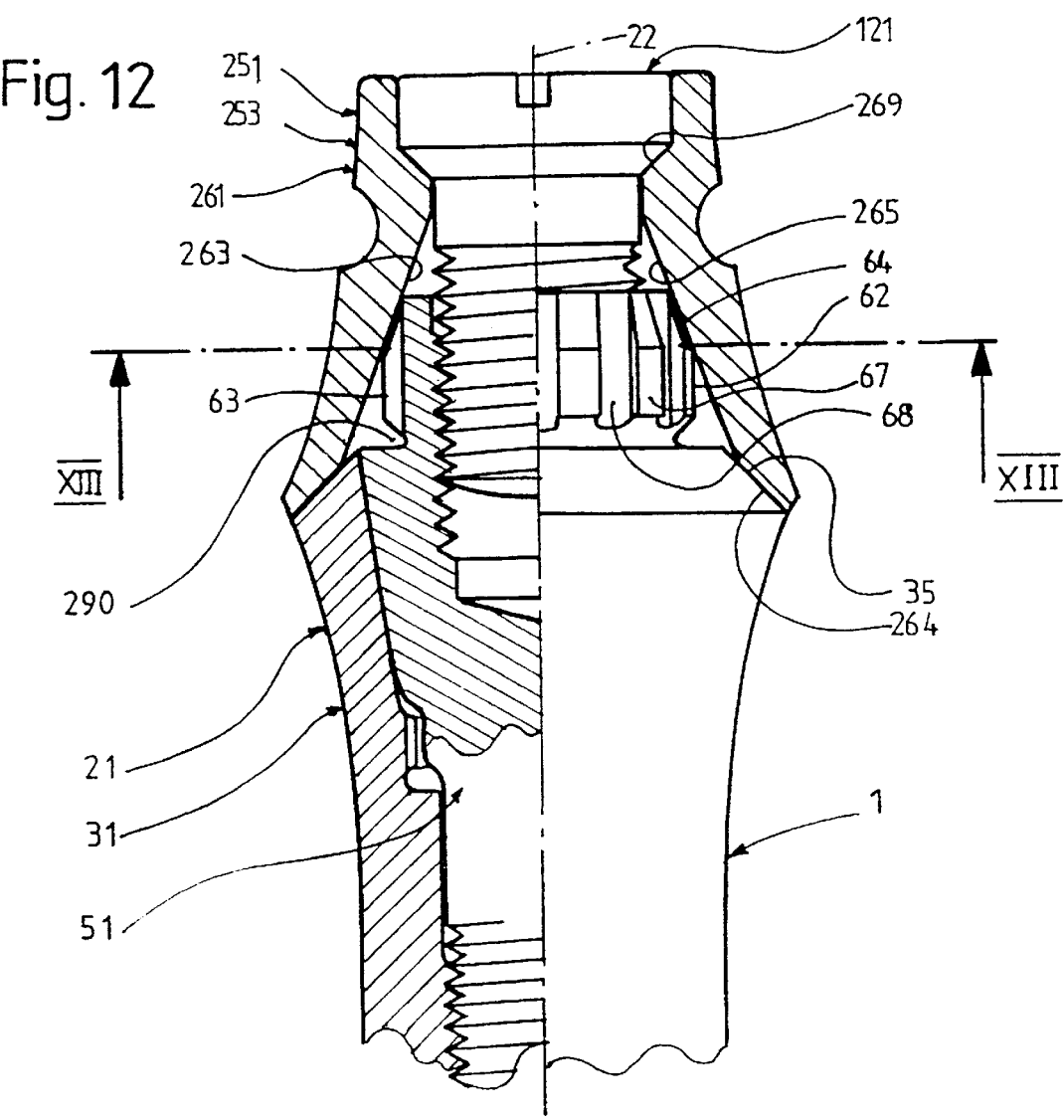
FIG. 12 shows a representation similar to FIG. 6 of a device with a cap without a positioning section.
Figure 13:
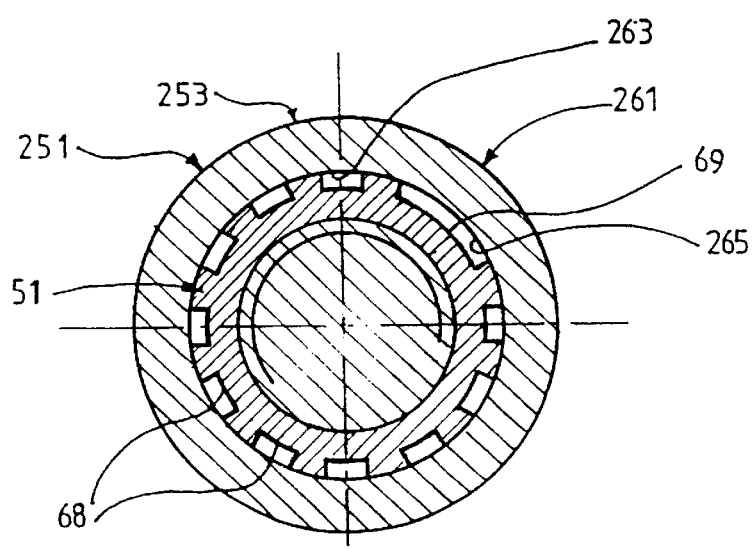
FIG. 13 shows a cross section through the device according to FIG. 12 along line XIII—XIII.

Device 251 shown in FIGS. 12 and 13 in turn has a support 21 formed as already described with an implant 31 and a secondary part 51. Device 251 also has a superstructure element 253 with a cap 261. The latter has an interior space 263 formed of an axial through-hole and at the very bottom forms a conical supporting surface 264. This is abutted by a likewise conical but steeper internal surface 265 that forms the same angle with axis 22 as conical section 64 of the secondary part. Above conical surface 265, interior space 263 has a constriction and on the top side of the latter has a conical supporting surface 269. Cap 261 is attached to secondary part 51 similarly to cap 101 by an occlusal screw 121 whose head rests on supporting surface 269. Cap 261 is designed such that in the tightened state its supporting surface 264 abuts at least the outer region of shoulder surface 37 tightly and without a gap, while between the conical section 64 of the secondary part and the conical internal surface 265 of the cap a very small gap with a width of for example approximately 0.01 to 0.02 mm is present. The cap is then likewise guided by the conical section 64 of the secondary part, centered, and supported against the influence of lateral forces acting approximately transversely to axis 22. As can be seen particularly clearly in FIG. 13, cap 261 has no projections projecting into positioning interstices 68, 69 of the secondary part and is thus not positioned with respect to rotations about axis 22. Superstructure element 253 having cap 261 can be designed for example as a rib or bridge for forming several artificial teeth and can have at least one other cap that can also be attached to a support.

Figure 14:
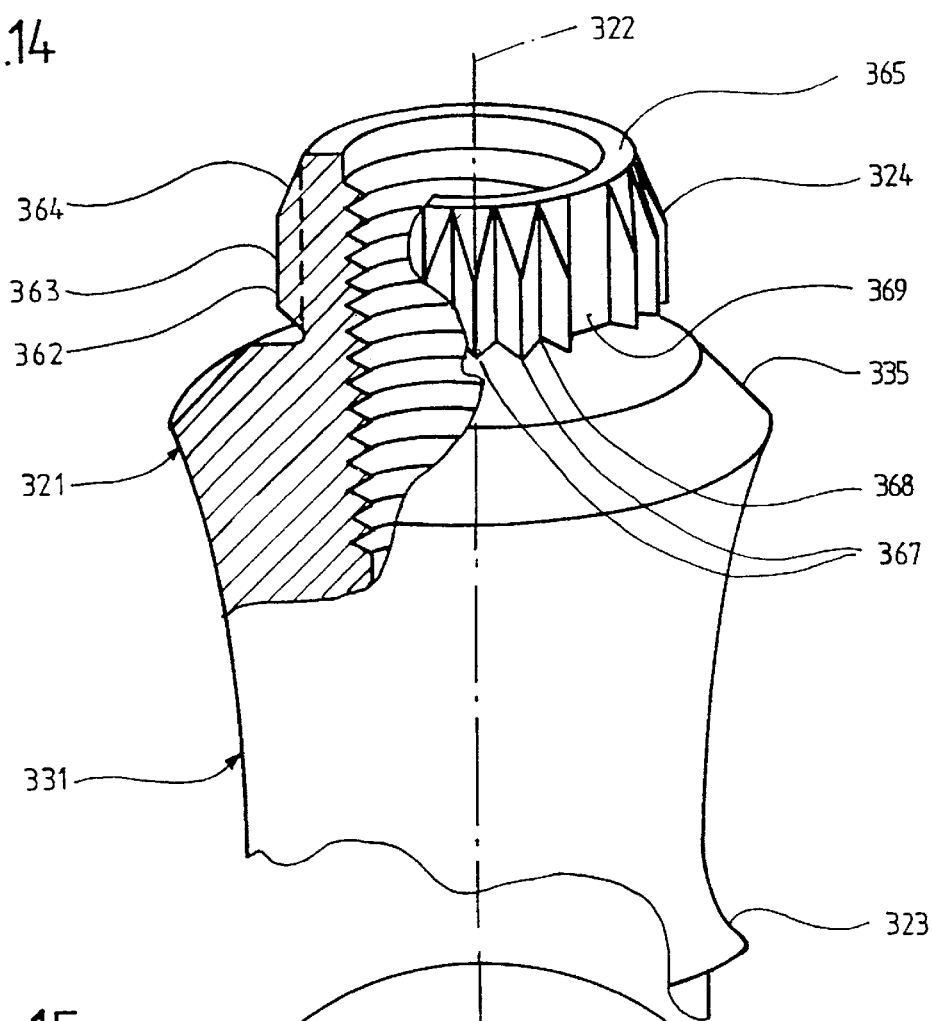
FIG. 14 shows a diagonal view of another support.
Figure 15:
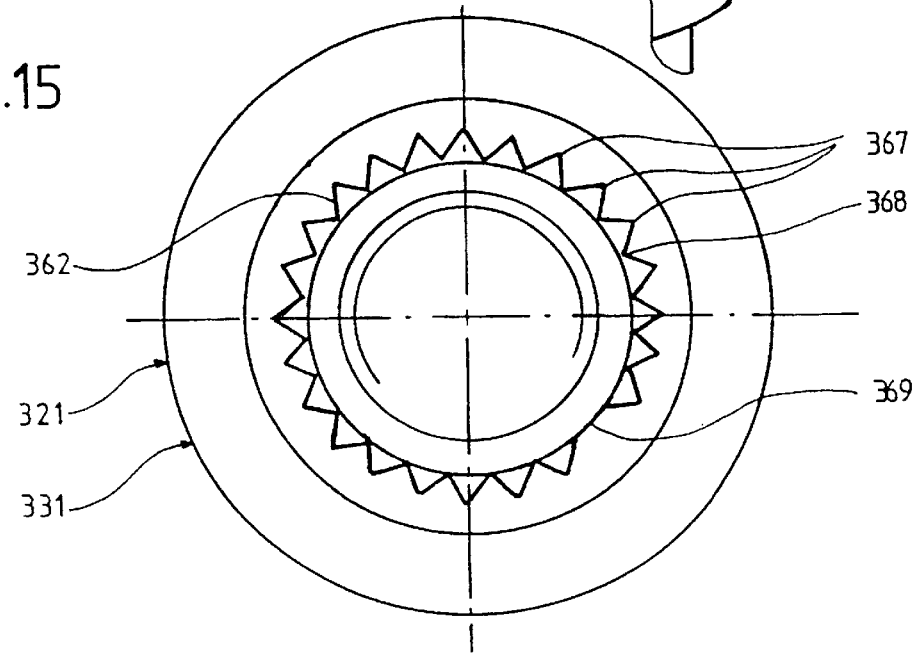
FIG. 15 shows a top view of the head part of the support according to FIG. 14.

Support 321 shown in FIGS. 14 and 15 is generally rotational symmetrical about an axis 322 and has an anchoring part 323 and a head part 324. Support 321 consists solely and completely of a one-piece body, i.e. an implant 331, whose lower part forms anchoring part 323 and whose upper part forms the head part 324 of the support. The lower part of implant 331 is shaped similarly to implant 31 and in particular has a conical implant shoulder 335 with a conical shoulder surface. The upper part of implant 331 forming head part 334 has a positioning section 362 with a lower generally cylindrical section 363 and an upper, generally conical, section 364. The latter is abutted at the upper end of the implant by an annular, flat face 365. Positioning section 362 has positioning projections 367 and positioning interstices 368, 369 alternating along the periphery. Positioning projections 367 all have the same shape, straight and parallel to axis 322, and project outwardly away therefrom; their cross sections taper in the outward direction toward their tops, and they are approximately V-shaped or triangular in cross section. The positioning interstices are also straight and parallel to axis 322 and have several narrow, first positioning interstices 368 that have the same shapes and sizes and a single wider, second positioning interstice 369. Each first positioning interstice 368 consists of a groove or notch having an approximately V-shaped cross section and has two essentially flat, lateral surfaces sloping away from their bottoms and from axis 2, and therefore outward and away from one another. The wider, second positioning interstice 369 has a flat or slightly curved bottom surface and two lateral surfaces sloping outwardly from the bottom surface and hence away from one another. The projections have tops formed by cylindrical section 363 and bevels formed by conical section 364. The tops of projections 367 define a partial circle and lie on a cylindrical surface. The bottoms of the interstices together also define a cylindrical surface. The narrow, first positioning interstices 368 adjacent to each other are all at the same distance from each other and define a circle with divisions of 15° or 24° for example. The wider, second positioning interstice 369 is formed by omitting one projection 367. Implant 331 has an axial blind hole 371 (corresponding to blind hole 71 of secondary part 51) with an internal thread 372 for screwing in an occlusal screw. Unless stated to the contrary above, support 321 consisting of implant 331 can be made the same as or similar to support 21 and used similarly thereto.

Figure 16:
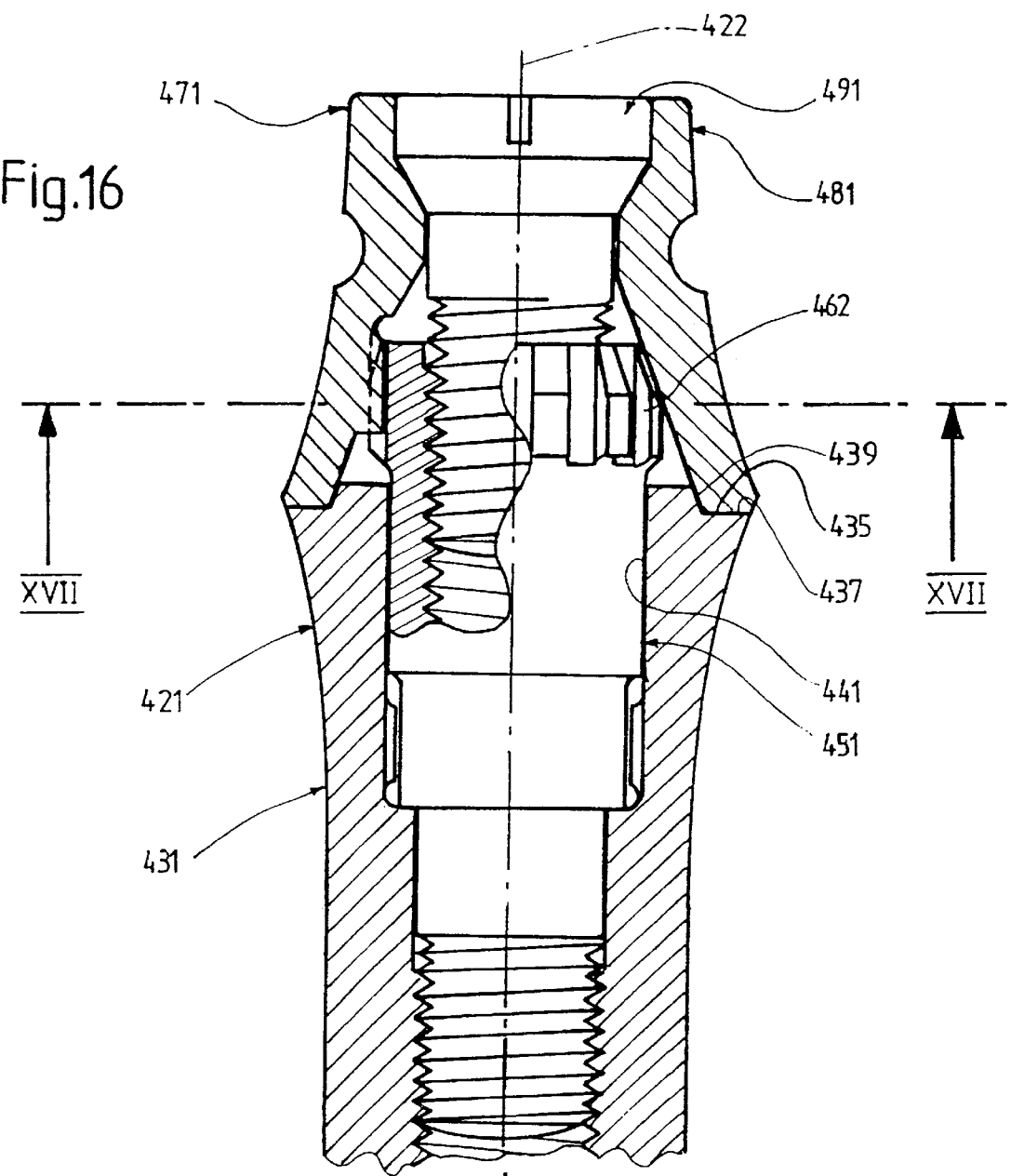
FIG. 16 shows an axial section through a variant of a device with yet another support, in which one half of a cap designed for multipositioning and one half of a cap without a positioning section is shown.
Figure 17:
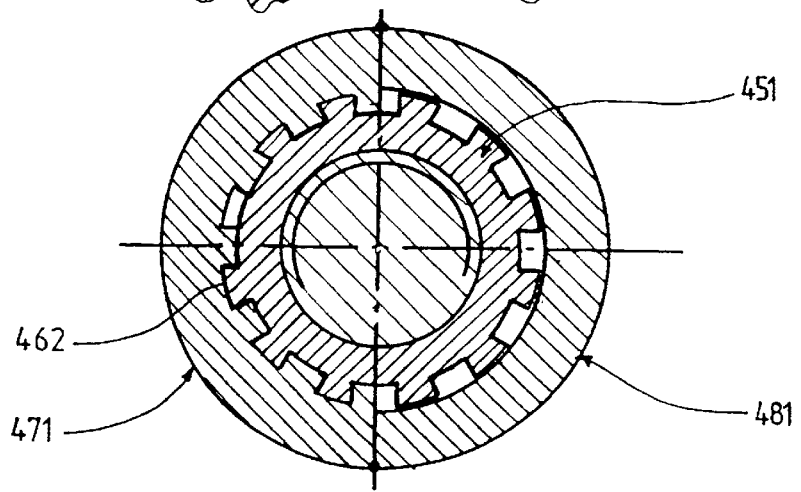
FIG. 17 shows a section along line XVII—XVII in FIG. 16 through the support and the cap halves according to FIG. 16.

Support 421 shown in FIGS. 16 and 17 has an axis 422 and an implant 431. The implant has an annular stepped face at its upper end with an implant shoulder 435 that consists of a hollow with a flat shoulder surface 437 at right angles to axis 422 and a short, conical centering surface 439 inclined upward toward the axis. Implant 434 has an axial blind hole 441 with an internal thread into which a secondary part 451 is screwed. The head of the latter has a positioning section 462 that for example is formed similarly to positioning section 62 of secondary part 51. A cap 471 drawn cut in half or a cap 481 drawn cut in half can be removably attached to support 421 with an occlusal screw 491. Cap 471 shown on the left in FIGS. 16 and 17 has a positioning section that is formed for example like positioning section 105 of cap 101 for multipositioning. The cap 481 shown on the right in FIGS. 16 and 17 does not have a positioning section so that it can be attached in any rotational position on the support analogously to cap 261.

Figure 18:
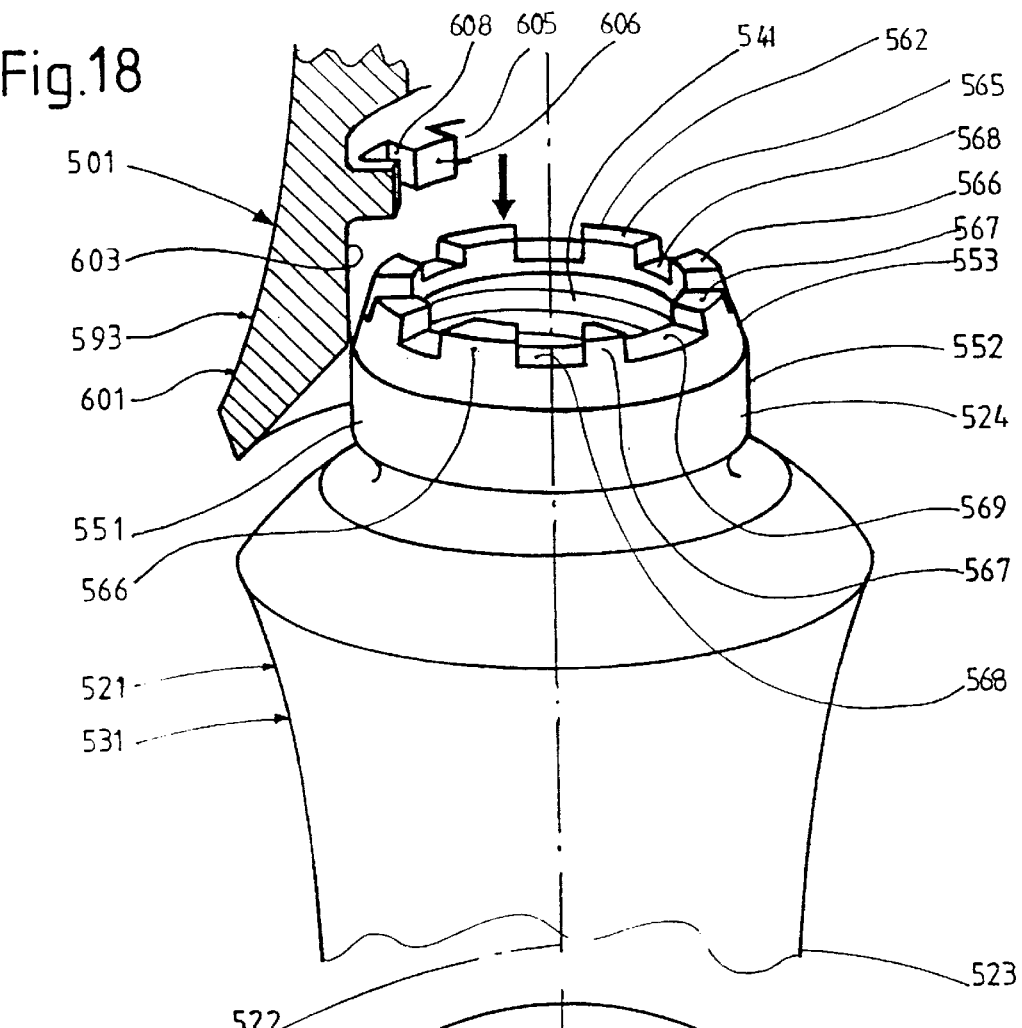
FIG. 18 shows a diagonal view of a device with yet another support and of a cap separated from this support.
Figure 19:
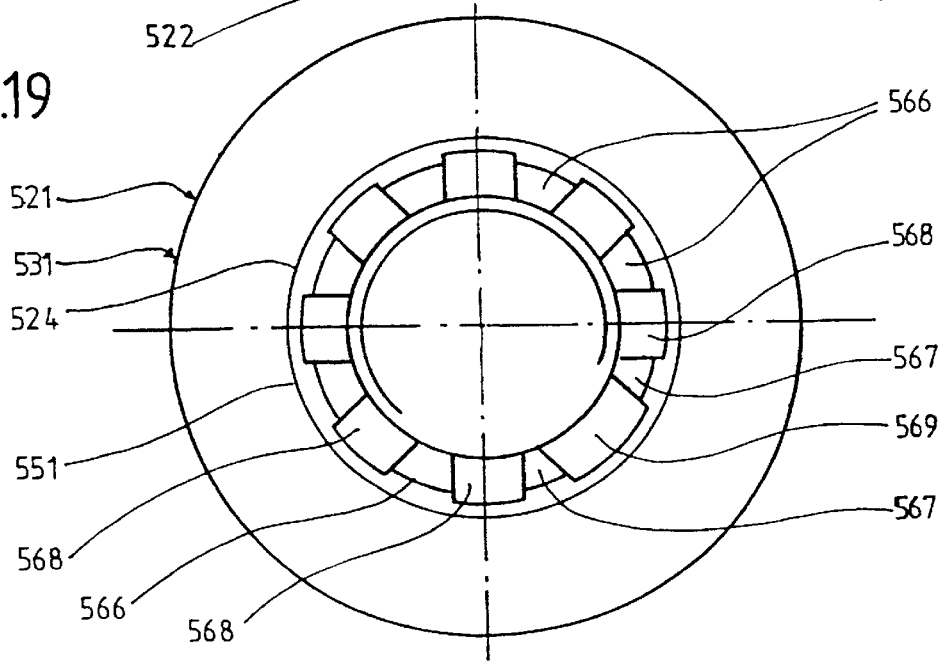
FIG. 19 shows a top view of the head part of the support according to FIG. 18.
Figure 20:
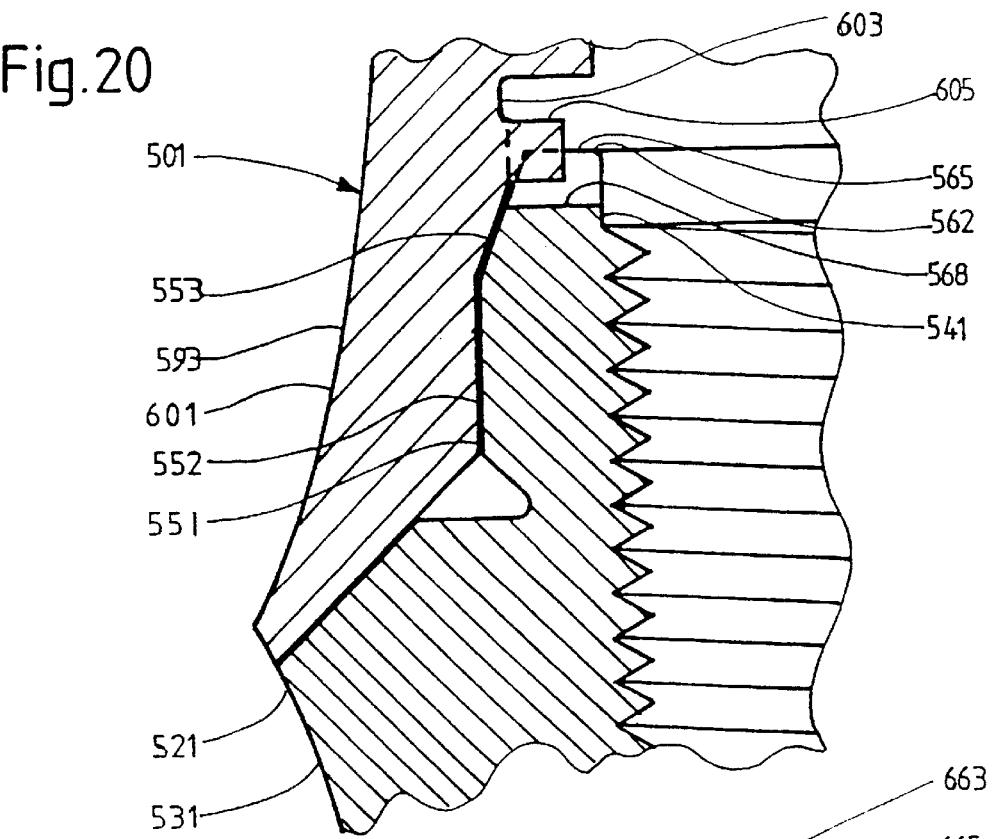
FIG. 20 shows an axial section through the device according to FIG. 18, with the cap resting on the support.

Device 501 shown in FIGS. 18, 19, and 20 has a support 521 with an axis 522. Support 521 has an anchoring part 523 and a head part 524 and consists for example exclusively of a one-piece implant 531. The latter has an axial blind hole 541 that ends in the face at the free end of head part 524. 10 The implant has a head 551 with a cylindrical section 552 and a generally conical section 553 that tapers toward the free end of the head. The head also has a positioning section 562 that is located at the thinner end of conical section 553 and on the face of the head. Positioning section 562 is delimited externally by the end section of the conical external surface of conical section 553, internally by a cylindrical section of hole 541, and on the face of the head part by an annular, flat face 565 at right angles to axis 522.

Positioning section 562 has positioning projections 566, 567 and positioning interstices 568, 569 distributed in alternating fashion around axis 522. Projections 566, 567 consist of cams that project away in the axial direction from the bottom surfaces of interstices 568, 569 and have tops formed by sections of flat face 565. The bottom surfaces of interstices 568, 569 consist of sections of a flat annular surface at right angles to axis 522. The lateral surfaces of the projections and interstices are for example flat and parallel to a plane running through the axis and the center of the interstice in question. The projections have several identically formed and dimensioned wide first projections 566 and two narrower, second projections 567 that are adjacent to each other. The interstices have several identically formed and dimensioned narrow first interstices 568 and a wider, second interstice 569 that is located between the two narrower, second projections 567. Positioning section 562 has for example a total of eight projections and interstices defining an 80 or 45° division. Device 501 also has a superstructure element 593 of which only part of cap 601 is shown in FIGS. 18 and 20. This cap has an interior space 603 with a positioning section 605. The latter has eight positioning projections 606- distributed around its periphery and, between them, eight positioning interstices 608. The positioning interstices consist for example of cams that project inward away from a stepped cylindrical internal surface in the radial direction and, when device 501 is assembled, fit into the interstices 566, 567 of support 521. However, instead of projecting from above, for example away from a flat radial plane, the positioning projections could project downward in the axial direction. Moreover, positioning section 605 of cap 601 can be shaped either for multipositioning or for single positioning. Device 501 can accordingly, unless stated to the contrary above, be designed similarly to device 91 or 151.

Figure 21:
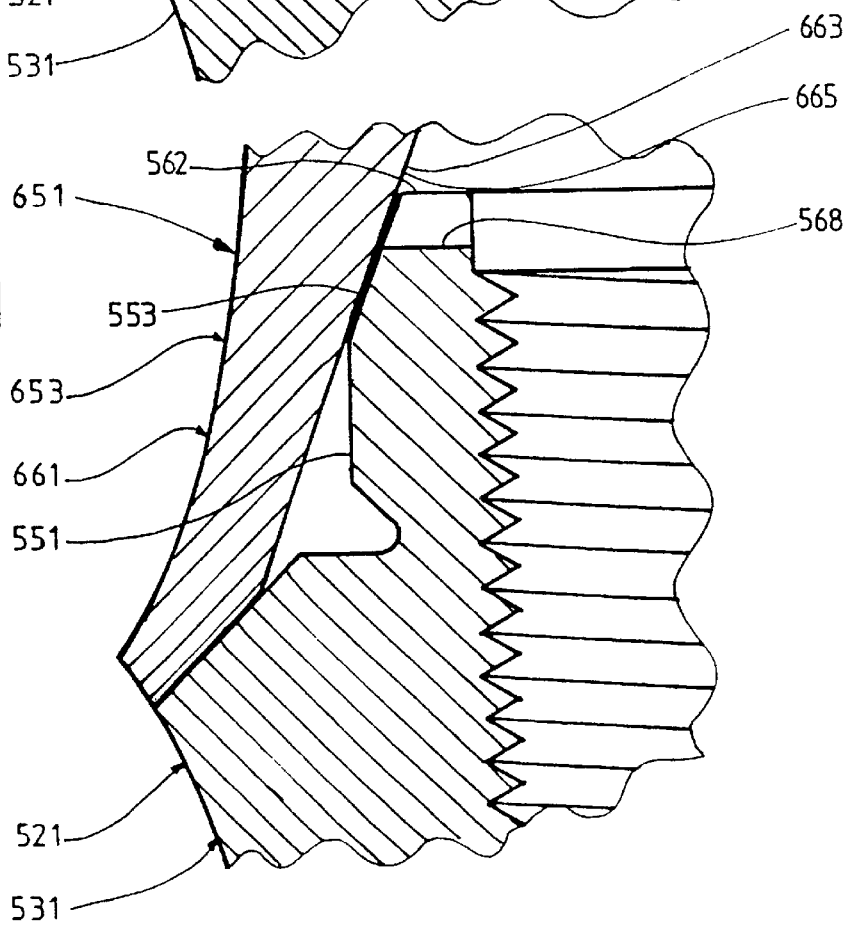
FIG. 21 shows an axial section through a device with a support according to FIGS. 18 to 20, but with a cap having no positioning section.

Device 651 shown in FIG. 21 has a support 521 formed in the same way as in FIGS. 18 to 20 and, like the latter, consisting of an implant 531. Device 651 has a superstructure element 653 of which once again only cap 661 is depicted. This does not have projections fitting into positioning interstices 568 of the support or implant, but an interior space 663 with a conical internal surface 665 guided with limited play by conical section 553 of head 551 of implant 431. Unless otherwise described above, device 651 can be formed similarly to device 251 shown in FIGS. 12 and 13.

Figure 22:
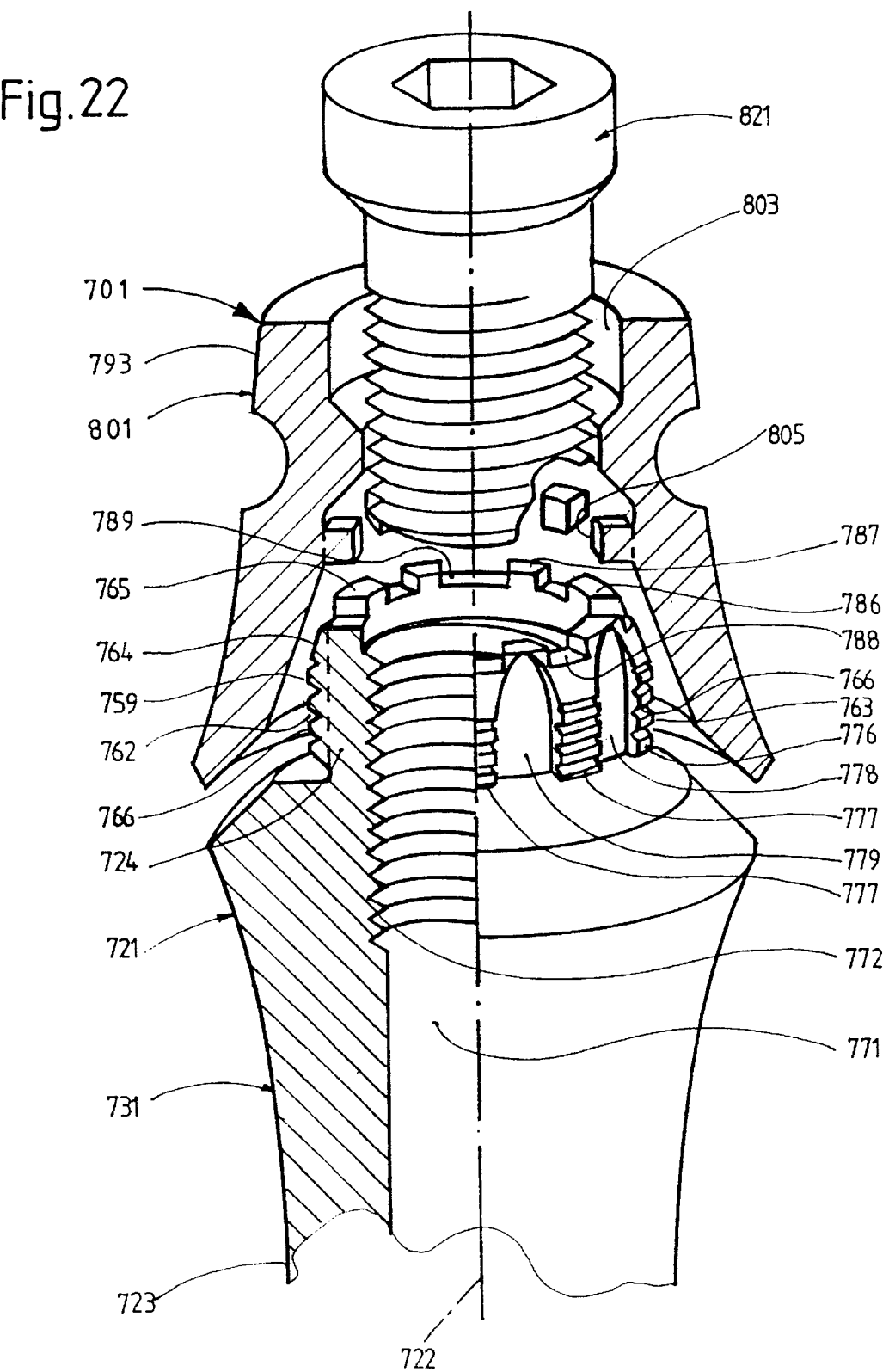
FIG. 22 shows an exploded view of another device.

Device 701 shown in FIG. 22 has a support 721 with an axis 722, an anchoring part 723, and a head part 724. Support 721 has an implant 731 consisting of a one-piece metal body. Implant 731 has a head 759 with a positioning section 762. The latter has a generally cylindrical section 763, a generally conical section 764 tapering upward away from the latter, and an annular, radial, flat face 765. Cylindrical section 763 is provided with an external thread 766 that is formed for example as a trapezoidal thread and has a top formed of sections of a cylindrical surface. Support 721 also has an axial blind hole 771 with an internal thread 772, said hole terminating in the face of the head part. The partly cylindrical and partly conical external or peripheral surfaces of positioning section 762 are provided with axially extending and radially outwardly projecting positioning projections 776, 777 and positioning interstices 778, 779, with for example several first, wide projections 776, two second narrower projections 777, several first, narrow interstices 778 and one second, wider interstice 779 disposed between the two narrower projections being present. The interstices formed by grooves divide external thread 766 so that only sections of the external thread are present on the tops of the projections. Positioning section 762 is additionally provided on the face with axially projecting positioning projections 786, 787 and positioning interstices 788, 789, with for example, analogously to the case of support 521, several first, wide projections 786, two second, narrower projections 787, several first, narrow interstices 788, and one second, wider interstice 789 being present. Device 701 also has a superstructure element 793 with a cap 801. The cap has an interior space 803 with a positioning section 805 formed similarly to that of cap 601 as well as projections that can fit into endwise interstices 788, 789 of the support. Cap 801 can be attached to support 621 with an occlusal screw 821.

Cap 801 can be replaced by a cap with positioning projections that fit into the interstices 788, 769 of support 721 on the external or peripheral surface. Also, support 721 can have attached to it a cap that does not have positioning projections but has an internal thread screwed to the external thread 766 of the support when the cap is attached.

Figure 23:
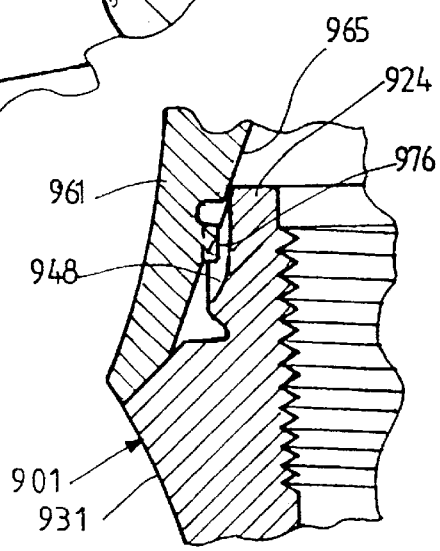
FIG. 23 shows an axial section through another device.

Device 901 shown in FIG. 23 has a support formed of a one-piece implant 931. Head part 924 of the support, formed by the head of the implant, has first and second positioning interstices, of which one of the first is visible and designated 948. This extends from the bottom half of the generally cylindrical head section to the thinner, top end of the generally conical head section and is milled thereinto for example with a disk mill such that its bottom runs out at the bottom end into the cylindrical external and/or jacket surface of the cylindrical head section.

Cap 961 belonging to device 901 is formed partially similarly to cap 661 shown in FIG. 21 and, like the latter, has a generally conical internal surface designated 965 in FIG. 23. Cap 961 shown in FIG. 23 is however formed for multipositioning or single positioning and has positioning projections of which one is shown, designated 976, which projects into positioning interstice 948.

The axial dimension of each positioning projection is considerably smaller than the total axial dimension of the cylindrical and the conical head sections, amounting to at most 30% of the total axial dimension of these two head sections and of course of the head as a whole. The positioning projections are thus at a distance from the bottom end of the cylindrical head section and from the top end of the conical head section 17 and are approximately at the level at which the two head sections are connected together. Between the top of projection 976 and the bottom of positioning interstice 847 containing the latter is an open gap or interstice whose radial dimension at the lowest point of the interstice is for example at least the same as half the depth of interstice 948. The lateral surfaces of the positioning projection are at most separated by very narrow gaps from the lateral surfaces of the interstice. The positioning projections thus have very limited play in interstice 948 along a circle concentric with the axis of the support and tangential thereto. The cap is therefore well supported laterally, i.e. against forces directed approximately transversely to the axis, by conical internal surface 965 and the lateral surfaces of projections 976, although there is a relatively large gap between the tops of projections 976 and the bottoms of interstices 948.

Figure 24:
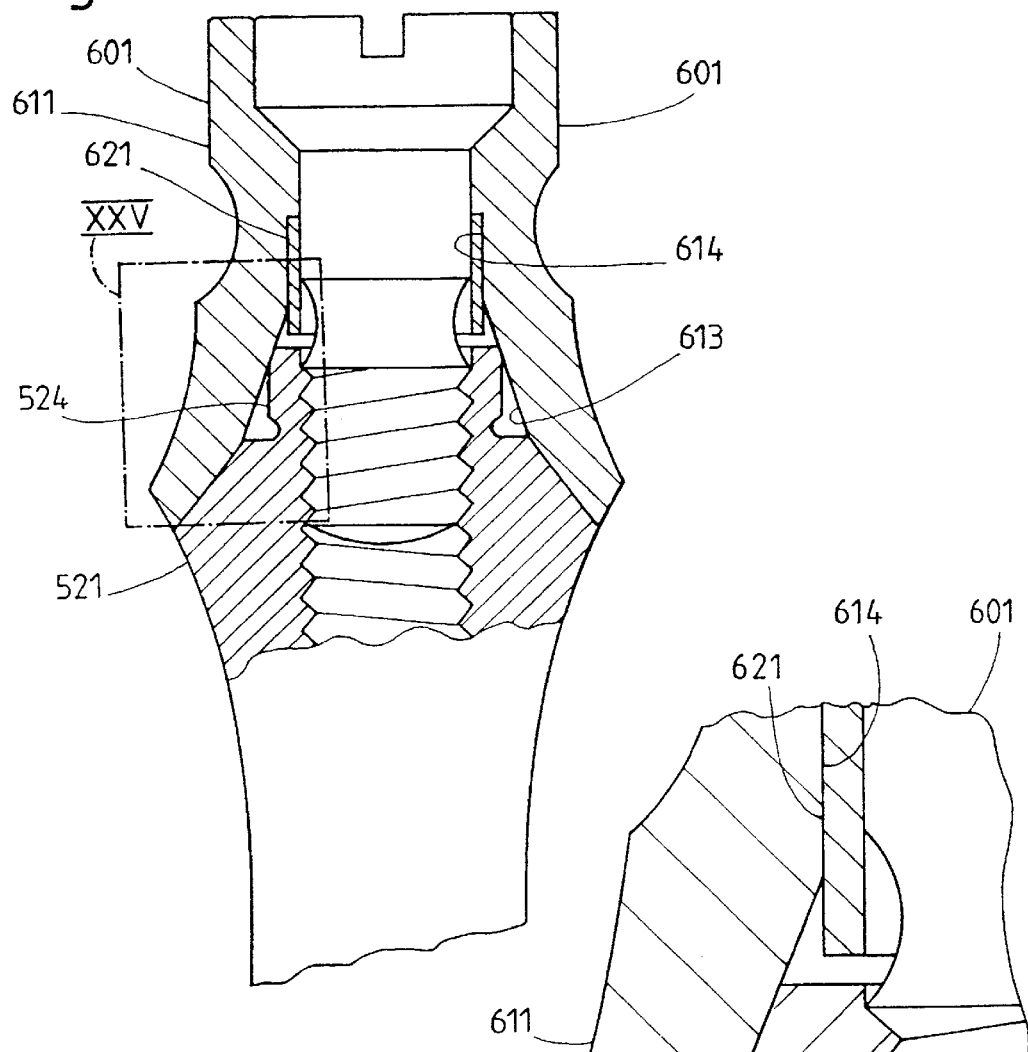
FIG. 24 shows an axial section through parts of another device.
Figure 25:
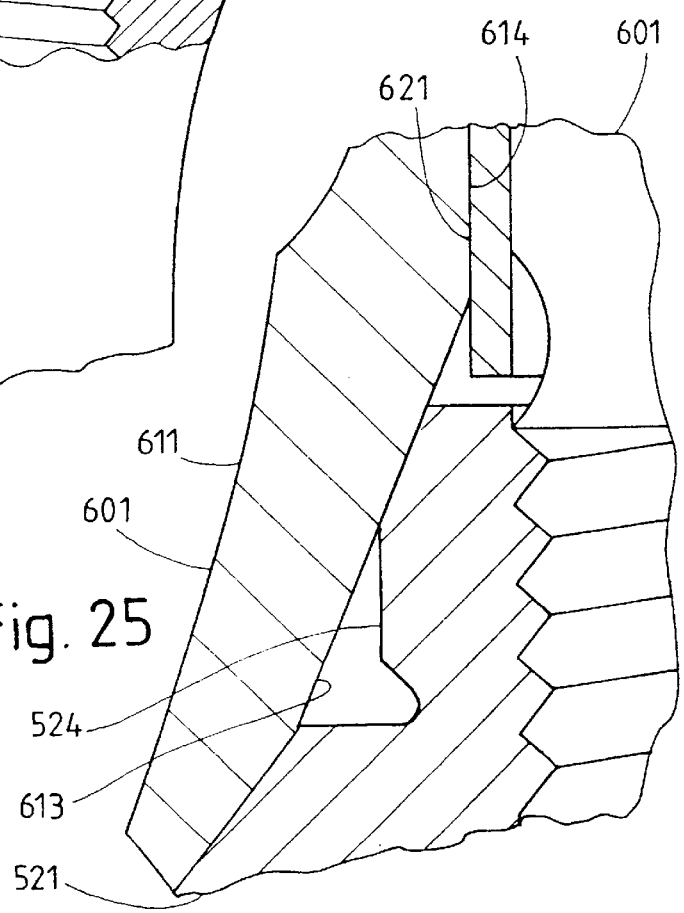
FIG. 25 shows a section designated XXV in FIG. 24 of the device according to FIG. 24 on a larger scale.

The device shown in part in FIGS. 24, 25, 26, 27, and 28 has a support similar to the support shown in FIGS. 18 to 21 and is likewise designated 521. The support 521 shown in FIGS. 24 to 26 has in particular, disposed on the face of head part 524, first positioning interstices 568 and a second positioning interstice 569. In the head part 524 shown in FIGS. 24 to 26, however, each interstice 568, 569 is trapezoidal in a side view and in a cross section running perpendicularly to its radial lengthwise direction and has a flat bottom surface 571 at right angles to the axis and two flat, lateral surfaces 572. The latter two slope away from each other upwardly from bottom surface 571 so that the interstices expand in the direction away from the bottom surface. Cap 601 shown in FIGS. 24 and 25 is partially formed similarly to the cap with the same number shown in FIGS. 18 and 20 but originally consists of two separate parts, namely a metal, sleeve-shaped main body 611 and a positioning sleeve 621. Main body 611 has an axial through-hole and at the bottom, another conical internal surface 613 as well as a cylindrical hole section 614 above the latter. Positioning sleeve 621 is essentially cylindrical and attached to main body 611, namely pressed and/or glued into cylindrical hole section 614. The positioning sleeve also has a section projecting downward from cylindrical hole section 614 with at least one positioning projection 626 that projects axially downward; according to FIG. 27 for example two or more positioning projections 626 with the same shapes are present. Each of them is trapezoidal looking in the radial direction and has a flat face at right angles to the axis and two flat, lateral surfaces sloping away from each other in the direction away from the face. Each projection 626 is sized so that, when the device according to FIG. 29 is assembled, it projects into a first interstice 568 of support 521 with very limited lateral play. Positioning sleeve 621 makes multipositioning of the cap relative to the support possible.

The positioning sleeve 621 shown in FIG. 27 can be replaced by the positioning sleeve 621 shown in part in FIG. 29. This sleeve has a positioning projection 627 which fits into the second positioning interstice 569 of support 521 shown in FIG. 26. Also, the positioning sleeve shown in FIG. 29 can have additional projections, not shown, that fit into first interstice 568 of the support.

The device shown in part in FIG. 30 has a support 521 with the same shape as the support shown in FIGS. 24, 25, 26, and 28 and has a first positioning interstices 568 at the end of the head part. The positioning sleeve shown in part in FIG. 30 has a least two positioning projections 636. Each of them has a face at right angles to the axis, two lateral surfaces parallel to the axis, and, when the face is connected to the lateral surfaces, edges 637. At least one of projections 636 projects into a first interstice 568 of support 521 when the device is assembled. The two edges 637 then abut the lateral surfaces of the interstice with extremely limited play.

The devices shown in FIGS. 23 to 30 are advantageous in particular for applications where a superstructure element or impression element having a cap can be pulled out from or placed on the support diagonally to its axis. This may be the case with two caps belonging to one bridge or the like, that have to be placed simultaneously on two implants with sharply diverging or converging axes.

In the embodiments described below, corresponding, identical, or similar parts in the various embodiments will be designated with the same reference numerals.

The support 1000 shown in FIGS. 31, 32, and 33 consists entirely of a one-piece metal implant 1001, has an axis 1003, and is essentially rotationally symmetrical therewith. Implant 1001 has an anchoring part 1005 at the bottom and a head 1007 at the top, which forms the head part of the support. The free ends of the anchoring part and the head, that face away from each other, form first end 1008 and second end 1009 of implant 1001. The first end 1008 located at the bottom the implant has a slightly convexly curved end surface in axial section. Anchoring part 1005 has, from bottom to top, a generally cylindrical section 1011 and a trumpet-shaped section 1013 expanding in the direction away from the latter, whose external surface is always flush with the external surface of the generally cylindrical section 1011. Generally cylindrical section 1011 is provided with a single-pitch right-hand external thread 1015. This thread has a more or less serrated profile and has a helical rib 1016 with a top 1017 and two flanks that are asymmetric in axial section. The lower flank located near first end 8 forms an angle of for example approximately 70° to 75° with axis 1003. The upper flank forms in axial section a smaller angle with the axis than does the lower flank. Additionally, this angle decreases with increasing distance from the top, so that the upper end of the upper flank is almost parallel to the axis. The axial dimension of helical rib 1016 is therefore—measured half-way down the thread or half-way up the rib—considerably less than the axial dimension, measured at the same radius, of the grooves between sequential turns or windings of rib 1016. The core diameter D of the thread measures at most preferably 4 mm, preferably at least 3 mm, and for example approximately 3.5 mm. The radial thread depth or height of the rib is for example approximately 0.3 mm. The pitch of the thread is for example approximately 1 mm. The external thread 1015 is formed as a normal combination thread, i.e. a non-self-cutting thread. The anchoring part has a short (approximately 1 to 2 mm long) cylindrical, smooth (i.e. threadless) end section 1018 between first end 1008 and external thread 1015; said section 1018 is continuously connected with the convex end surface at first end 1008 by means of a rounded transition and its diameter is approximately the same as the core diameter of the external thread. The diameter of the upper end of cylindrical section 1011 and the diameter at the lower end of trumpet-shaped section 1013 that contacts the upper end is the same as the core diameter of external thread 1015 so that rib 1016 of the external thread projects radially beyond the sections of the implant contacting its ends.

At the upper, wider end of trumpet-shaped section 1013 is a shoulder 1021 with a conical shoulder surface 1022 sloping upward and inward in the direction away from the first end. This surface forms an angle of 40° to 50° and for example 45° with axis 1003. A flat annular surface 1023 at right angles to axis 1003 abuts the upper, narrower end of conical shoulder surface 1022.

Head 1007 extends upward away from annular surface 1023 and has a head section 1025 essentially parallel to axis 1003 and a generally conical head section 1027 that tapers upward away from head section 1025 toward the free end of the head and hence toward the second end 1009 of the entire implant. Head section 1025 parallel to the axis is delimited from the upper end of shoulder 1021 by an annular groove curved concavely in axial section. The head has a peripheral surface 1030 and a flat, annular end surface 31 at its free end, forming the second end 1009 of the implant. Both head sections 1005, 1027 are generally rotationally symmetrical with axis 1003 and/or each have a sheathing surface rotationally symmetrical with the axis, namely cylindrical or conical. The conical sheathing surface of the generally conical head section 1027 forms an angle with axis 1003 that is smaller than the angle formed by conical shoulder surface 1022 with axis 1003 and is matched to the distance between the conical head section and the shoulder such that the prolongation of the conical surface defined by the conical head section intersects shoulder 1021 within the outer edge of conical shoulder surface 1022, namely for example intersects the inside half of shoulder surface 1022 or possibly flat annular surface 1023. The angle formed between the conical surface of the conical head section and the axis is preferably 15° to 25° and for example approximately 20°. The axial dimension or height of head 1007, measured from flat annular surface 1023 to the second end 1009 of the implant, is a maximum of 2 mm, preferably 1.2 mm to 1.8 mm, and for example approximately 1.5 mm. The axial dimensions of axially parallel head section 1025 and annular groove 1029 added together are for example approximately 1 mm. The axial dimension of the generally conical head section 1027 is for example approximately 0.5 mm.

Implant 1001 is provided with a blind hole 1035 coaxial with axis 1003. This hole has an opening 1036 located at second end 1009, surrounded by annular end face 1031, formed by a very short cylindrical hole section, and proceeding away therefrom and downward in the following order: an internal thread 1037, metric for example, a cylindrical, smooth (i.e. threadless) hole section 1038, and a bottom 1039. The lower end of internal thread 1037 further from the opening is inside the expanding trumpet-shaped section 1013 of the implant. The diameter of the cylindrical hole section 1038 is approximately the same as the core diameter of the internal thread. Bottom 1039 is inside the lower half of the generally cylindrical section 11 of anchoring part 1005, for example approximately at the lower end of the external thread, tapers to its deepest point, and is delimited by a surface, curved in axial section, that is joined continuously and smoothly with the surface of the cylindrical hole section. This shape of bottom 1039 reduces the risk of the implant breaking in the vicinity of bottom 1039.

Anchoring part 1005 is provided with at least one lengthwise groove 1051 and namely with three grooves 1051 distributed around axis 1003. Each groove 1051 is longitudinal and inclined in a radial view to axis 1003 of the groove in question relative to the axis on the same side in the same direction as the rib of the right-hand thread, namely upward to the right. The center line of a groove running in the lengthwise direction and the lateral surface sections of the groove parallel thereto form, in radial view, an acute angle with a plane at right angles to axis 1003, that is larger than the angle formed by rib 1017 with such a plane, i.e. than the pitch angle of the thread. Grooves 1051 in the vicinity of the end section of external thread 1015 located nearer to the first end 1008 of the implant, are however at a distance from first end 1008. Each groove 1051 intersects at least one turn of rib 1017 or delimits the beginning of a rib and forms a face 1053 with at least one turn of the rib 1016 which, in cross section, forms an acute angle b with a straight line running radially to axis 1003 through this axis and top 1017. Face 1053 also forms an acute lead angle of for example approximately 20° with axis 1003 at top 1017. Grooves 1051 form chip grooves, but do not extend further from the end of external thread 1015 remote from the first end 1008 of the implant so that the end of the external thread has a section between grooves 1051 and its end facing away from first end 1008, that surrounds axis 1003 without a break at least once and for example at least two or at least three times. Blind hole 1035 terminating in second end 1009 of the implant extends for example up to the lengthwise area of anchoring part 1005 that has grooves 1051. The depths of grooves 1051 are such that the grooves do not extend into blind hole 1035. Grooves 1051 can for example be milled at low cost with a disk mill into the anchoring part. The starting section of external thread 1015, serving for thread-cutting, located in the lengthwise area of grooves 1051 and intersected thereby, preferably has a maximum diameter or outside diameter that is slightly smaller, preferably at least 0.01 mm, preferably at most 0.10 mm, and for example 0.02 mm to 0.05 mm smaller than the maximum diameter or outside diameter of the section of the external thread located above grooves 1051. This has the advantage that the upper section of the external thread is firmly and securely anchored in the bone from the outset when the implant is screwed into a bone.

If a thread is cut into a bone with self-cutting external thread 1015, because of grooves 1051 only the lower flank of rib 1017 engages the bone so that only a relatively small torque is required to cut the thread. The chips of bone material produced by cutting the thread can collect in grooves 1051 and knit with the bone surrounding the anchoring part. This improves the stability of the connection between the implant and the bone.

Peripheral surface 1030 of head 1007 has axial positioning projections 1065 distributed around axis 1003 and axial positioning interstices disposed therebetween, namely several positioning interstices 1068 with the same shape and a wider and deeper positioning interstice 1069. Axial positioning interstices 1068, 1069 are groove-shaped, also designated "positioning grooves 1068, 1069" below, and form with axis 1003 non-rotationally symmetric, concavely curved positioning surfaces 1033, namely several identically shaped first positioning surfaces formed by first grooves 1068 and a wider and deeper second positioning surface. The second positioning surface has for example a circle center closer to axis 1003 and/or a larger radius of curvature than the first positioning surfaces.

Interstices 1068, 1069 and positioning surfaces 1033 formed by them—or at least the deepest area thereof in cross section—extend in turn over the entire length of head section 1025 parallel to axis 1003 and at least approximately and for example exactly up to the thinner end of conical head section 1027 and thus also up to second end 1009 of the entire implant. The section of each positioning surface 1033 located in the vicinity of the axially parallel head section 1025 forms an arc of a circle in cross section, which forms at most a semicircle so that it is smaller than a semicircle. The projections 1067 between two first interstices or grooves 1068 all have the same shapes and dimensions. The two projections next to interstice 1069 or the second groove are somewhat narrower than the remaining projections 1067. The sections of positioning surfaces 1033 located in the vicinity of the generally conical head section 1027 then form smaller arcs of a circle and extend for example up to the thinner end of the conical section in annular face 1031. The projections 1067 between the positioning grooves have external peripheral sections that form parts of a cylindrical or conical surface. Eight for example positioning grooves 1068, 1069 are present and together they define a circle divided into eight parts in which however more than eight (for example twelve or more) positioning grooves may be present.

Implant 1001 is made of titanium for example. The external surface of anchoring part 1005 is for example from first end 1008 to near shoulder 1021, namely up to approximately 1 mm to 3 mm below the upper, wider end of trumpet-shaped section 1013—rough and porous, for example by blasting with solid particles such as ceramic or sand particles, or roughened by etching or provided with a porous coating of sprayed-on titanium. On the other hand, the uppermost area of trumpet-shaped section 1013, conical shoulder surface 1022, annular surface 1023, and the various surfaces of head 1007 are smooth and pore-free.

Figure 34:
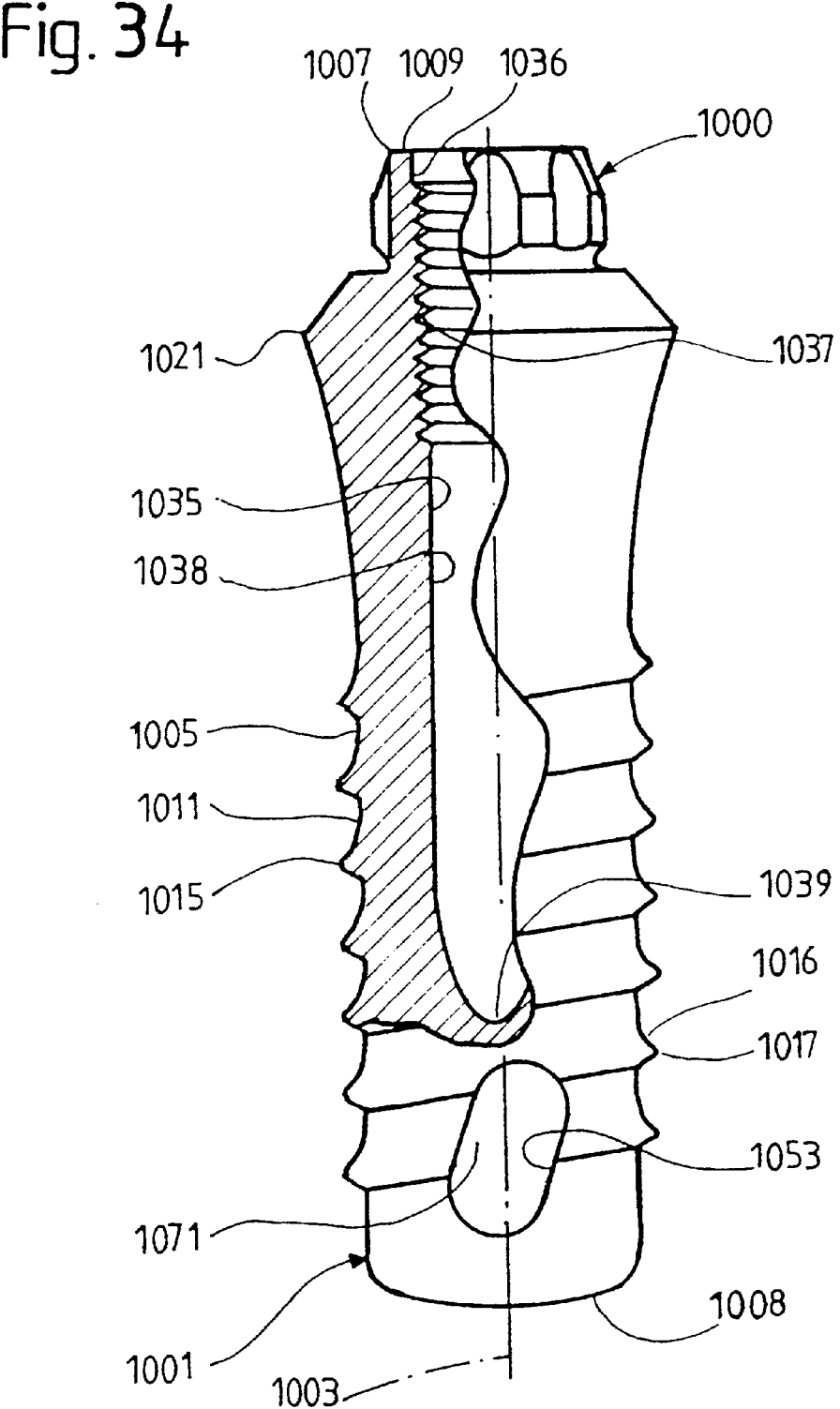
FIG. 34 shows an implant shown partially in side view and partially in axial section, whose anchoring part has grooves or holes terminating in each other.

Implant 1001 shown in FIGS. 34 to 36 has an anchoring part 1005 with a generally cylindrical section 1011. This section is provided with a self-cutting external thread 1015 and in the vicinity of its lower end with several, for example three, lengthwise grooves and/or lengthwise holes 1071 distributed around axis 1003. These serve as chip grooves and/or chip holes and are inclined as viewed in the radial direction, analogously to grooves 1051, to axis 1003 and form a lead angle therewith designated a in FIG. 35. One lateral surface of each groove and/or hole 1071 also forms a chip surface 1053. These chip surfaces in turn form, in right-angled cross sections to axis 1003, an acute chip angle b with the straight lines radial to axis 1003. Grooves and/or holes 1071 are however deeper than grooves 1051 of the implant shown in FIGS. 3 to 5, so that they intersect each other and their central bottom sections penetrate each other. Grooves and/or holes 1071 thus have, in the central cross-sectional area of anchoring part 1005, a common central hollow space and together form the passages that pass through the implant in cross section. The bone chips entering in grooves and/or holes 1071 when a thread is cut can thus, together with the bone material that grows during the subsequent healing process, form a complete penetrating framework of bone. These provide highly stable and durable anchoring of the implant in the bone even when the anchoring part is comparatively short. Cylindrical hole section 1038 of blind hole 1035 terminating in head 1007 in the second end 1009 of implant 1001 is shorter in the implant shown in FIGS. 34 to 36 than in the implant shown in FIGS. 31 to 33, so that bottom 1039 of blind hole 1035 is above grooves and/or holes 1071. Head 1007 and shoulder 1021 of the implant shown in FIGS. 34 to 36 have the same shapes as in the implant according to FIGS. 31 to 34.

In the implant 1001 shown in FIG. 37, blind hole 1035 extends up to the lengthwise section of anchoring part 1005 having grooves 1081, namely chip grooves, similarly to the case in the implant according to FIGS. 31 to 33. Grooves 1081 extend however up to the lower, first end of the implant shown in FIG. 37.

Implant 1001 shown in FIGS. 38 and 39 has once again a first end 1008 formed by anchoring part 1005 and a second end 1009 formed by head 1007. The generally cylindrical section 1011 of anchoring part 1005 is provided with an external thread 1015. Blind hole 1035 of the implant has once again an opening 1036 located at second end 1009 of the implant, and has an internal thread 1037, a cylindrical hole section 1038, and a bottom 1039 that is located above the lower end of external thread 1015. Blind hole 1035 may also have, at the lower, inner end of internal thread 1037, an annular groove 1091 most of which is curved in axial section, and forms a transition between internal thread 1037 and cylindrical hole section 1038, and whose surfaces at least approximately continuously transition into that of cylindrical hole section 1038. The implant shown in FIGS. 38 and 39 also has a lower, short blind hole 1093 coaxial with axis 1003 with a opening 1094 located at first end 1008 of the implant and a bottom 1095 located inside the lower half of anchoring part 1005 at a short distance from bottom 1039 of upper blind hole 1035. Lower blind hole 1093 tapers from opening 1094 to bottom 1095 essentially for its entire length and is limited by a surface that, at its bottom, and for example at least approximately for the entire length of the blind hole in axial section, is concavely curved, smooth, and continuously and for example approximately parabolic. Anchoring part 1005 is also provided, at the lower end of external thread 15, with lengthwise holes 1097 that terminate in blind hole 1093 and have a center line running in the lengthwise direction and lateral surfaces parallel thereto, that form an acute lead angle a with axis 1003 as viewed in the radial direction. The implant according to FIGS. 38 and 39 is particularly advantageous for applications in which the implant is to have relatively little penetration into the bone and the length of the generally cylindrical section 1001 can be only approximately 6 to 8 mm.

Implant 1001 shown in FIG. 40 has an anchoring part 1005 whose generally cylindrical section 1001 is once again provided with an external thread 1015. Its core diameter D is less than that of the implants shown in FIGS. 31 to 39 and is preferably 3 mm at most, preferably at least 2.5 mm, and for example approximately 2.8 mm. The maximum diameter of head 1007 and shoulder 1021 are on the other hand for example approximately the same as those of the implants shown in FIGS. 31 to 39. Blind hole 1035 also has an opening 1036 at the second end 1009 of the implant, an internal thread 1037, a cylindrical hole section 1038, and a bottom 1039. Internal thread 1037 is for example formed as a round thread or Whitworth thread. The inner end of internal thread 1037 at a greater distance from the opening is again inside the expanding, trumpet-shaped section 1013 of the implant. The diameter of cylindrical hole section 1038 is at most the same as the core diameter of the internal thread and for example a little smaller than the core diameter. Blind hole 1035 has an annular groove 1091 between the inner end of internal thread 1037 that is further from opening 1036 and cylindrical section 1038, said groove forming a transition between internal thread 1037 and cylindrical hole section 1038. The maximum diameter of groove 1091 is at least the same as the maximum diameter or nominal diameter of internal thread 1037 and for example a little larger than its maximum thread diameter. The section of groove 1091 that immediately abuts the internal thread is concavely curved in axial section. It is abutted by an approximately conical and/or (in axial section) slightly convexly curved section that in axial section is approximately parallel to the section surrounding it in cross section of the external surface of trumpet-shaped section 13 of the implant and connects the deepest point of the groove, having the largest diameter, at least approximately continuously and smoothly with cylindrical hole section 1038. The wall of the implant surrounding blind hole 1035 then has, between the deepest point of groove 1091 having the largest diameter and cylindrical hole section 1038, approximately the same thickness as at the lower, thinner end of trumpet-shaped section 1013 and at the core diameter of external thread 1015. Bottom 1039 of blind hole 1035, as in the embodiments described above, is formed by a surface concavely curved in axial section, which surface in axial section at least approximately continuously and smoothly abuts the surface of cylindrical hole section 1038. By these shapes of internal thread 1037, groove 1091, and bottom 1039, despite the small core diameter D of external thread 1015, the implant is largely prevented from breaking when heavily stressed. Cylindrical section 1011 of the implant is provided with lengthwise, sloping grooves and/or holes 1071 forming chip surfaces 1053 in the vicinity of lower, first end 1008; due to the smaller core diameter, it may be possible for only two such grooves and/or holes to be present.

Moreover, internal thread 1037 can be formed as a round or Whitworth thread for maximum uniformity of shape, as can the implant types described above whose external thread core diameter is approximately 3.5 mm.

Figure 41:
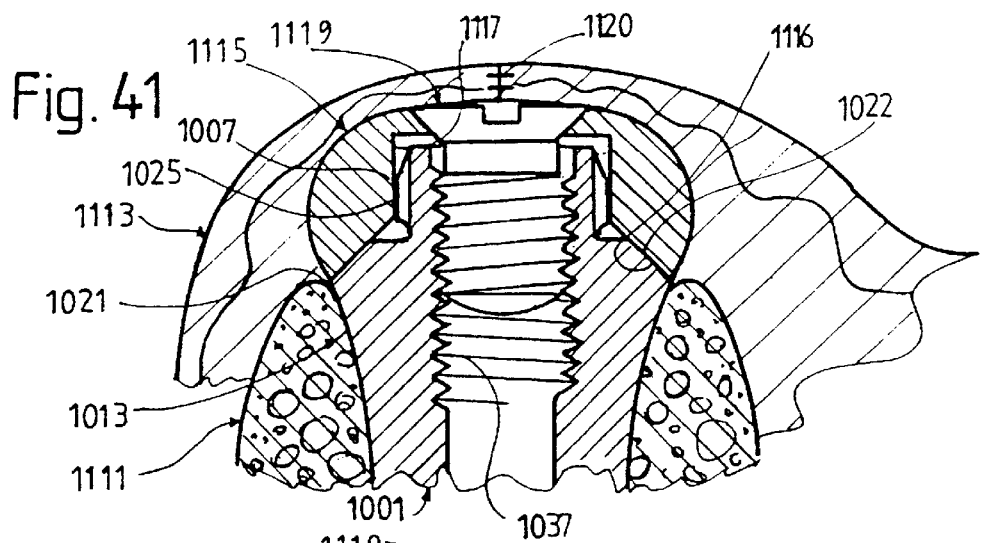
FIG. 41 shows a section through a bone, the gingiva, and a section of a subgingivally inserted implant provided with a healing cap.
Figure 42:
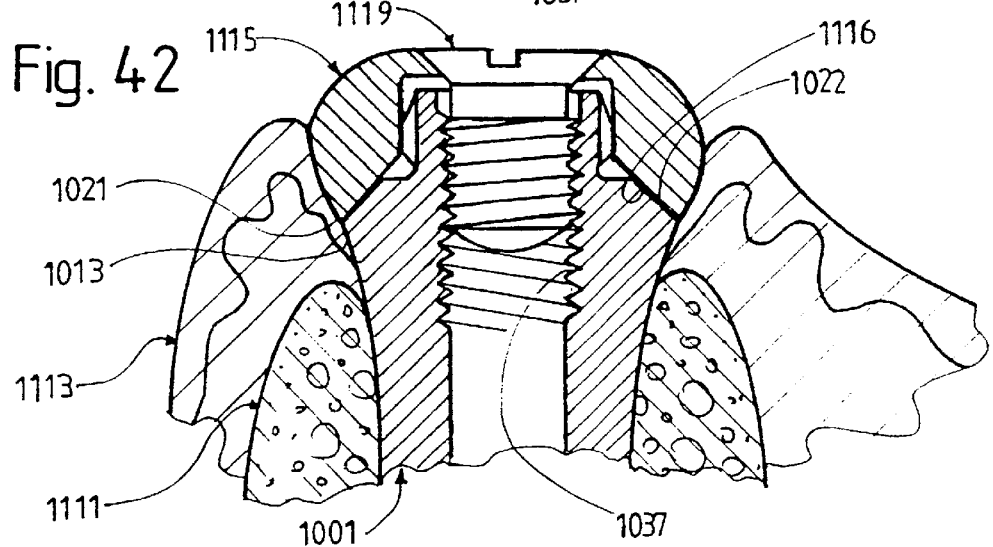
FIG. 42 shows a representation analogous to FIG. 41, but with an implant countersunk relative to the gingiva.
Figure 43:
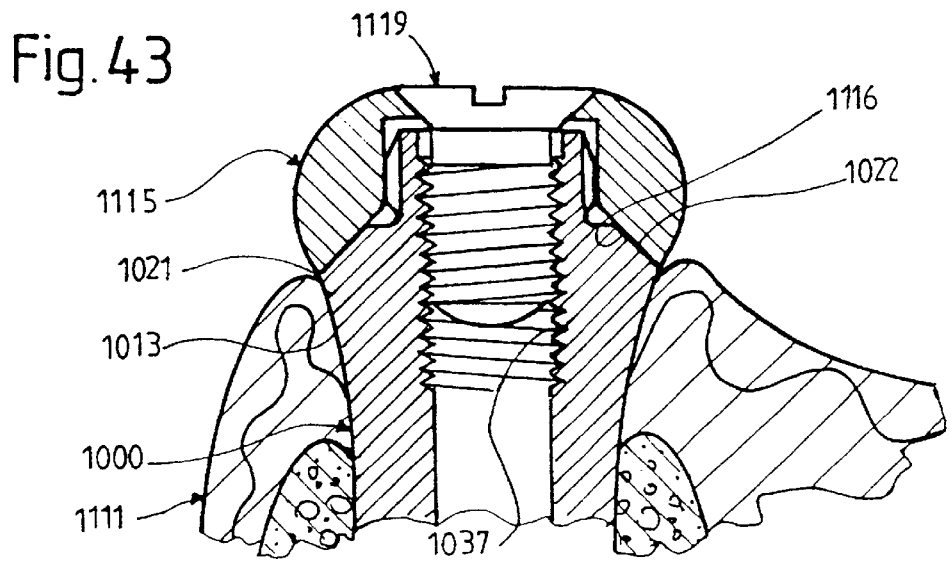
FIG. 43 shows a representation analogous to FIG. 41, but with a transgingivally inserted implant.

FIGS. 41, 42, and 43 show a jawbone 1111 and the gingiva 1113 of a patient and various implants 1001 inserted at various depths into the bones, with a one-piece element 1115 or healing cap 1115 attached to the implant. Healing cap 1115 has a conical bearing surface 1116 that abuts conical shoulder surface 1022 of implant 1001 without a gap. The interior space of healing cap 1115 has a cylindrical section guided with limited radial play by the axially parallel head section 1025 of head 1007. The external surface of the healing cap is vaulted, continuously curved in axial section, and at the outer edge of conical shoulder surface 1002 contacts the external surface of trumpet-shaped section 1013 of the implant smoothly and continuously in an essentially gap-free manner. The healing cap is removably attached with a screw 1119 to implant 1001. Screw 1119 has a head countersunk into the top section of the healing cap flush with the top surface of the healing cap and a thread screwed into internal thread 1037 of the implant.

Implant 1001 shown in FIG. 41 is inserted subgingivally into the patient's mouth. The edge formed by the upper end of trumpet-shaped section 1013 and the outer edge of conical shoulder surface 1022 is then approximately at the level of the ridge of the bone. Gingiva 1113, namely the soft tissue, is fitted against implant 1001 over the healing cap once healing cap 1115 has been attached and sutured at 1120. After a healing phase of 3 to 4 months, another incision is made into the gingiva and a one-piece or multipart superstructure element is attached to the implant. Subgingival insertion of the implant is done in two phases: in the first phase the implant is inserted and in the second phase another incision is made into the gingiva and the superstructure element is attached.

Implant 1001 shown in FIG. 42 is semi-submerged relative to the gingiva. The outer edge of conical shoulder surface 1022 in this case is between the ridge of the bone and the highest point of the gingiva. The cap is then approximately flush with the gingiva or partly projects somewhat from it. This arrangement of the implant is used primarily for forming individual artificial teeth and bridges. The superstructure element serving as a crown or bridge then lies slightly, for example 1 to 2 mm, under the gingival surface on shoulder surface 1022, so that the join is no longer visible and is not unaesthetic.

Implant 1 shown in FIG. 43 is inserted transgingivally. The outer edge of conical shoulder surface 1022 is then approximately at the highest point of gingiva 1113. The operation can then be done in one phase, i.e. only one incision need be made into the gingiva. The transgingival arrangement is used for example for attaching bone structures and in cases in which appearance is less important.

There is thus a choice of inserting identically shaped implants subgingivally, transgingivally, or semi-submerged. This is an important advantage for dentists and dental hospitals.

Figure 44:
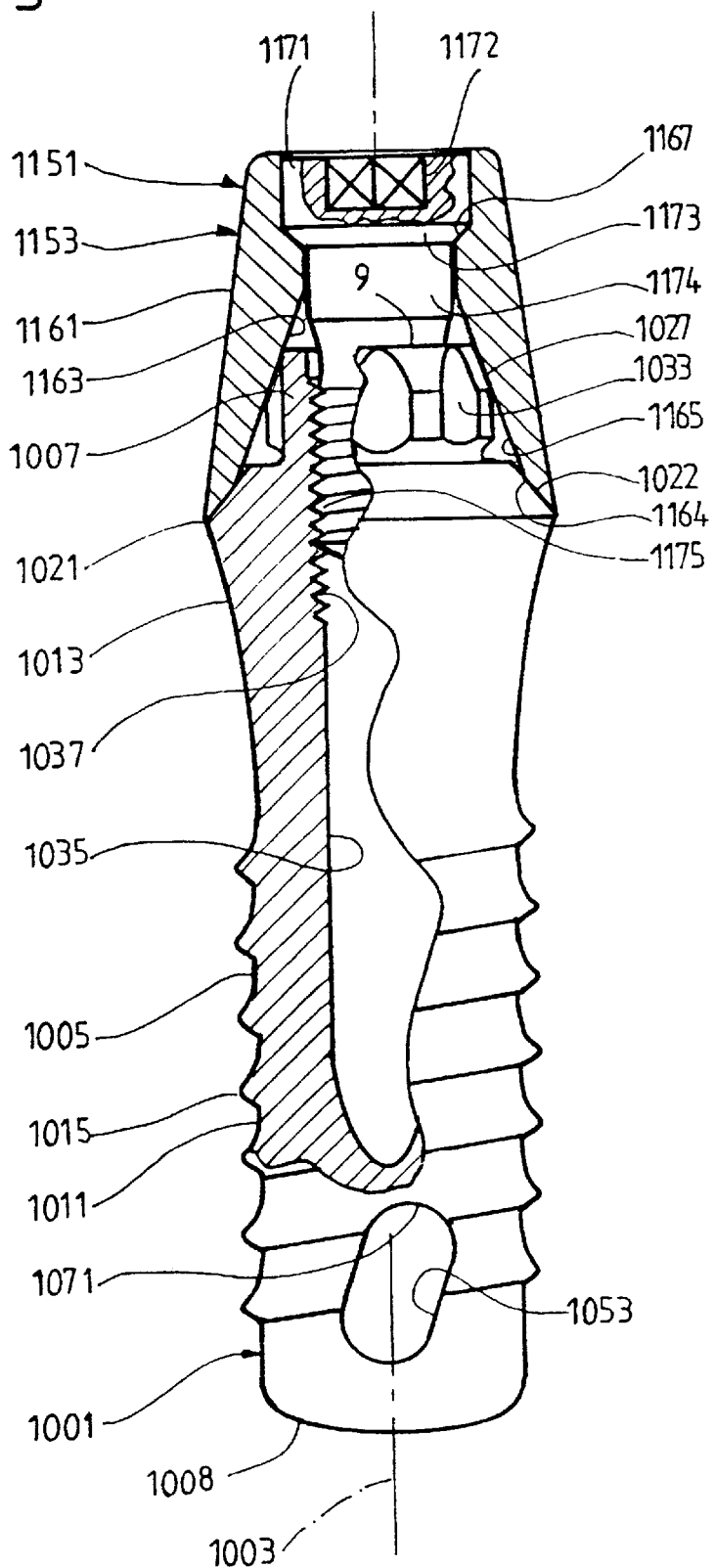
FIG. 44 shows a device shown partially in side view and partially in axial section, with an implant according to FIGS. 34 to 36 and with a cap.

Device 1151 shown in FIG. 44 has an implant 1001 whose anchoring part 1005 is inserted for example into the interforaminal region of a lower jawbone, not shown. Head 1007 of implant 1001 has positioning surfaces formed by grooves for example. Device 1151 has a superstructure element 1153 with a cap 1161 attached to an implant 1001 rotationally symmetrically to axis 1003 and for example another rib, not visible, and another head, also not visible, attached to another implant. Cap 1161 is made of a metal material, for example a gold alloy or titanium, and has an interior space 1163 formed by a through-hole coaxial to axis 1003 and has a conical supporting surface 1164 at the bottom. This is abutted by a likewise conical but steeper internal surface 1165 that forms the same angle with axis 1003 as conical head section 1027 of implant 1001. Interior space 1163 has a constriction above conical surface 1165 and a conical supporting surface 1167 on the top side of the latter. Cap 1161 is attached to the implant with an occlusal screw 1171 whose cylindrical head 1772 has a multi-sided hole and is countersunk in the cap. Head 1172 is abutted by a conical section 1173 supported on supporting surface 1167 and connected by a cylindrical shaft section 1174 with threaded part 1175. The thread of the latter is screwed into internal thread 1037 of the implant. The screw presses the cap against the implant, so that the cap with its supporting surface 1164 rests firmly and without gaps at least on the outer area of shoulder surface 1022 of the implant while a very narrow gap is present between the conical surface sections of head section 1027 of the implant and the conical internal surface 1165 of the cap, the width of this gap being a maximum of 0.02 mm or preferably only a maximum of 0.01 mm and for example in the micron range. The cap is then further guided by conical section 1027 of the implant, centered, and supported when lateral forces act on it approximately transversely to axis 1003. Cap 1161 is designed for free positioning and thus does not have the surfaces abutting positioning surfaces 1033 of implant 1001 formed by positioning grooves. The cap has an upwardly conically tapering external surface and a flat top surface at the upper end. The shape of interior space 1163 of cap 1161 makes it possible easily to place the cap on head 1007 using little force and practically without friction, and remove it therefrom, if axes 1003 of the implants serving to hold superstructure element 1153 are not parallel to each other and form an angle of up to 40° for example with each other.

Figure 45:
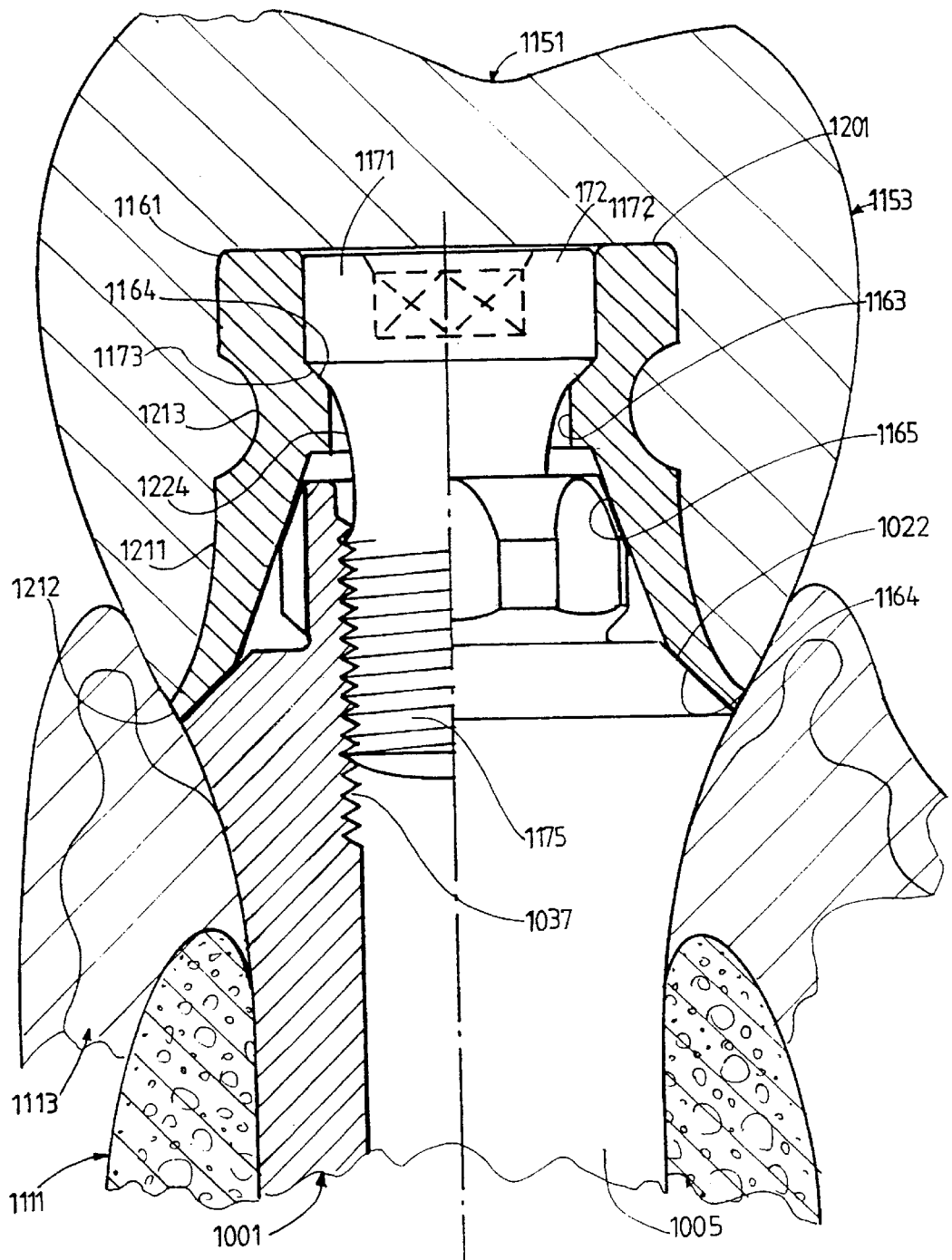
FIG. 45 shows an axial section through a device with an implant inserted into a bone with another cap.
Figure 46:
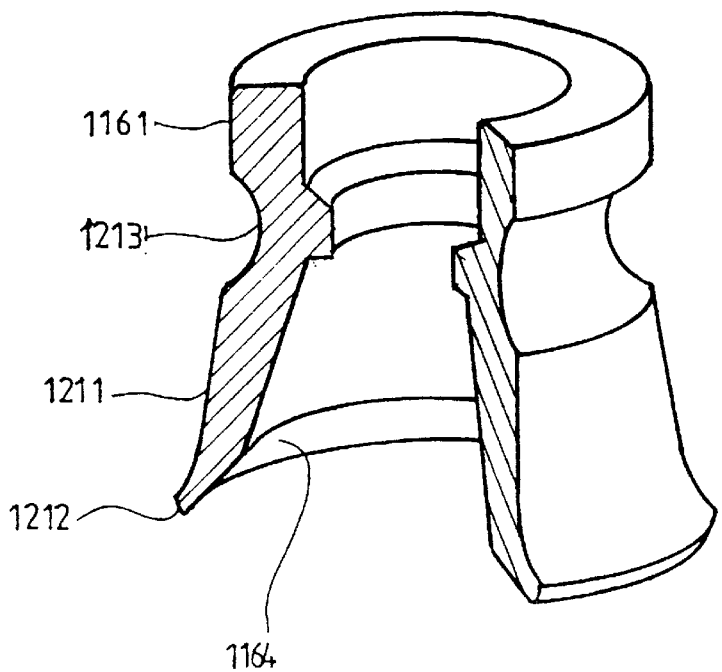
FIG. 46 shows a diagonal view of the cap of the device according to FIG. 45.

FIG. 45 shows a bone 1111, a gingiva 1113, and a device 1151 having a semi-submerged implant 1001, a cap 1161 also shown separately in FIG. 46, an occlusal screw 1171, and a porcelain crown 1201. Like the cap shown in FIG. 44, cap 1161 is rotationally symmetrical with the axis and designed for free positioning, and its supporting surface 1164 abuts shoulder surface 1022. External surface 1211 of the cap shown in FIGS. 45 and 46 generally tapers upward from the bottom, but has an external surface section 1212 at the bottom that slopes outwardly upward and abuts the upper end of trumpet-shaped section 1013 of the implant at least approximately smoothly. External surface 1211 is also provided with an annular groove 1213 that is arcuate in axial section. Occlusal screw 1171 shown in FIG. 45 differs from the occlusal screw shown in FIG. 44 in that, instead of cylindrical shaft section 1174, it has a bent shaft section 1224 that is concave in axial section and at least approximately continuously joins conical section 1173 with threaded part 1175, thus reducing the risk that the occlusal screw will break.

Figure 47:
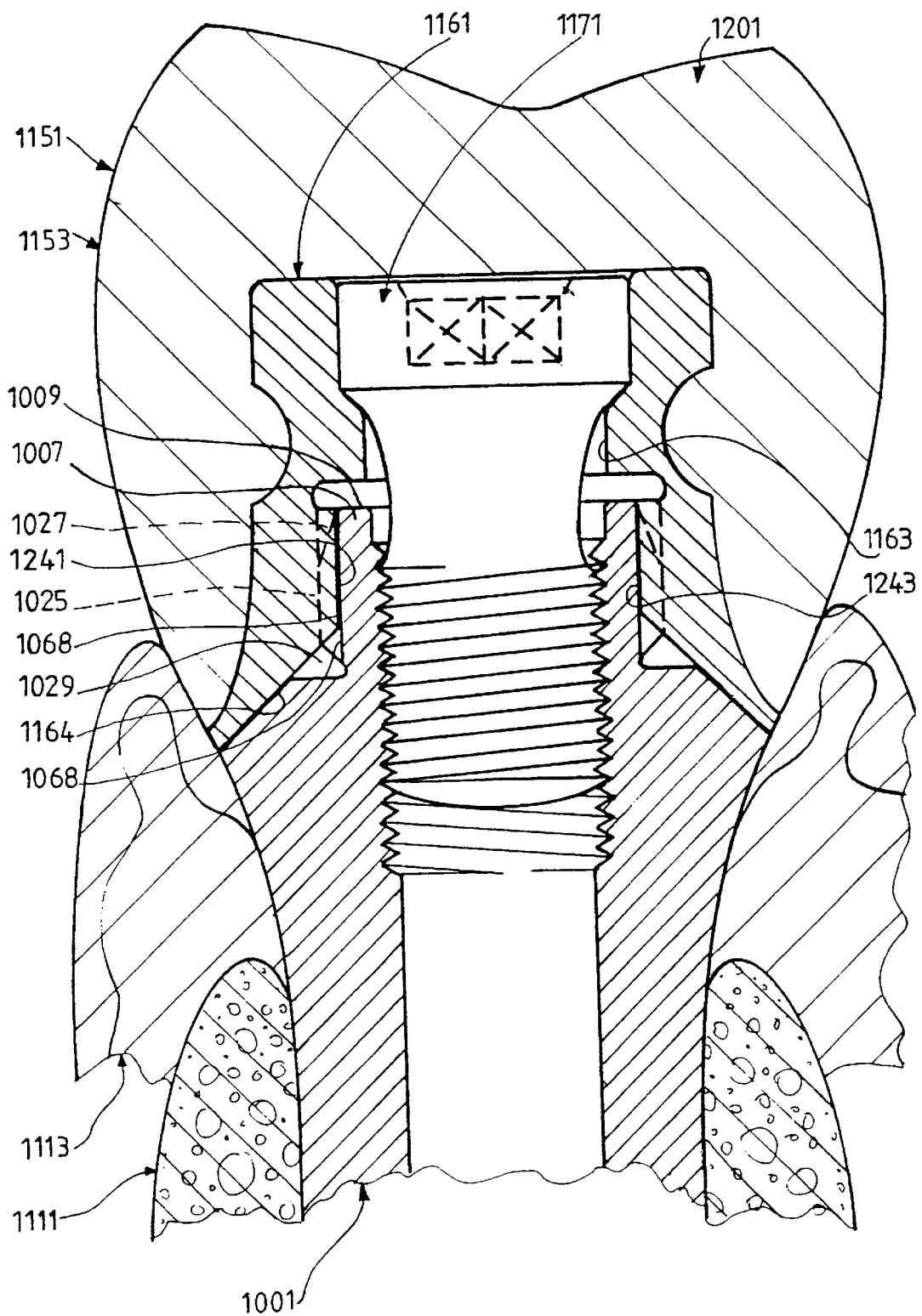
FIG. 47 shows an axial section through a device with an implant inserted into a bone and a cap designed for multi-positioning.
Figure 48:
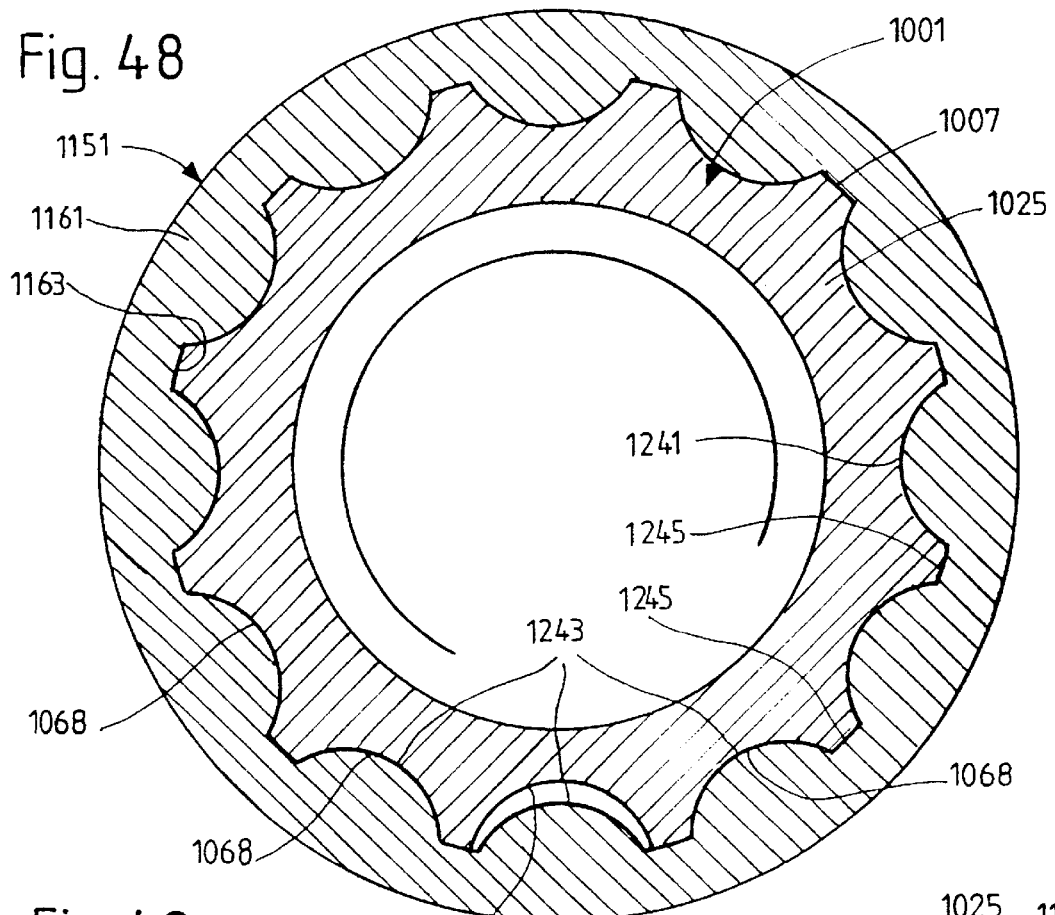
FIG. 48 shows a cross section through the axially parallel head section of the implant and the cap of the device according to FIG. 47.

Device 1151 shown in FIG. 47 and partially in FIG. 48 has an implant 1001 inserted into a bone 1111 and a superstructure element 1153. Superstructure element 1153 has a cap 1161 attached by an occlusal screw 1171 to implant 1001, and a crown used to form a single artificial tooth. Head 1007 of the implant has eleven for example identically shaped first positioning interstices 1068 or positioning grooves 1068 and a second, wider and deeper positioning interstice 1069 or a second positioning groove 1069. The head thus has a total of twelve positioning grooves forming positioning surfaces 1033.

Cap 1161 shown in FIGS. 47 and 48 is partially similar to the cap shown in FIGS. 45 and 46 but above conical supporting surface 1164 has a positioning section 1241. The latter is generally cylindrical but, along the periphery of interior space 1163, has alternating sequential positioning projections 1243 and positioning interstices 1245. Thus, twelve identically shaped and dimensioned projections 1243 uniformly distributed along the periphery of the interior space and twelve likewise uniformly distributed and identically shaped interstices 1245 are present. Of the twelve projections 1243 of the cap, eleven engage a first positioning groove 1231 and one engages second positioning groove 1232. The cap is accordingly designed for multipositioning and can be positioned on the implant in twelve different positions (i.e. rotational positions) when it is connected to the implant, with the angle between adjacent rotational positions being 30°. Projections 1243 have straight, axial ribs and have surfaces shaped like arcs of circles in cross section. When head section 1025 is axially parallel, these surfaces are at least approximately complementary to the first positioning grooves 1068. Projections 1243 engaging first positioning grooves 1068 have a play therein that amounts to at most 0.02 mm, preferably at most 0.01 mm, and for example in the range of a few microns in the radial direction, in particular along a circle coaxial with axis 1003. On the other hand, projection 1243 of the cap, that engages second positioning groove 1069, is separated from the second positioning surface by a fairly wide gap. Positioning interstices 1245 of the cap also fit with at most very limited play into the cylindrical surface sections of the axially parallel head section. Positioning projections 1243 of the cap also engage conical head section 1027 up to the free end of head 1007, i.e. up to second end 1009 of implant 1001, in the positioning grooves of the head and are thus guided in head sections 1025, 1027 up to second end 1009 of the implant with very limited play by the first positioning grooves and supported against forces acting perpendicularly to axis 1003. The cap formed for multipositioning is thus, despite the small height of the head, also well-supported against lateral forces by the implant and is connected with the implant in stable fashion.

Figure 49:
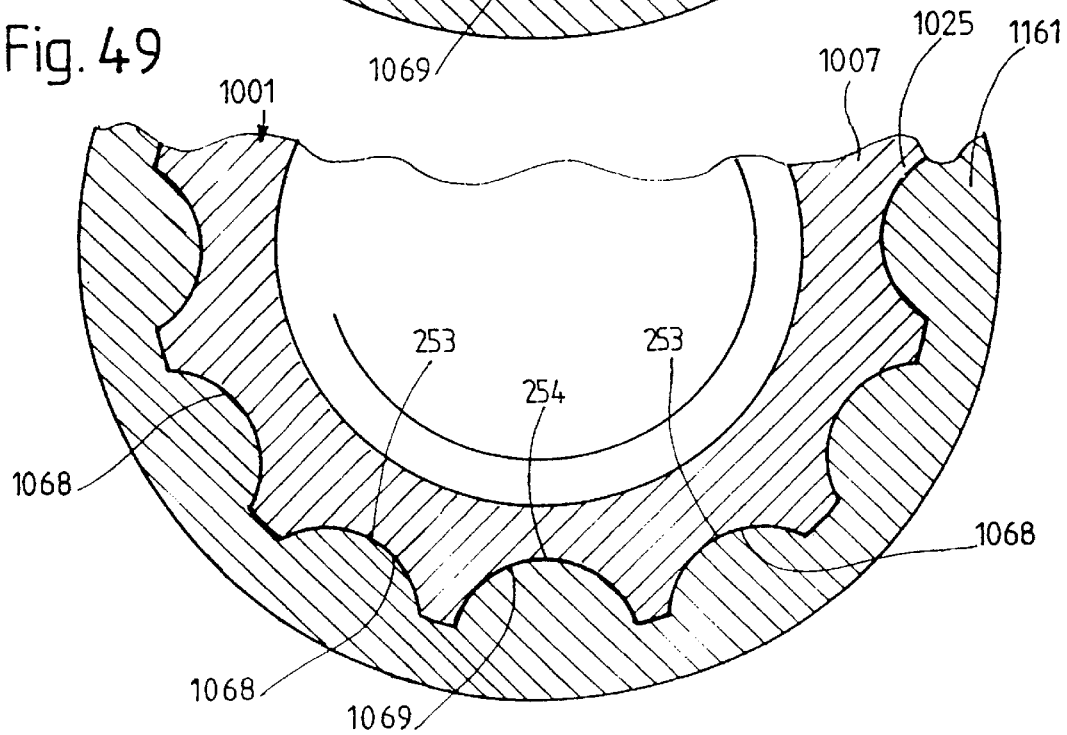
FIG. 49 shows a cross section analogous to FIG. 48, but with the cap designed for single positioning.

Head 1007 of implant 1001 shown in FIG. 49 has the same shape as the in the implants shaped as in FIGS. 47 and 48 and has several first, identical positioning grooves 1068 and a second, wider and deeper positioning groove 1069. Cap 1161 shown in FIG. 49 is formed for single positioning and has, for each positioning groove 1068, a first positioning projection 1253 projecting thereinto and a second positioning projection 1254 projecting into second positioning groove 1069. The latter is wider and higher than the first positioning projections, so that it fits with very limited play into second positioning groove 1069 and cannot engage any first positioning groove 1068.

Figure 51:
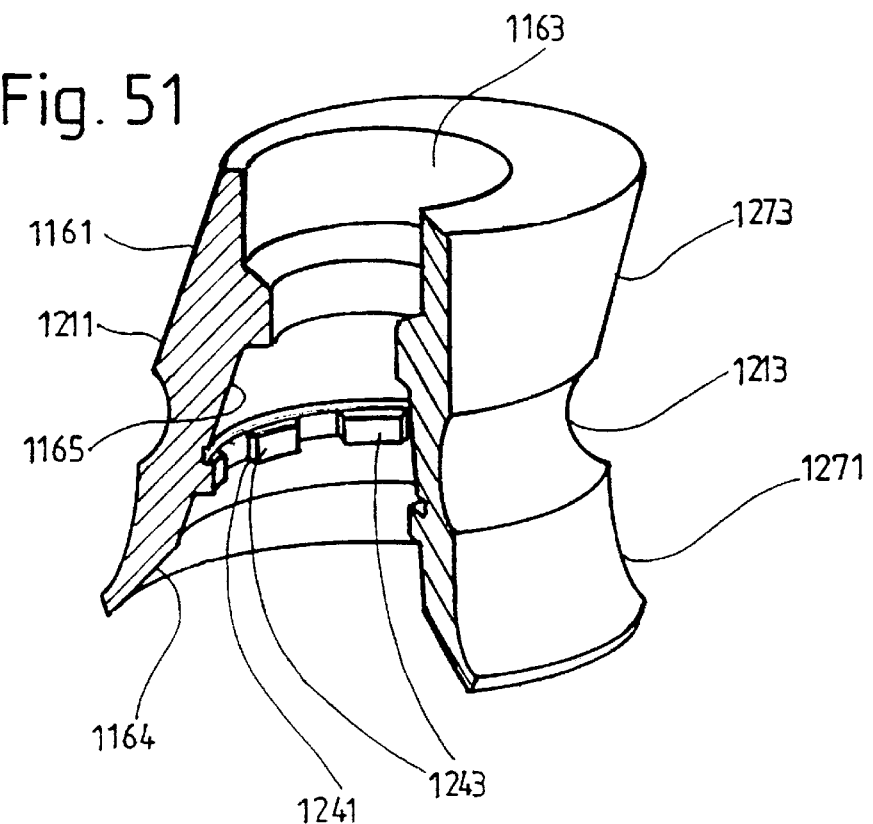
FIG. 51 shows a diagonal view of the cap according to FIG. 50.
Figure 50:
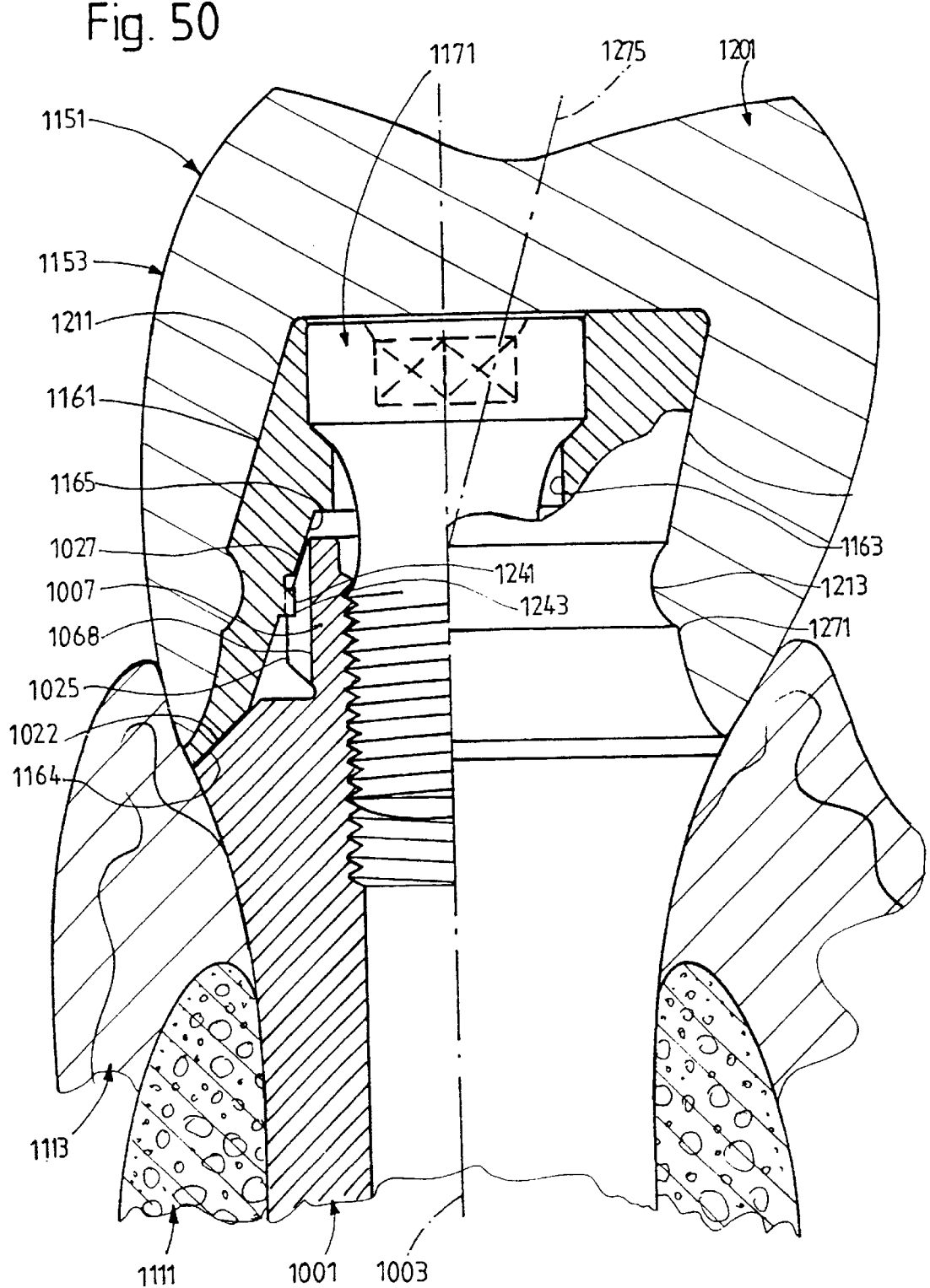
FIG. 50 shows a device with an angled cap.

Implant 1001 of the device 1151 shown in FIG. 50 has a head 1007 with several first positioning grooves 1065 and a second positioning nut, not shown. The device also has a superstructure element 1153 with a cap 1161 shown separately in FIG. 51, an occlusal screw 1171, and a crown 1201. Cap 1161 or, to be more precise, its external surface 1211, is at an angle. Lower external surface section 1271 is generally rotationally symmetrical with axis 1003 of the implant up to and including annular groove 1213. Upper external surface section 1273 located above annular groove 1213 is approximately coaxial with an axis 1275 that forms an acute angle with axis 1003. The top surface of the cap is flat and approximately perpendicular to axis 1003. Interior space 1163 of the cap is coaxial with axis 1003 and generally rotationally symmetrical therewith up to the upper end of the cap. Cap 1161 has a conical supporting surface 1164 resting on shoulder surface 1022 of the implant and also, similarly to the caps in FIGS. 44 and 45, a conical internal surface 1165 supported with limited play by conical head section 1027. However, the cap also has a positioning section 1241 with positioning projections that for example all have the same shapes and are designated "1243," so that the cap is designed for multipositioning. The height of positioning projections 1243 is however considerably less than the depth of positioning grooves 1068, 1069 of the head, so that their tops are at a distance from the deepest points of the positioning grooves. Moreover, positioning projections 1243 are also considerably shorter than the positioning grooves of the head, so that they engage the positioning grooves for example only in the vicinity of the connection of the two head sections 1025, 1027. The dimension or width of projections 1243 measured along the periphery is such, however, that it allows precise positioning. The cap shown in FIGS. 50 and 51 is particularly applicable to bridge constructions that have two implants with axes that are not parallel to each other and diverge or converge. Superstructure element 1153 that forms a bridge construction can then be readily placed on and removed from the implants even when the implant axes are not parallel. Also, despite the small positioning projections of the cap, good positioning and good protection against lateral forces are achieved.

Figure 52:
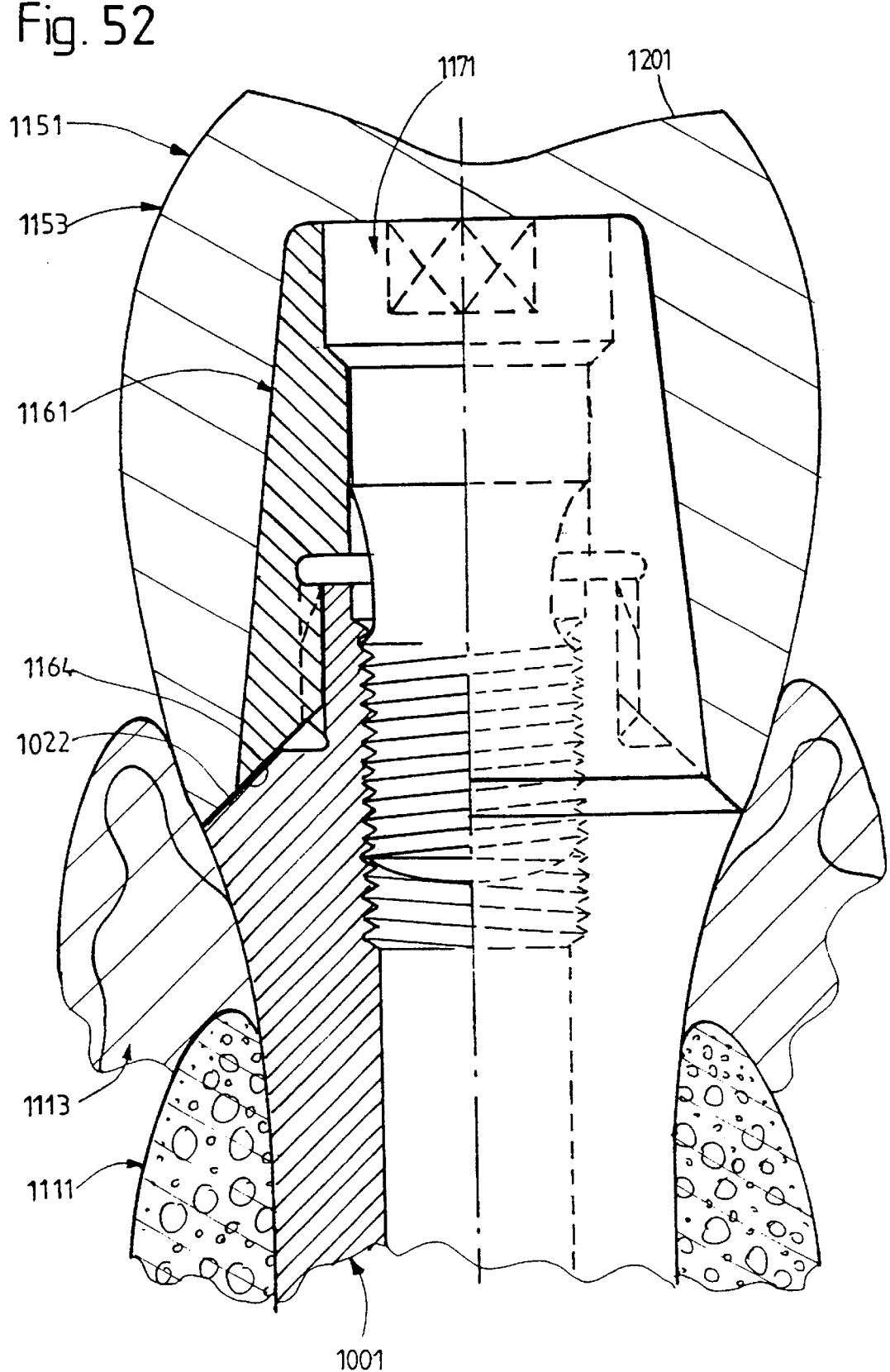
FIG. 52 to 54 are devices with various cap variants.

The device 1151 shown in FIG. 52 has an implant 1001 with positioning grooves and a superstructure element 1153 with a cap 1161 designed for multipositioning or single positioning. The conical supporting surface 1164 of said cap abuts the conical shoulder surface 1022 of the implant. The outer edge of supporting surface 1164 however has a smaller diameter than the outer edge of shoulder surface 1022, so that this surface still has a section surrounding the cap. The head of occlusal screw 1171 is approximately flush with the upper end of the cap. With this cap, the dentist can make a impression directly without using a special impression cap, just as with a natural tooth. A crown 1201 can be made based on this impression, that also abuts shoulder surface 1022.

Figure 53:
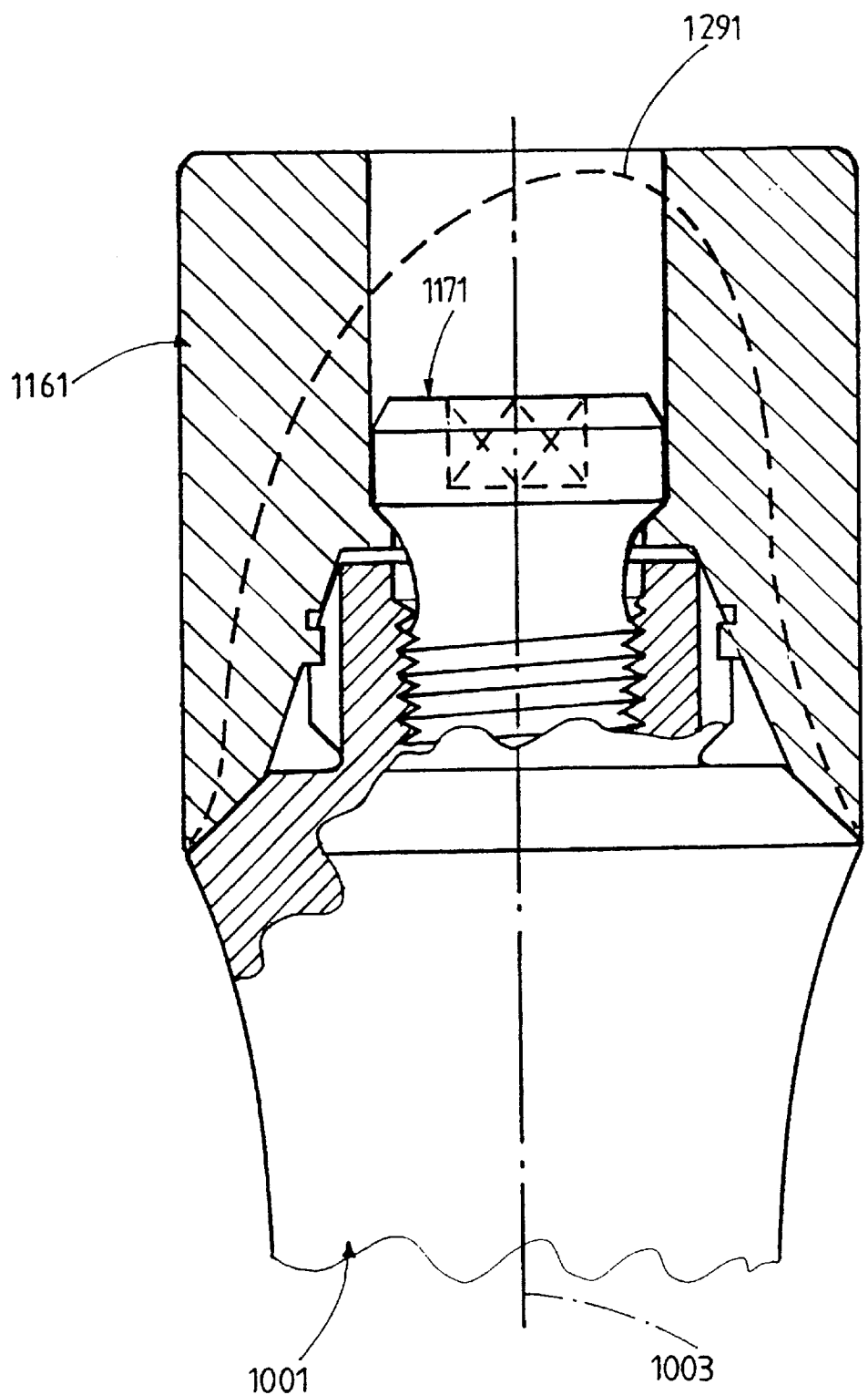

The device according to FIG. 53 has a cap 1161 that is generally rotationally symmetrical with axis 1003 of implant 1001 but designed for multipositioning or single positioning, and an occlusal screw 1171, whose head is countersunk fairly deep into the cap and is at a relatively long distance from the upper, free end of the cap. The cap can be ground for example for use, resulting in the grinding surface 1291 shown in dashed lines.

Figure 54:
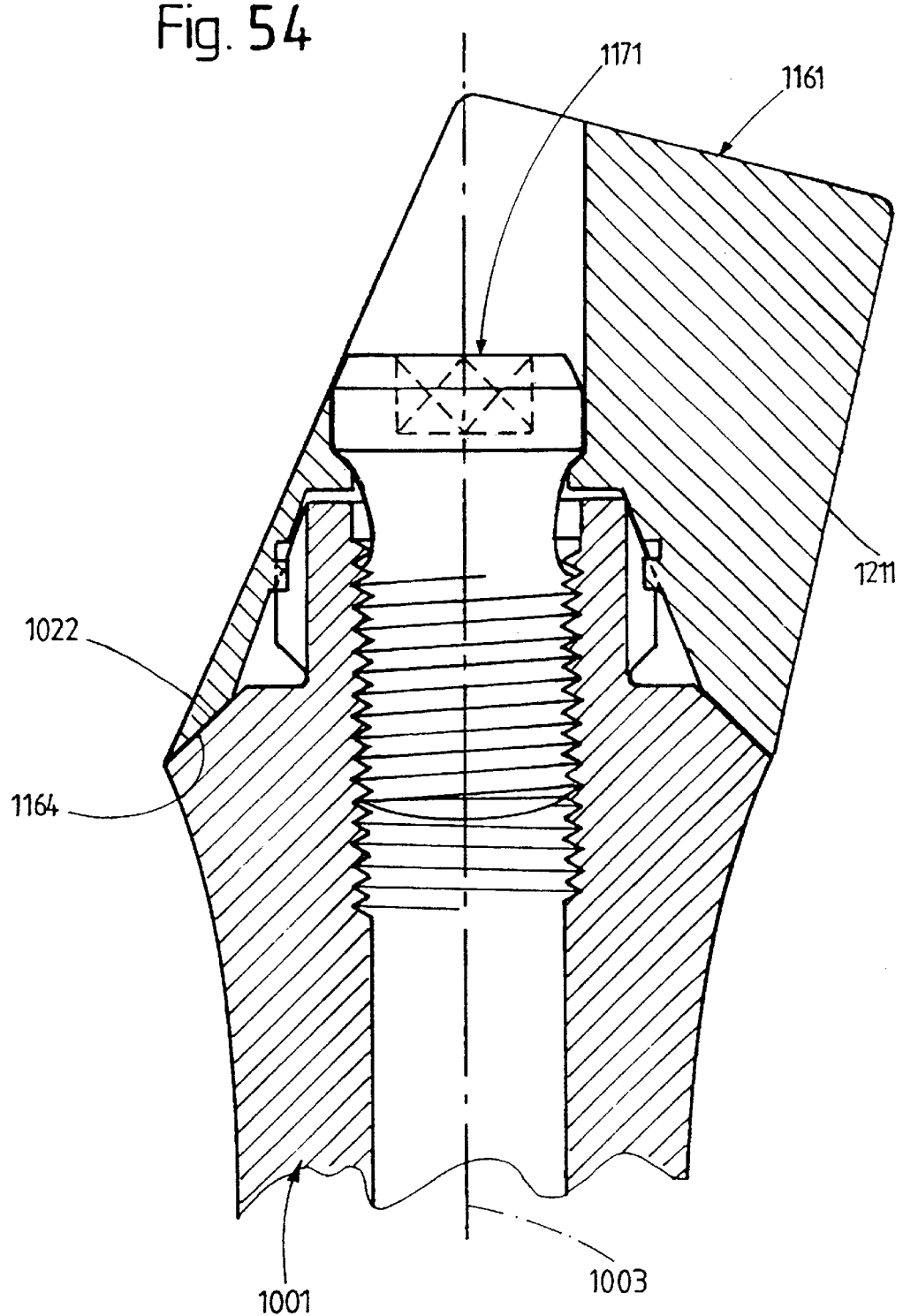

The device shown in FIG. 54 has a implant 1001 with positioning grooves, a cap 1161, and an occlusal screw 1171. With this cap, the supporting surface 1164 abutting shoulder surface 1022 of the implant is once again rotationally symmetrical with axis 1003, while the entire external surface 1211 of the cap is rotationally symmetrical with an axis inclined to axis 1003, and for example conical. The top surface of the cap is for example at right angles to the aforementioned axis. The cap can be ground for use if necessary. Also, a crown or bridge or the like can be cemented onto the cap.

The caps shown in FIGS. 52 to 54 can be made of a metal material for example such as a gold alloy or titanium. However, a cap can first be made of a burnable plastic which is then replaced by a cast cap.

Figure 55:
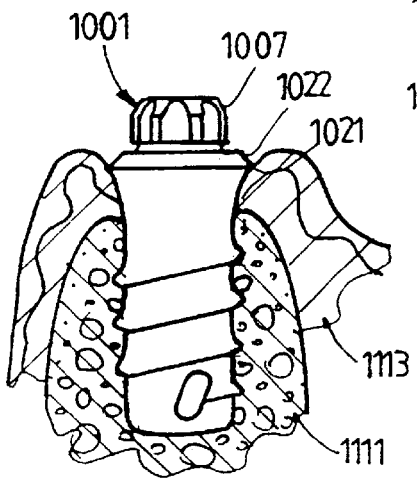
FIGS. 55 to 62 are work steps in forming a dental prosthesis.

The steps for creating a dental prosthesis will now be explained with reference to FIGS. 55 to 62. FIG. 55 shows the lower jawbone 1111 of a patient, gingiva 1113, and a semisubmerged implant 1 after the healing phase. Head 1007 of the implant is provided with positioning surfaces formed by grooves.

Figure 56:
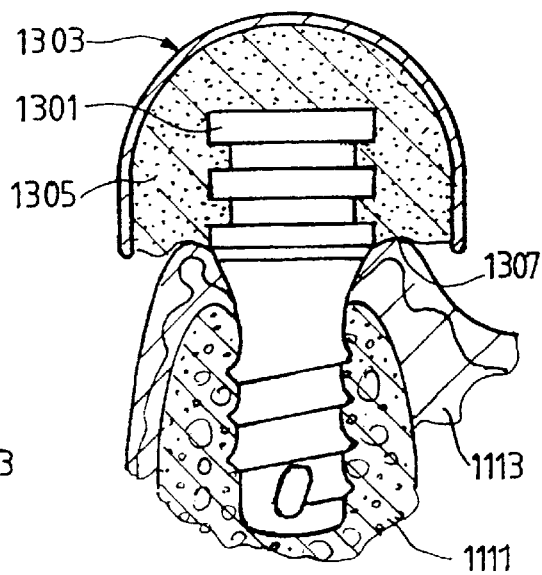
Figure 57:
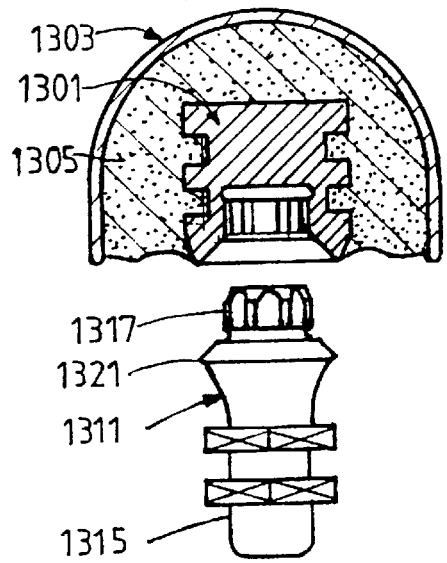

Once the implant 1001 has healed in, an impression element 1301 shown in FIG. 56 is removably attached to the implant—clipped on or screwed, for example. Impression element 1301 consists of a one-piece or multipart impression cap and rests on shoulder surface 1022 of implant 1001 without leaving a gap. The cap of impression element 1301 is designed for example—as described for caps of superstructure elements—for multipositioning or single positioning, so that the impression element is positioned in a specific rotational position. Once the impression element has been attached, an impression spatula 1303 filled with deformable impression material 1305 is pressed over impression element 1301 against the ridge of bone and gingiva 1113, and an impression is taken. Once it has hardened, the impression material forms a impression surface 1307.

Impression spatula 1303 together with impression material 1305 and the impression element 1301 embedded therein is then removed from implant 1001. A manipulating implant 1311 shown in FIG. 57 has an anchoring part 1315, a head 1317, and a shoulder 1321 between them. Head 1317 and shoulder 1321 of the manipulating implant have the same shapes as for the implant shown in FIGS. 55 and 56, while anchoring part 1315 is usually different from that of implant 1001.

Figure 58:
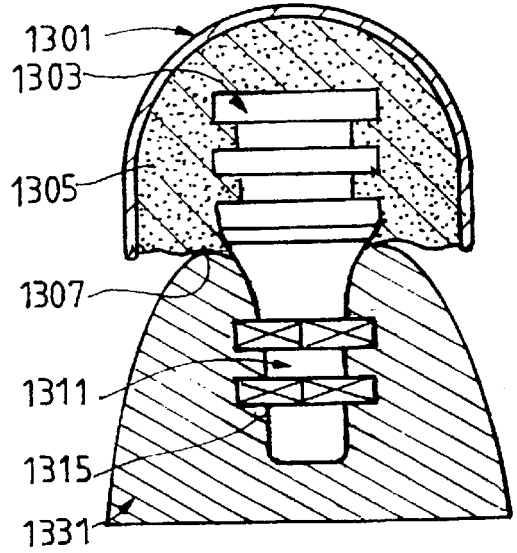
Figure 59:
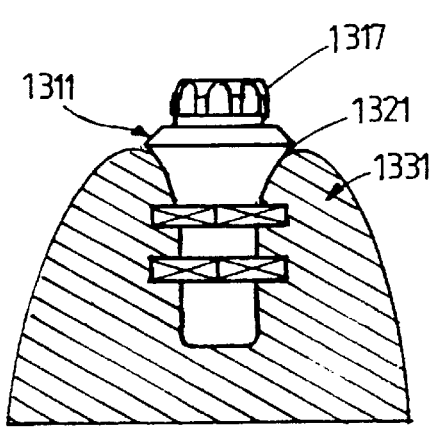

Head 1317 of manipulating implant 1311 is now placed in the interior space of impression element 1301 according to FIG. 58, positioned in a specific rotational position, and removably attached, for example clipped, to the impression element. The conical shoulder surface of the manipulating implant then rests on the conical supporting surface of the impression element, with the outer edges of these surfaces being visible from outside. Then a modeling material, plaster for example, is pressed over anchoring part 1315 of manipulating implant 1311 against impression surface 1307 and the master model 1331 shown in FIG. 58 is made from the modeling material. Once the modelling material has hardened, anchoring part 1315 of the manipulating implant is anchored in the master model.

Manipulating implant 1311 is then separated from the impression element. Head 1317 and the conical shoulder surface of shoulder 1321 of the manipulating implant then project out from master model 1331 according to FIG. 59.

Figure 60:
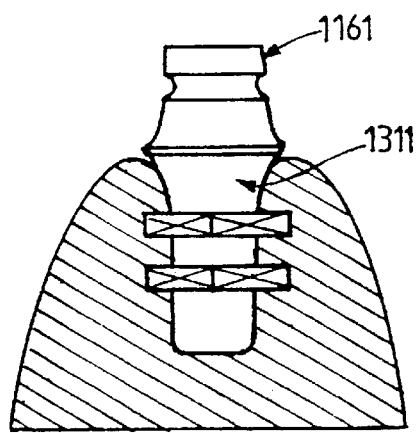
Figure 61:
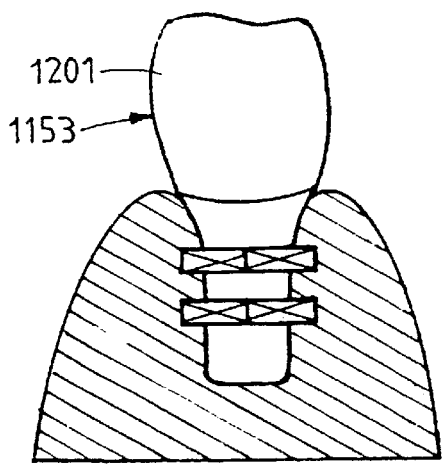
Figure 62:
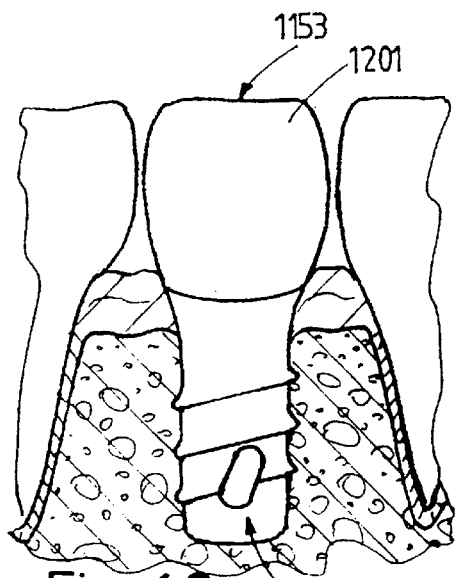

In the next step, a cap 1161 shown in FIG. 60 serving as a component of a superstructure element is placed on the head of manipulating implant 1311 and removably attached thereto with an occlusal screw. Then a crown 1201 shown in FIG. 61 and made of porcelain for example is made and attached to cap 1161. The crown then forms a superstructure element 1153 together with cap 1161. The latter is then placed in the patient's mouth according to FIG. 62 and attached to implant 1001.

Implant 1001 shown in FIG. 63 has for example yet another head, not shown, but could belong to a support that has another secondary part also not shown. The implant is in general rotationally symmetrical with an axis 1003. Anchoring part 1005 once again has a generally cylindrical section 1011 and a generally trumpet-shaped section 1063 adjoining its upper end and expanding in the direction away therefrom. At the upper end of section 1013 is a conical shoulder surface 1022. Trumpet-shaped section 1013 is provided with depressions 1425 at a distance from each other along the axis, namely annular grooves surrounding axis 1003. Each groove has in axial section a bottom 1427, a first surface 1428, and a second surface 1429. First surface 1428 is above bottom 1427 and is inclined away from the latter and from axis 1003 outward and upward in the direction of shoulder surface 1022. Second surface 1429 is located beneath the bottom, is considerably smaller than first surface 1428, and is inclined outward and downward away from the bottom, i.e. away from shoulder surface 1422. Second surface 1429 forms a considerably larger angle with axis 1403 than first surface 1428. The projections or ribs between adjacent grooves thus have an approximately serrated profile. The first and second surfaces are however continuously connected together at each bottom and at their ends facing way from the bottoms, by a section that is arcuate in axial section. When the implant is inserted into a bone 1111, the bone can grow into the depression or groove 1425 and thus improve the anchoring of the anchoring part in the bone. If the depressions or grooves 1425 project out of the bone, gingiva 1113 can also grow into the depressions or grooves 1425.

Implant 1001, partially visible in FIG. 64, has an axis 1003 and an anchoring part 1005. The latter has a generally cylindrical section 1011 with an external thread 1015. This thread has a single pitch and has a rib 1016, but could be multi-pitch and thus have more than one rib. Rib 1016 has helical turns 1451, a top 1017, a foot 1453, and two flanks 1454. A channel 1461 with a cylindrical bottom surface is present between two adjacent turns 1451. Each flank 1454 has a flank section that is straight in axial section. The straight flank sections of the rib are continuously connected with each other by a section with a radius of curvature $R_1$ that forms top 1017 and is arcuate in axial section. The flank sections that are straight in axial section are also continuously connected at the foot of the rib by a section with radius of curvature $R_2$ arcuate in axial section with the cylindrical bottom surface or channel 1461.

The flank sections that are straight in axial section form an angle g with a radial straight line 1465. This is an angle of 15° to 25°, preferably 18° to 22°, and for example approximately 20°. The axial distance between corresponding points of two adjacent turns 1451 of the rib is designated s and with a single-pitch thread is identical with its pitch. Halfway up the rib, i.e. in the middle between its top and its foot, the rib has an axial dimension a. This is a maximum of 30% and for example preferably 15% to 25% of distance s. Channel 1461 has an axial dimension b half-way up rib 1016, which is considerably larger than dimension a. The height of the rib is for example approximately 0.5 mm. Radius of curvature $R_1$ is for example approximately 0.05 mm to 0.1 mm. Radius of curvature $R_2$ is at least 0.1 mm and for example approximately 0.15 mm or even more.

When the implant shown in FIG. 64 is inserted into a bone, the space between a cylindrical surface in contact with top 1017 and a cylindrical surface defined by the bottom of the channel contains considerably more, namely approximately three to five times more, bone material than metal implant material. Also, the angle g of for example approximately 20° provides good transmission of compressive and tensile forces between the implant and the bone.

Head 1007 of implant 1001 shown in FIG. 65 has positioning interstices or grooves 1468 uniformly distributed along its periphery, all of which have the same shapes and dimensions.

The implant shown in FIGS. 66 and 67 has, instead of positioning grooves, flat positioning surfaces 1033 parallel to axis 1003 and thus not rotationally symmetrical with the axis. These surfaces are all uniformly distributed and have the same shapes and dimensions. The radial distances of the axial center lines of positioning surfaces 33 are approximately or exactly the same as the radius of the narrower, upper end of conical head section 1027. Flat positioning surfaces 1033 extend in an axial direction over the entire length of axially parallel head section 1025 and at least approximately and preferably exactly up to the thinner, upper end of conical head section 1027 and hence also up to second end 1009 of the entire implant. Flat positioning surfaces 1033 together essentially form a polygon, i.e. an octagon. Axially parallel head section 1025 however still has narrow peripheral sections of a cylindrical jacket surface between the flat positioning surfaces. The generally conical head section 1027 should in any event still have sections of a conical jacket surface between flat positioning surfaces 1033.

The implants described according to the embodiments of the implant shown in FIGS. 31 to 33 can, unless otherwise described, have the same or similar shapes to the implant described with reference to FIGS. 31 to 33 or another previously described implant. The same applies to the caps, screws, superstructure elements, and other parts described according to corresponding parts described above.

As already mentioned in the preamble, the caps can be made of a burnable plastic instead of a metal material. A dental technician can then place a meltable and/or burnable impression material such as wax on the plastic cap and thereby produce a casting model for a crown or another superstructure element. A casting impression can then be formed around it and the casting model located therein can be burned and/or melted. A superstructure element made of a casting material such as a gold alloy is then cast. The radial play between a burnable cap and the positioning section of a support supporting it may if necessary be made slightly larger than described for a device with a metal cap 101 according to FIGS. 8 and 9, for example up to approximately 0.02 mm. On the other hand, the play between the lateral surfaces of the projections of the burnable cap and the lateral surfaces of the projections of the support bearing this cap can be set for example similarly to those described for the device with a metal cap according to FIGS. 8 and 9. The burnable cap and the cap cast using it can then be positioned approximately the same as far as rotation is concerned as described for cap 101.

The supports and the elements attached thereto can be modified in other ways as well. In particular, features of various embodiments described can be combined with each other.

Instead of removably attaching a superstructure element and/or a cap to a support by a screw, a superstructure element can be made with a pin that is cemented or glued into the blind hole of the support with a binder, i.e. a cement or glue, and the superstructure element and/or the cap can be non-removably connected with the support. The support can nonetheless have an internal thread, which improves the adhesion of the binder in the support. Such a method of attachment may be of especial advantage with a superstructure element attached to two supports, for example a bridge.

The healing element or healing cap may instead be screwed to the support by a clamping and/or latch connection.

Finally, reference is made to the priorities of Swiss Patent Applications 1220/97 and 1222/97 filed by the same applicant, the content whereof is incorporated into this patent application provided there are no contradictions.

Friatec AG Case 4+7/Doss. 19787 PCT Project 2000-1

List of Parts

Figure 1:
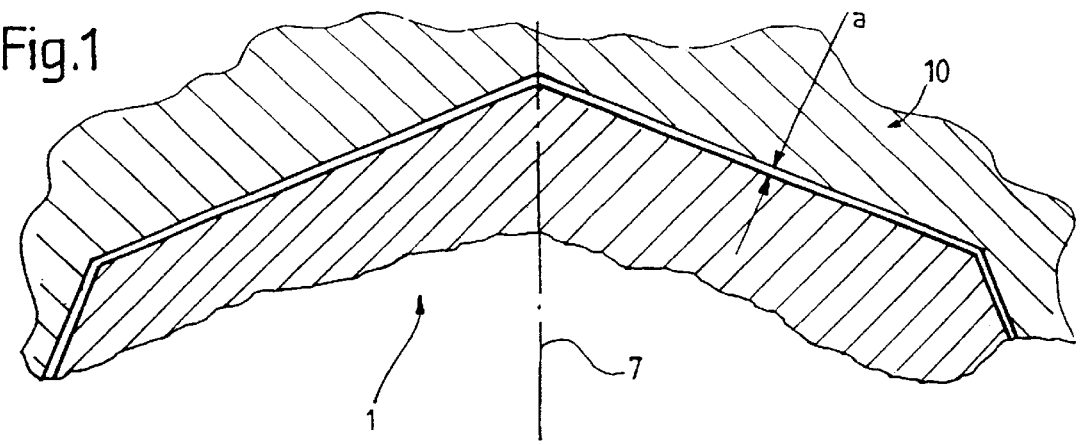
FIG. 1 shows a cross section through a known support and a cap that shows in a desired rotational position with respect thereto.
Figure 2:
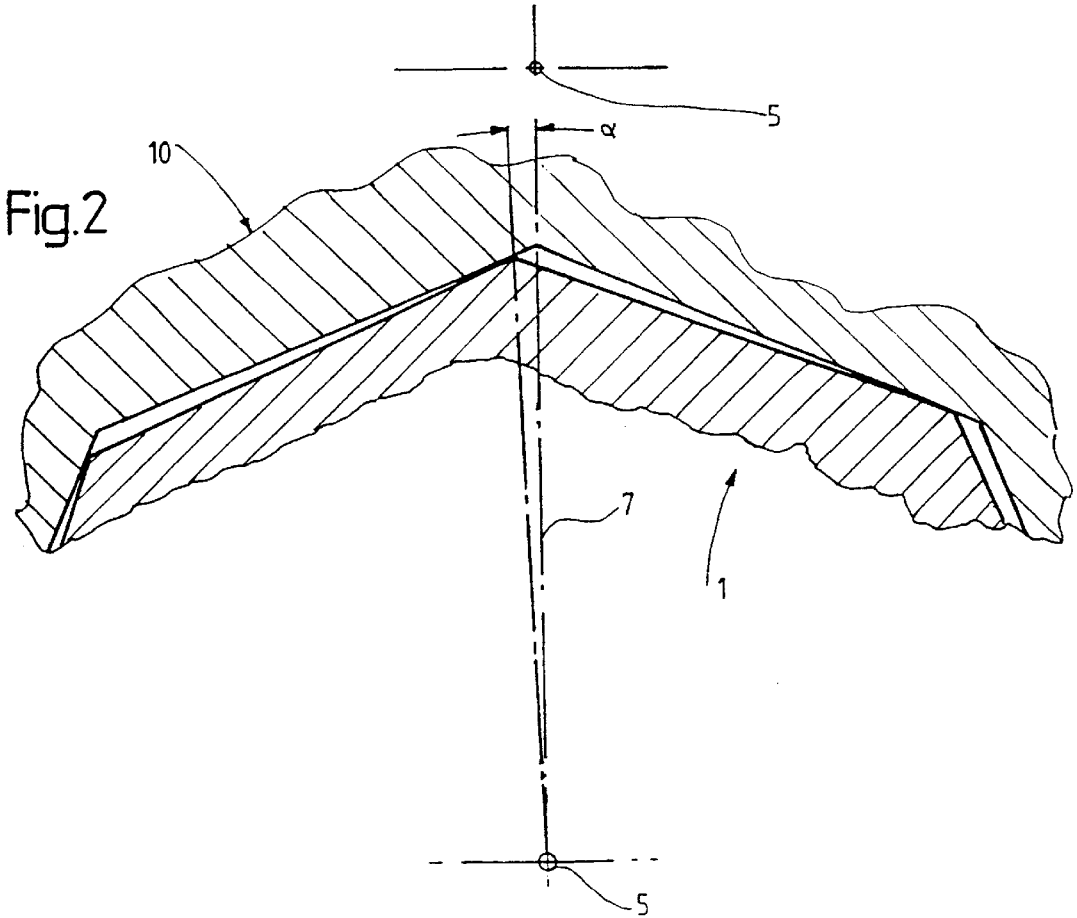
FIG. 2 shows a cross section through the parts shown in FIG. 1, with the cap rotated out of the desired rotational position.

FIGS. 1 and 2 (Prior Art)
1 support
5 axis
7 radial straight line
10 cap
FIGS. 3–8
21 support
22 axis
23 anchoring part
24 head part
31 implant
32 end section
33 section
34 external thread
35 shoulder of implant
37 shoulder surface
38 edge
41 blind hole
42 opening
43 conical main part
44 shoulder
45 threaded hole
46 internal thread
51 secondary part
52 internal connecting section
53 conical section
54 threaded part
55 external thread
57 shoulder
59 head
60 peripheral surface
61 annular groove
62 positioning section
63 cylindrical section
64 conical section
65 annular face
67 positioning projection
68 first positioning interstice
69 second positioning interstice
71 blind hole
72 internal thread
81 bone
82 soft tissue (gingiva)
83 device
85 healing element or healing cap
86 occlusal screw
91 device
93 superstructure element
101 cap
103 interior space
104 conical supporting surface
105 positioning section
106 positioning projection
108 positioning interstice
109 supporting surface
121 occlusal screw
125 casting
126 lining
131 straight line
132 straight line
FIG. 10
151 device
153 superstructure part
161 cap
165 positioning section
166 first positioning projection
167 second positioning projection
168 positioning interstice
+Parts of FIGS. 3–9
FIG. 11
191 device
193 superstructure element
201 cap
205 positioning section
207 positioning projection
+Parts of FIGS. 3–9
FIGS. 12 and 13
251 device
253 superstructure element
261 cap
263 interior space
264 conical supporting surface
265 conical internal surface
269 conical supporting surface
+parts of FIGS. 3–9
FIGS. 14 and 15
321 support
322 axis
323 anchoring part
324 head part
331 implant
335 implant shoulder
362 positioning section
363 cylindrical section
364 conical section
365 face
367 positioning projection
368 first positioning interstice
269 second positioning interstice
371 blind hole
372 internal thread
FIGS. 16 and 17
421 support
422 axis
4331 implant
435 implant shoulder
437 shoulder surface
439 centering surface
441 blind hole
451 secondary part
462 positioning section
471 cap
481 cap
491 occlusal screw
FIGS. 18, 19, and 20
501 device
521 support
522 axis
523 anchoring part
5243 head part
531 implant
541 blind hole
551 head
552 cylindrical section
553 conical section
562 positioning section
565 face
566 first positioning projection
567 second positioning projection
568 first positioning interstice
569 second positioning interstice 593 superstructure element
601 cap
603 interior space
605 positioning section
606 positioning projection
608 positioning interstice
FIG. 21
651 device
653 superstructure element
661 cap
663 interior space
665 conical internal surface
+parts of FIGS. 18–20
FIG. 22
701 device
721 support
722 axis
723 anchoring part
724 head part
731 implant
759 head
762 positioning section
763 cylindrical section
764 conical section
765 face
766 external thread
771 blind hole
772 internal thread
776 first positioning projection
777 second positioning projection
778 first positioning interstice
778 second positioning interstice
786 first positioning projection
787 second positioning projection
788 first positioning interstice
789 second positioning interstice
793 superstructure element
801 cap
803 interior space
805 positioning section
821 occlusal screw
FIG. 23
901 device
924 head part
931 implant
948 first positioning interstice
961 cap
965 conical internal surface
976 positioning projection
FIGS. 24–28
571 bottom surface
572 lateral surface
611 main body
613 conical internal surface
614 cylindrical hole section
621 positioning sleeve
626 positioning projection
627 positioning projection
+Numbers in FIGS. 18–20
FIG. 29
627 positioning projection
FIG. 30
636 positioning projection
637 edge
+Numbers in FIGS. 24–28
FIGS. 31, 22, and 33
1000 support 1001 implant
1003 axis
1005 anchoring part
1007 head or head part
1008 first end
1009 second end
1011 cylindrical section
1013 expanding trumpet-shaped section
1015 external thread
1016 rib
1017 top
1018 end section
1021 shoulder
1022 shoulder surface
1023 annular surface
1025 head section parallel to axis
1027 conical head section
1029 annular groove
1030 peripheral surface
1031 end surface
1033 positioning surface
1025 bind hole
1036 opening
1037 internal thread
1038 cylindrical hole section
1039 bottom
1051 groove (=chip groove)
1053 chip surface
1067 positioning projections
1068 first positioning interstice (=positioning groove)
1069 second positioning interstice (=positioning groove)
FIGS. 34, 35 and 36
1071 groove and/or hole
1027 central hollow space
FIG. 37
1081 groove
FIGS. 38 and 39
1091 annular groove
1093 blind hole
1094 opening
1095 bottom
1097 lengthwise hole
FIG. 40
As Previous Figures
FIGS. 41 to 43
1111 bone
1113 gingiva
1115 healing element or healing cap
1116 supporting surface
1117 cylindrical section
1119 screw
1120 suture
FIG. 44
1151 device
1153 superstructure element 163 interior space
1164 conical supporting surface
1165 conical internal surface
1167 conical supporting surface
1171 occlusal screw
1172 head
1173 conical section
1174 cylindrical shaft section
1175 thread part
FIGS. 45 and 46
1201 crown
1211 external surface
1212 section of external surface 1213 annular groove
1224 shoulder section
FIGS. 47 and 48
1241 positioning section
12243 positioning projections
1245 positioning interstice
FIG. 49
1243 first positioning projection
1254 second positioning projection
FIGS. 50 and 51
1271 lower section of out surface
1273 upper section of external surface
1275 axis
FIG. 52
As Previous Figures
FIG. 53
1291 ground surface
FIG. 54
As Previous Figures
FIGS. 55 to 58
1301 impression element (=impression cap)
1303 impression spatula
1305 impression material
1307 impression surface
1311 manipulating implant
1315 anchoring part
1317 head
1321 shoulder
1331 master model
FIG. 63
1425 annular depression (=groove)
1427 bottom
1428 first surface
1429 second surface
FIG. 64
14351 turn of rib
1453 foot
1454 flank
1461 depression or channel
1464 radial straight line
FIG. 65
1468 positioning interstices or positioning grooves
+Numbers of FIGS. 31 and 32

What is claimed is:

1. A support for holding or forming a dental prosthesis, said support having an axis and comprising:
   an anchoring part for anchoring the support in a bone or a master model;
   a head part having a peripheral surface and a face;
   several projections and interstices on said head part; and
   an annular shoulder surface disposed between said anchoring part and said head part and forming an angle with said axis,
   said head part projecting from said bone or master model when the support is in use;
   said projections and interstices alternating around said axis;
   said interstices including several first interstices each having the same dimensions; and
   said interstices including a second interstice having a larger dimension in at least one direction than said first interstices.

2. A support according to claim 1, wherein each of said interstices forms a depression relative to a straight line that lies in a plane perpendicular to said axis and contacts said head part on sides of said interstices that face away from each other.

3. A support according to claim 1, wherein said interstices are groove-shaped.

4. A support according to claim 1, wherein said interstices are at least partially delimited by surface sections; said surface sections being approximately parallel to a plane running through said axis and through the center of said interstices or forming an angle of at most 60° with said plane.

5. A support according to claim 4, wherein said angle is at most 45°.

6. A support according to claim 1, wherein each interstice has a bottom and expands away from said bottom of said interstice in cross-section.

7. A support according to claim 1, wherein each interstice has two flat, lateral surfaces or is at least partially concavely curved in cross-section.

8. A support according to claim 1, wherein each interstice forms an arc of a circle in cross-section that is at most 18°.

9. A support according to claim 1, wherein said second interstice has a greater width or depth than said first interstices; said width being measured tangentially to a circle abutting said projections.

10. A support according to claim 1, wherein said head part comprises:
    a free end forming said face;
    a section generally parallel to said axis; and
    a generally conical section tapering away from said section generally parallel to said axis and toward said free end,
    wherein said interstices are at least partially located in said generally conical section.

11. A support according to claim 1, wherein
    said head part has a free end facing away from said anchoring part; and
    each of said interstices is disposed at said peripheral surface and has a bottom parallel to said axis and extending to said free end.

12. A support according to claim 1, wherein
    said interstices are disposed at said face and are separated from each other by projections; and
    said projections have tops disposed in said face and said interstices are open at the ends facing away from each other.

13. A support according to claim 1, wherein said anchoring part comprises:
    an implant; and
    a secondary part separate from said implant and comprising said projections and said interstices,
    wherein said implant has a blind hole with an internal thread;
    said secondary part consists of a one-piece body and has a section projecting into said blind hole; and
    said secondary part is removably screwed to said implant.

14. A support according to claim 1, wherein said interstices define a division of a circle with n parts; and n is at least six.

15. A support according to claim 14, wherein n is at least eight.

16. A support according to claim 14, wherein n is at least twelve.

17. A support according to claim 1, wherein said projections each have a top lying in a plane perpendicular to said axis; and said interstices each have a bottom lying in said plane perpendicular to said axis.

18. A support according to claim 1, wherein the support comprises a one-piece body which extends from a first free end to a second free end; said anchoring part forming said first free end of the support, and said face of the head forming said second free end of the support.

19. A support for holding or forming a dental prosthesis, said support having an axis and comprising:
    an anchoring part for anchoring the support in a bone or master model;
    a head part having a peripheral surface and a face;
    several projections and interstices on said head part; and
    an annular shoulder surface disposed between said anchoring part and said head part and forming an angle with said support axis,
    said projections and interstices alternating around said axis;
    said head part projecting from said bone or master model when the support is in use;
    at least said head part being formed of a one-piece body; and
    said head part one-piece body having a hole which is coaxial with said support axis and which has an opening surrounded by said face, and an internal thread.

20. A support for holding or forming a dental prosthesis, said support having an axis and comprising:
    an anchoring part for insertion into a bone or into a master model;
    a head part having a plurality of interstices; and
    an annular shoulder surface disposed between said anchoring part and said head part and forming an angle with said axis;
    said head part projecting from said bone or master model when the support is in use and comprising a generally conical section and a section generally parallel to said axis and several positioning surfaces;
    said generally conical section tapering away from said anchoring part to a tapered end;
    said positioning surfaces being distributed around and extending along said axis and being rotationally asymmetrical with said axis and being located in said generally conical section and having areas in said generally conical section generally parallel to said axis;
    at least one central cross-sectional area extending to said tapered end; and
    said interstices comprising several first interstices with the same dimensions and a second interstice that has a larger dimension than said first interstices in at least one direction.

21. A support according to claim 20, wherein said positioning surfaces are flat or formed by groove-shaped interstices.

22. A support according to claim 20, wherein
    said shoulder surface is conical, and said angle formed with said axis is larger than an angle between the support axis and said generally conical section of said head part; or
    said shoulder surface is perpendicular to said axis and forms an annular channel together with a centering surface extending away from said shoulder surface to said head part.

23. A support according to claim 22, wherein said centering surface tapers conically toward said head part.

24. A support according to claim 22, wherein
    said shoulder surface defines a conical or a flat surface and has an outer edge; and
    said generally conical section defines a conical surface that intersects said conical or flat surface defined by said shoulder surface in an area enclosed by said outer edge of said shoulder surface at a distance from said outer edge of said shoulder surface.

25. A support according to claim 22, wherein
    said head part has a free end that faces away from said anchoring part;
    said free end of said head part being spaced a distance from an inner edge of said conical shoulder surface or said centering surface; and
    said distance being at most 2 mm.

26. A support according to claim 25, wherein said distance is at least 1.2 mm.

27. A support according to claim 20, wherein said generally conical section of said head part forms an angle of 15° to 25° with said axis.

28. A support for holding or forming a dental prosthesis, said support having an axis and comprising:
    an anchoring part for anchoring the support in a bone and comprising a self-cutting external thread and at least one enlongated hole or at least one enlongated groove,
    said self-cutting external thread having at least one rib running along a helix;
    said hole or groove forming a chip surface of at least turn of said at least one rib of said external thread;
    said chip surface forming an acute chip angle at the top of said rib with a straight line running through said axis; and
    said chip surface being inclined in a view radial to said axis toward the same side of said axis as said rib and forming an acute lead angle with said axis in a view radial thereto.

29. A support according to claim 28, wherein each of said ribs disposed between said hole or groove and an end of the support intended to project out of said bone has a section that surrounds said axis uninterruptedly at least once.

30. A support for holding or forming a dental prosthesis, said support having an axis and comprising:
    an anchoring part for anchoring the support in a bone; and
    an external thread on said anchoring part,
    said external thread comprising at least one rib;
    each said at least one rib having a turn forming a helix, a top, a foot, and two flanks;
    corresponding points of two adjacent turns of said at least one rib being spaced apart a distance s;
    each said at least one rib having an axial dimension a at its mid-height;
    said axial dimension a being a maximum of 30% of said distance s; and
    said flanks of said at least one rib having a straight flank section in axial section that forms an angle of 15° to 25° with a radial straight line.

31. A support according to claim 30, further comprising:
    a channel with a cylindrical bottom surface disposed between mutually adjacent of said turns; and
    arcuate sections forming the top of said at least one rib and continuously connecting flank sections of said rib that are straight in axial section, and arcuate sections continuously connecting said flank sections with said cylindrical bottom surface in axial section.

32. A support according to claim 31, wherein said arcuate sections have, in axial section, a radius of curvature of at least 0.1 mm.

33. A support for holding or forming a dental prosthesis, said support having an axis and comprising:

an anchoring part for anchoring the support in a bone; and an external thread on said anchoring part, said external thread comprising at least one rib;

each said at least one rib having a turn forming a helix, a top, a foot, and two flanks;

corresponding points of two adjacent turns of said at least one rib being spaced apart a distance s;

each said at least one rib having an axial dimension a at its mid-height;

said axial dimension a being between 10% and 25% of said distance s; and said flanks of said at least one rib having a straight flank section in axial section that forms an angle of 18° to 22° with a radial straight line.

34. A support for holding or forming a dental prosthesis, said support having an axis and comprising:

a first end forming an anchoring part for insertion into a bone or master model when said support is in use;

a second end, and a blind hole coaxial with the support axis, said blind hole having an internal thread, a bottom, a cylindrical hole section between said bottom and said internal thread; and an opening at said second end of said support; and an annular groove in said blind hole between said internal thread and said cylindrical hole section, wherein said second end of said anchoring part projects from said bone or master model when the support is in use;

said cylindrical hole section having a diameter that is at most equal to a core diameter of said internal thread;

said internal thread having an inner end proximate said bottom;

said blind hole opening into said second end of said support; and said annular groove being at least partially concavely curved in axial section and forming a transition between said inner end of said internal thread and said cylindrical hole section.

35. A support according to claim 34, further comprising:

an essentially cylindrical section; and a section expanding away from said essentially cylindrical section and away from said first end of said support;

wherein said inner end of said internal thread is disposed inside said section expanding away; and said groove is partially delimited by a surface that is approximately parallel to an outer surface of said section expanding away in axial section.

36. A support for holding or forming a dental prosthesis, said support having an axis and comprising:

an anchoring part for anchoring the support in a bone or a master model when the support is in use;

a head part; and an annular shoulder surface disposed between said anchoring part and said head part and forming an angle with said axis, said head part projecting from said bone or master model when the support is in use;

said anchoring part comprising a generally cylindrical section and a section generally expanding away from said generally cylindrical section to said shoulder surface;

said generally expanding section of said anchoring part having depressions at a distance from each other along said axis;

each of said depressions comprising, in axial section, a bottom, a first surface, and a second surface;

said first surface of each said depression being inclined away from said axis from said bottom of said depression to said shoulder surface;

said second surface of each said depression being disposed on a side of said bottom that faces away from said shoulder surface and being directed outwardly away from said bottom and from said axis; and forming a larger angle with said axis than does said first surface of said depression.

37. A support according to claim 36, wherein said depressions are formed by channels surrounding said axis, and wherein said first surfaces and said second surfaces of said depressions are continuously connected with each other at a base and at ends facing away from said base by sections that are arcuate in axial section.

38. A device for holding or forming a dental prosthesis, comprising:

(a) a support having an axis and comprising:

an anchoring part for anchoring the support in a bone or a master model when the support is in use;

a head part having a peripheral surface and a face;

a plurality of projections and interstices disposed on said head part and alternating around said axis; and an annular shoulder surface disposed between said anchoring part and said head part forming an angle with said axis; and (b) an element attachable to the support and having at least two element projections, said head part projecting from said bone or master model when the support is in use;

said interstices comprising several first interstices with the same dimensions and a second interstice that has a larger dimension than said first interstices in at least one direction;

said element projections having the same shapes and being distributed such that said element is positionable relative to said axis in various rotational positions; and said element having a supporting surface for abutting said shoulder surface and surrounding said head part in cross section when said head part is resting on said shoulder surface.

39. A device according to claim 38, wherein said element rests on said shoulder surface in a gap-free manner when it said element is connected to the support; and said element is supported by said head part at a generally conical section of said head part at least pointwise with minimum play.

40. A device according to claim 38, wherein said element is securable against rotations about said axis.

41. A device according to claim 38, wherein said element forms at least one part of a unit selected from the group consisting of a superstructure element, an impression element, and a healing element; or said element is capable of being fired and is used to manufacture a superstructure element.

42. A device for holding or forming a dental prosthesis, comprising:

(a) a support having an axis and comprising:

an anchoring part for anchoring the support in a bone or a master model when the support is in use;

a head part comprising a peripheral surface and a face;

a plurality of projections and interstices disposed on said head part and alternating around said axis; and an annular shoulder surface disposed between said anchoring part and said head part and forming an angle with said axis; and (b) an element attachable to said support comprising a supporting surface intended for abutting said shoulder surface, said head part projecting from said bone or master model when the support is in use;

said interstices comprising several first interstices with the same dimensions and a second interstice that has a larger dimension than said first interstices in at least one direction;

said element having an element projection dimensioned to engage said second interstice and not to engage said first interstices;

said element surrounding said head part in cross section when said head part is resting on said shoulder surface; and said element being positionable in only one rotational position relative to said support axis.

43. A device according to claim 42, wherein said element has additional element projections that each engage one of said first interstices when said element abuts said shoulder surface.

44. A device for holding or forming a dental prosthesis, comprising:

(a) a support having an axis and comprising:
an anchoring part for anchoring the support in a bone or a master model when the support is in use;
a head part comprising a peripheral surface and a face;
a plurality of projections and interstices disposed on said head part and alternating around said axis; and
an annular shoulder surface disposed between said anchoring part and said head part and forming an angle with said axis; and (b) an element attachable to the support comprising a supporting surface for abutting said shoulder surface and surrounding said head part in cross section when said head part is resting on said shoulder surface;
said head part projecting from said bone or master model when the support is in use;
said interstices comprising several first interstices with the same dimensions and a second interstice that has a larger dimension than said first interstices in at least one direction;
said element not engaging said interstices when said element is abutting said shoulder surface; and
said element being positionable in any rotational position relative to said support axis.

45. A device for holding or forming a dental prosthesis, comprising a support having a support axis and a cap attachable to the support, said support comprising an anchoring part for anchoring the support in a bone or master model when the support is in use, a head part having a peripheral surface and a face, and an annular shoulder surface disposed between said anchoring part and said head part and forming an angle with said support axis, said head part projecting from said bone or master model when the support is in use, said head part having a plurality of projections and interstices disposed alternatively around said support axis, wherein the interstices of the head part comprise a plurality of first interstices having the same dimensions and a second interstice that has a larger dimension than said first interstices in at least one direction, said cap having a supporting surface for abutting said shoulder surface and surrounding said support axis, said supporting surface being coaxial to said support axis when said cap is resting on said shoulder surface, said cap further having a first external surface section and second external surface section, said first external surface section being generally rotationally symmetrical with the support axis and said second external surface section being approximately coaxial with a cap axis that forms an angle with the support axis, said cap further having positioning projections that engage the interstices of the head part and secure the cap against rotation about the support axis relative to the support when the cap rests on the shoulder surface of the support.

46. A device according to claim 45, wherein the interstices of the head part and the positioning projections of the cap are configured such that the cap is positionable on the support in various rotational positions relative to said support axis when the cap rests on the shoulder surface of the support.

47. A device according to claim 45, wherein the cap has an interior space which is formed by a through-hole and which is generally rotationally symmetrical with the support axis when the cap rests on the shoulder surface of the support.

48. A device according to claim 47, further comprising a screw for attaching the cap to the support, wherein the support has a hole which is coaxial with said support axis, said hole having an internal thread and opening into said face of the head part, said screw comprising a screw head and a threaded part, and wherein, when the cap is attached to the support, the cap rests on the shoulder surface of the support, the screw head is arranged in the interior space of the cap and the threaded part is screwed into the internal thread of the support.

* * * * *